(12) United States Patent
Barodka

(10) Patent No.: US 12,208,193 B2
(45) Date of Patent: Jan. 28, 2025

(54) CANNULA AND BALLOON SYSTEM FOR EXTRACORPOREAL MEMBRANE OXYGENATION

(71) Applicant: Barzedi, LLC, Troy, MI (US)

(72) Inventor: Viachaslau Barodka, Troy, MI (US)

(*) Notice: Subject to any disclaimer, the term of this patent is extended or adjusted under 35 U.S.C. 154(b) by 0 days.

(21) Appl. No.: 17/392,482

(22) Filed: Aug. 3, 2021

(65) Prior Publication Data
US 2022/0062524 A1    Mar. 3, 2022

Related U.S. Application Data

(60) Provisional application No. 63/071,566, filed on Aug. 28, 2020.

(51) Int. Cl.
*A61M 1/36* (2006.01)
*A61M 1/16* (2006.01)

(52) U.S. Cl.
CPC ........ *A61M 1/3659* (2014.02); *A61M 1/3667* (2014.02); *A61M 1/367* (2013.01); *A61M 1/1698* (2013.01)

(58) Field of Classification Search
CPC .............. A61M 1/3659; A61M 1/3661; A61M 1/3666; A61M 1/3667; A61M 1/1698; A61M 1/367
See application file for complete search history.

(56) References Cited

U.S. PATENT DOCUMENTS

| 5,858,009 | A | * | 1/1999 | Jonkman | ............. | A61M 25/007 |
| | | | | | | 604/526 |
| 7,473,239 | B2 | * | 1/2009 | Wang | .................. | A61M 1/3658 |
| | | | | | | 604/4.01 |

(Continued)

FOREIGN PATENT DOCUMENTS

| JP | 2017-516582 A | 6/2017 |
| WO | 2018/169503 | 9/2018 |

OTHER PUBLICATIONS

Position of draining venous cannula in extracorporeal membrane oxygenation for respiratory and respiratory/circulatory support in adult patients; B. Frenckner et al.; Frenckner et al. Critical Care (2018) 22:163 https://doi.org/10.1186/s13054-018-2083-0.

(Continued)

*Primary Examiner* — Philip R Wiest
(74) *Attorney, Agent, or Firm* — Wilson Dutra, PLLC; Camille A. Wilson

(57) ABSTRACT

The present disclosure provides for a cannula and balloon system for extracorporeal membrane oxygenation. The system may comprise one or more cannula, one or more insertion mechanism, and one or more balloon cuff. The method may comprise venous-venous or venous-arterial insertion into one or more blood vessels or chambers of the heart. The balloon cuff may allow fluid flow to avoid oxygenated blood restriction to a region of the body for the cannula insertion duration. One or both the balloon cuff and dual cannula may prevent occlusion, recirculation, and mixing of oxygenated and deoxygenated blood. When there is a dual cannula, the cannula may comprise a reinfusion cannula and a drainage cannula. A reinfusion cannula may bypass one or more chambers of the heart. When the system comprises more than one cannula, the cannulae may be joined via a cannula connection mechanism.

9 Claims, 45 Drawing Sheets

(56) References Cited

U.S. PATENT DOCUMENTS

| | | | | |
|---|---|---|---|---|
| 2013/0158338 | A1* | 6/2013 | Kelly | A61M 25/0026 |
| | | | | 600/16 |
| 2018/0229012 | A1* | 8/2018 | Tilson | A61M 25/10185 |
| 2019/0247564 | A1* | 8/2019 | Lu | A61M 1/3607 |
| 2021/0178047 | A1* | 6/2021 | Haneef | A61M 1/3659 |

OTHER PUBLICATIONS

Cannulation techniques for extracorporeal life support; Evgeny Pavlushkov et al.; Submitted Aug. 26, 2016. Accepted for publication Oct. 17, 2016. doi: 10.21037/atm.2016.11.47; View this article at: http://dx.doi.org/10.21037/atm.2016.11.47.
What is ECMO ?; Am J Respir Crit Care Med vol. 193, p. 9-p. 10, 2016, Online version updated Mar. 2020; ATS Patient Education Series © 2016 American Thoracic Society; www.thoracic.org.
Cannulation Strategies in Adult Veno-arterial and Veno-venous Extracorporeal Membrane Oxygenation: Techniques, Limitations, and Special Considerations; Arun L Jayaraman et al.; © 2017 Annals of Cardiac Anaesthesia | Published by Wolters Kluwer-Medknow.

\* cited by examiner

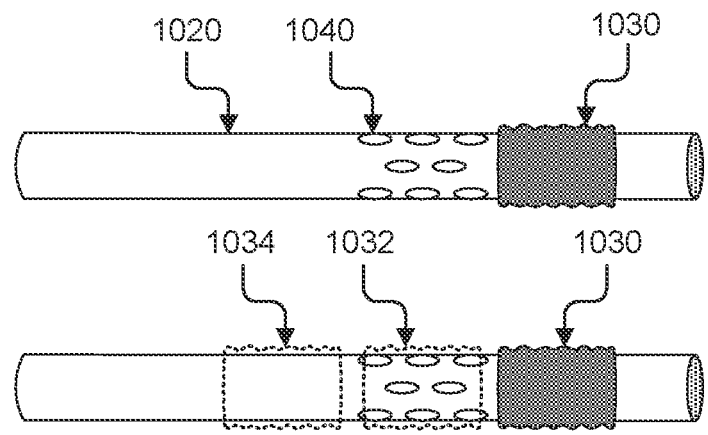
FIG. 10A
FIG. 10B
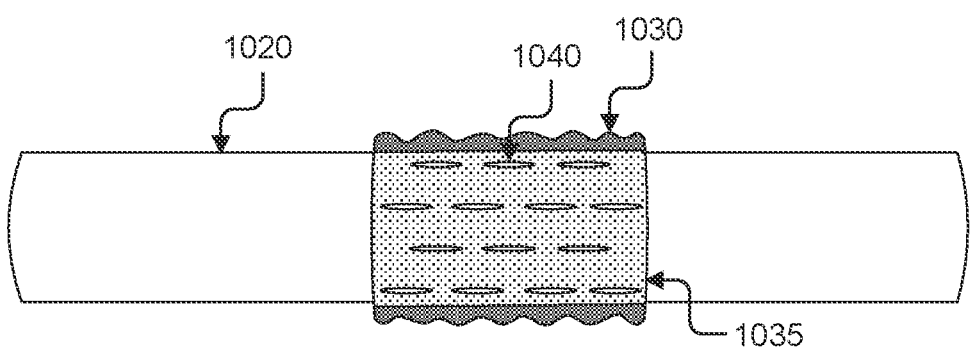
FIG. 10C
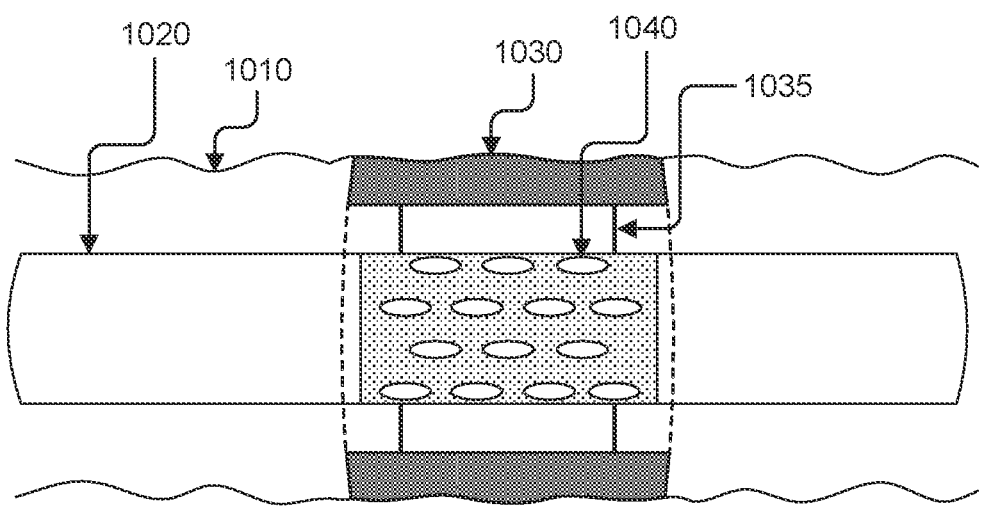
FIG. 10D

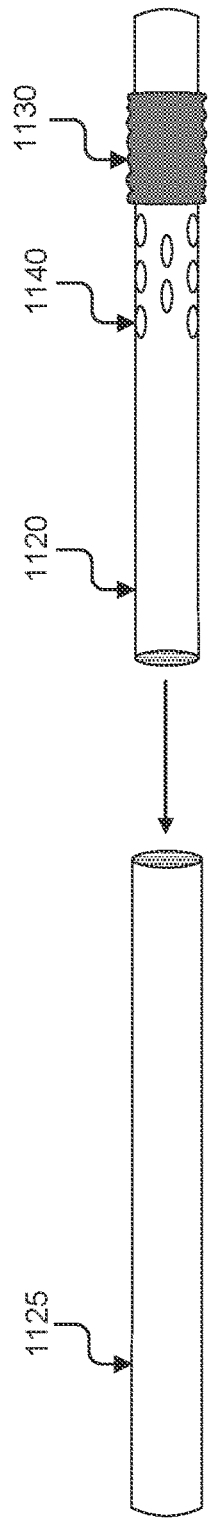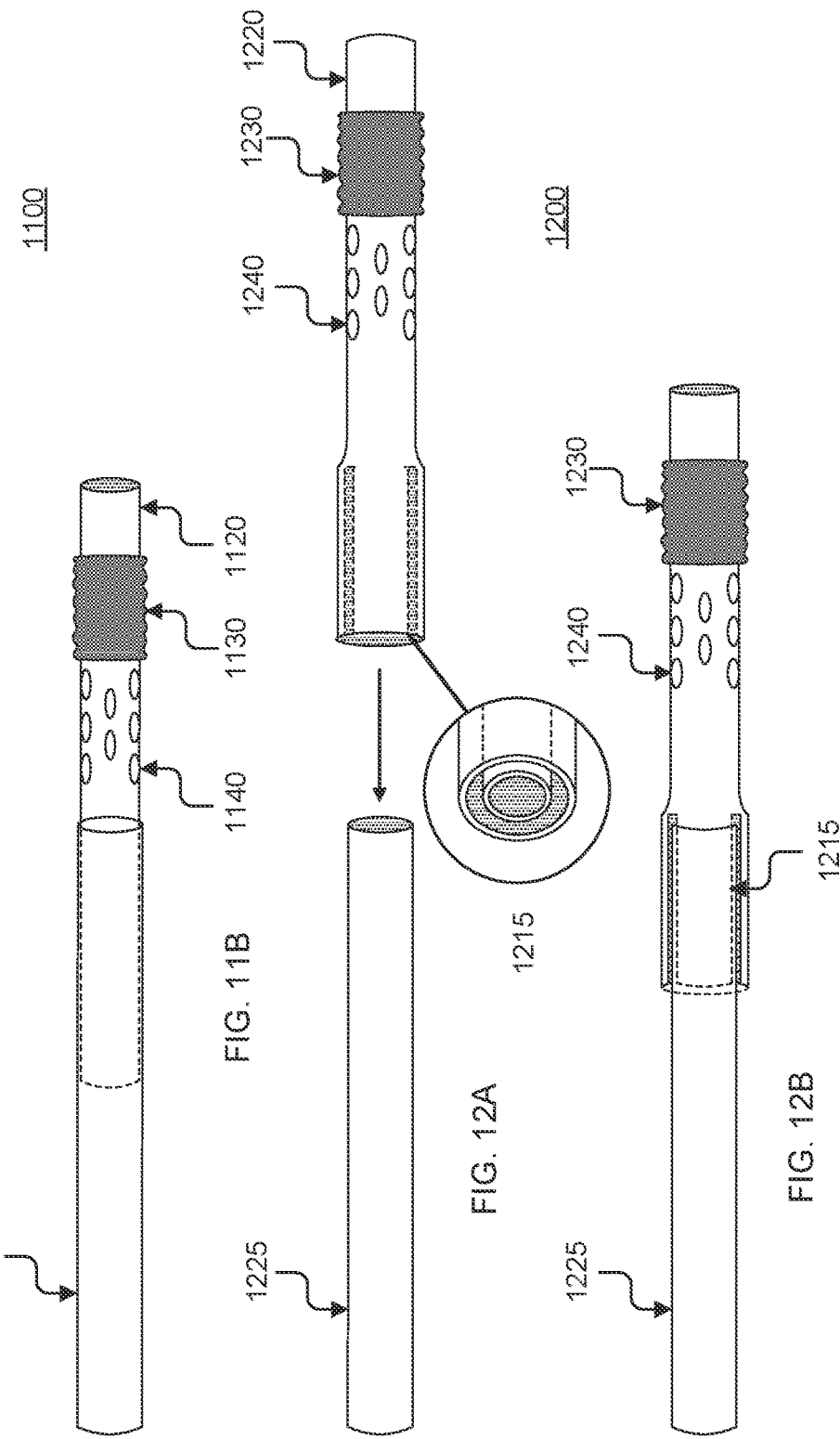
FIG. 11A
FIG. 11B
FIG. 12A
FIG. 12B

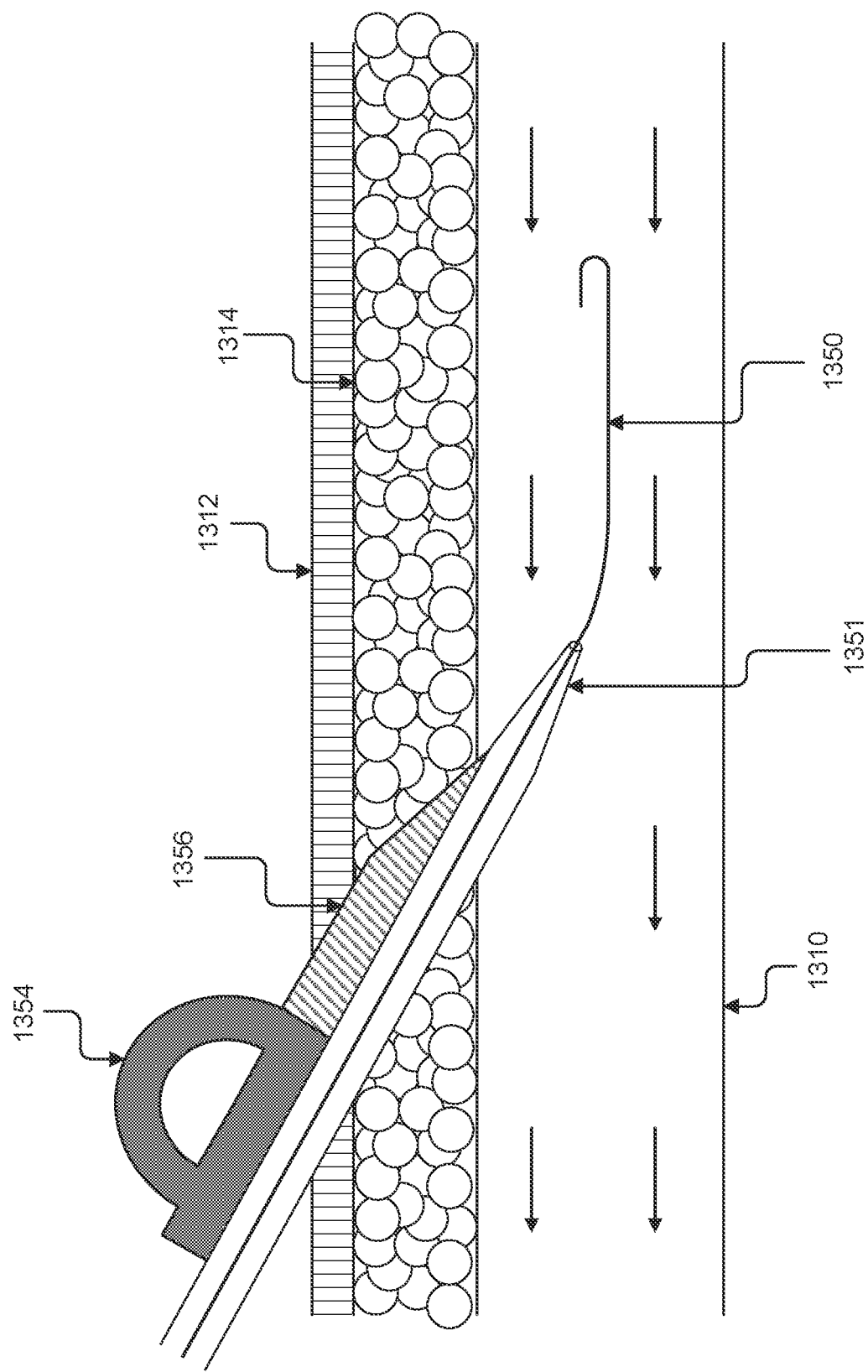

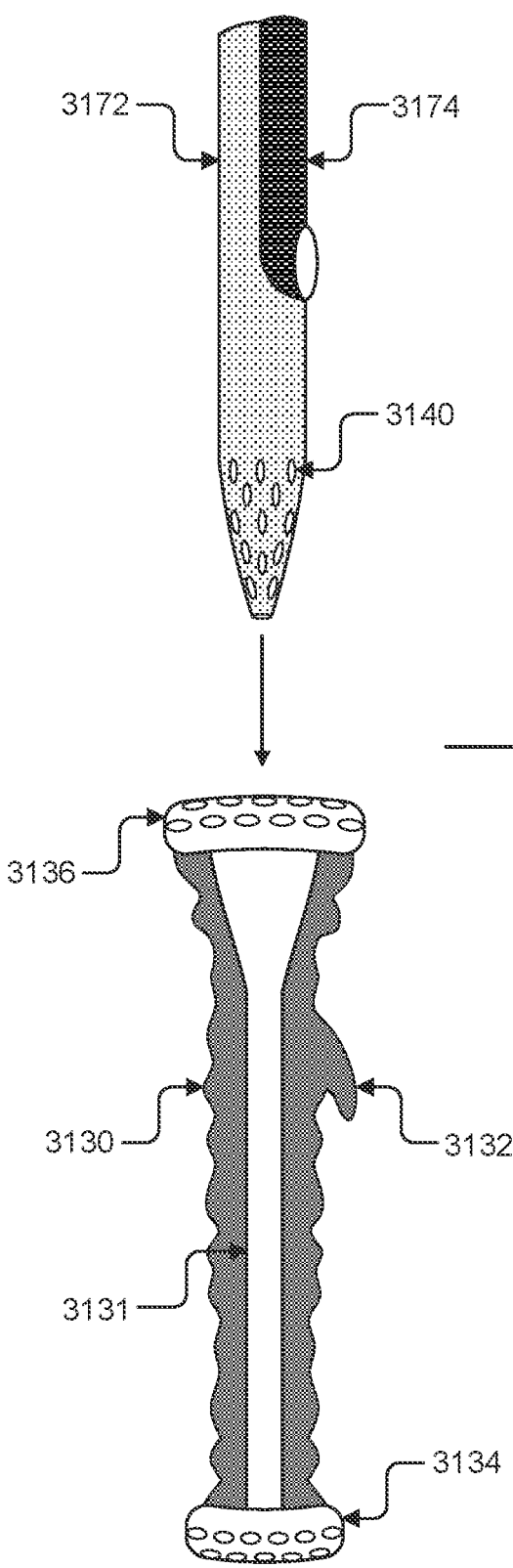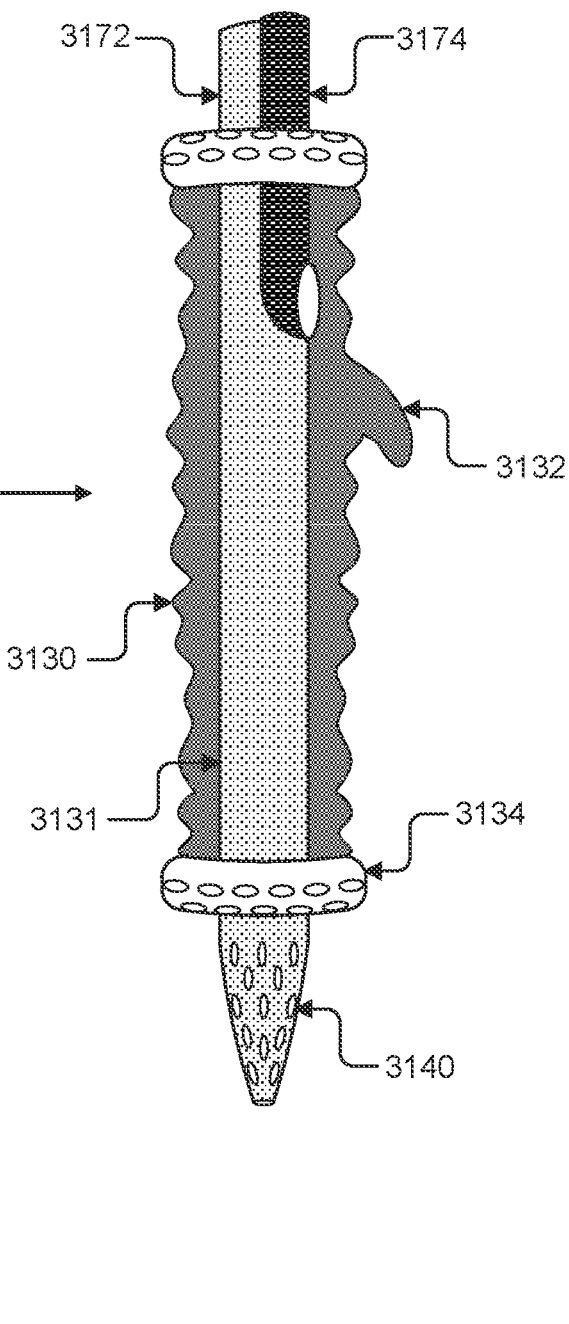
FIG. 31A
FIG. 31B

CANNULA AND BALLOON SYSTEM FOR EXTRACORPOREAL MEMBRANE OXYGENATION

CROSS-REFERENCE TO RELATED APPLICATION

This application claims priority to and the full benefit of U.S. Provisional Patent Application Ser. No. 63/071,566, filed Aug. 28, 2020, and titled "CANNULA AND BALLOON SYSTEM FOR EXTRACORPOREAL MEMBRANE OXYGENATION", the entire contents of which are incorporated in this application by reference.

BACKGROUND

In humans, oxygen is carried by red blood cells which pumped by the heart to the entire body through arteries. The deoxygenated blood then travels back to the heart through veins. The blood from the bottom half of the body returns to the heart through the inferior vena cava (IVC), while the blood from the upper half of the body returns through the superior vena cava (SVC). Both the IVC and SVC lead into the right atrium of the heart. This blood then goes to the right ventricle, where it is pumped through the pulmonary artery to the alveoli in the lungs and oxygen enters the blood through thin-walled capillary vessels. The oxygenated blood is then delivered into the left atrium through the pulmonary veins, then the left ventricle, where the oxygenated blood is finally released into the aorta and pumped throughout the entire body, to begin the cycle again.

Hypoxemia, or having low amounts of oxygen in your blood, may result in hypoxia, or having low amounts of oxygen in your tissue. Suffering from hypoxia for even a few minutes may result in organ damage or failure. This is why it is crucial for the body to oxygenate the blood in the lungs so that oxygen may be properly transported throughout the body. Hypoxemia may occur from multiple different reasons: low oxygen concentration in breathing air, air not reaching the alveoli of the lung, or difficulty for oxygen molecules to diffuse from air into the red blood cells in lung tissue. In general, these issues are referred to as respiratory failure. Hypoxia may also results from heart failure when the heart is unable to pump blood either to the lungs (right heart failure) or to body tissues (left heart failure or cardiogenic shock). Several resultant maladies from these systematic failures are examples of how these failures in oxygen delivery to the tissues prevent the body from performing this natural task.

The most common cause of respiratory failure is pneumonia. This may occur when inflammation of the lung tissue prevents oxygen molecules to diffuse inspired air into the red blood cells passing through the lung capillaries. Pneumonia can be caused by either infections (viral, bacterial or fungal), autoimmune or chemical or physical damage to the lung tissues. Severe viral pneumonia may be caused by influenza viruses, adenoviruses and coronaviruses to name a few. This is a well-known cause of devastating respiratory failure, hypoxemia and patient death. Since 2019, the most common worldwide cause of respiratory failure and death is the viral COVID-19 pneumonia which is caused by severe acute respiratory syndrome coronavirus 2 (SARS-CoV-2).

Similarly, there are multiple reasons of heart failure including ischemic, autoimmune, idiopathic and viral cardiomyopathies. Diabetes, hypertension and advanced age can also lead to the heart failure. Pericardial effusion and cardiac tamponade occurs when the sac around the heart fills with fluid from inflammation, bleeding or renal failure, thereby placing external pressure on the heart and preventing it from pumping blood and correctly doing its job. Both the COVID 19 viral infection itself as well as vaccines to prevent it have been implicated as a cause of heart damage and heart failure due to myocarditis and pericarditis.

In intensive care scenarios where the heart or lungs are not properly working, the physician may turn to using extracorporeal membrane oxygenation (ECMO). There are 2 types of ECMO: Veno-Venous ECMO (VV ECMO) and Veno-Arterial ECMO (VA ECMO). In VV ECMO the deoxygenated blood is removed from the patient veins by a cannula, passed through an oxygenator (artificial lung) to deliver oxygen to the red blood cells, and then oxygenated blood returns into central veins or the right side of the heart through a cannula. This process may be used in instances where only the lungs are not working. This scenario is referred to as veno-venous (VV), wherein the blood is transported back to the heart to allow the heart to properly pump the blood through the body.

The second scenario is referred to as veno-arterial (VA) ECMO. Here, where the heart or both the heart and lungs are not working properly, the deoxygenated blood is removed from the patient veins via a cannula, passed through an oxygenator and then oxygenated blood may be returned back into the body through the cannula in the artery with an applied pressurization, ensuring to pump the blood to the body using arterial system.

In VA ECMO, where the blood is returned through the artery, the process bypasses both the heart and lungs. The most commonly used arteries to place arterial cannula are femoral, axillary or aorta. However, the patient generally suffers from arterial occlusion when the diameter of the arterial cannula is similar to the diameter of the artery and hence loses use of the leg or arm below the femoral or axillary placement. Since the cannula enters the femoral or axillary arteries facing up (towards the heart), the artery traveling down the leg or arm is occluded, or blocked, and the leg or arm does not receive the oxygenated blood. This occlusion generally results in total loss of the leg or arm.

Where the heart is working, but the lungs are unable to oxygenate the blood, the cannula is placed through the SVC, IVC, or both for multiple cannulae, pumping oxygenated blood directly into the right atrium of the heart. However, where the right side of the heart is not working, the cannula is placed though SVC, IVC, or both for multiple cannulae pumping blood directly into the pulmonary artery. If both the lungs and the right heart do not work, then oxygenated blood may be pumped into pulmonary artery or left atrium.

Removal of the deoxygenated blood from the body by drainage cannula placed in the central veins is facilitated by applying suction (negative pressure) to the drainage cannula. This negative pressure is transferred to the veins and cause flexible walls of the vein to suck into the cannula walls and sometimes block the drainage openings on the cannula causing restriction of flow. Mixing of the oxygenated and deoxygenated blood may occur when blood flow via the SVC or IVC exceeds the flow in the cannulas. Oxygenated blood returned into the patient by the reinfusion cannula may be sucked back into the drainage cannula placed through SVC or IVC causing recirculation. Restriction of flow, mixing, and recirculation during ECMO may still cause hypoxemia and result in organ damage or failure.

SUMMARY OF THE DISCLOSURE

What is needed is a method for introducing oxygenated blood into the body without restricting blood flow. It is also needed for the oxygenated blood to be protected from recirculation and mixing. Venous cannulas with balloons may prevent recirculation and mixing by separating the heart from the surrounding blood vessels. Current ECMO methods will inevitably restrict blood flow to peripheral limbs upon insertion of the cannula that can result in the loss of limbs. By introducing blood flow into the obstructed region of the blood vessel, oxygenated blood can continue to sustain peripheral limbs.

The present disclosure provides for a cannula and balloon system for extracorporeal membrane oxygenation. The system may comprise one or more cannula, one or more insertion mechanism, and one or more balloon cuff. The method may comprise venous-venous or venous-arterial insertion into one or more blood vessels. In some embodiments, a distal cannula of venous-venous insertion may be placed into the pulmonary artery or the left atrium, thereby allowing the VV ECMO system to function also as a RV assistance device. In some implementations, a distal cannula of venous-venous insertion may be advanced though right atrium into left atrium and then into left ventricle and finally placed into ascending aorta, thereby allowing the system to function as a VA ECMO or LV assistance device.

The balloon cuff may allow fluid flow to avoid oxygenated blood restriction to a region of the body for the cannula insertion duration. One or both the balloon cuff and dual cannula may prevent occlusion, recirculation and the mixing of oxygenated and deoxygenated blood. This may improve the potency of oxygenated blood injected into the body. When there is a dual cannula, the cannula may comprise a reinfusion cannula and a drainage cannula. When the system comprises more than one cannula, the cannulae may be joined via a cannula connection mechanism.

The present disclosure relates to a cannula system that may include a cannula that may comprise a tubing with an external end and an internal end insertable into a vessel of a patient for flowing fluid through the vessel; and a balloon located proximate to the internal end and insertable into the vessel, where the balloon may be configured to surround the tubing, and when inserted into the vessel and inflated, the balloon secures the cannula within the vessel.

Implementations may comprise one or more of the following features. When the balloon may be inserted into the vessel and inflated, the balloon may limit occlusion of the vessel. When the balloon may be inserted into the vessel and inflated, the balloon may limit flow of fluid within the vessel limiting recirculation. When the balloon may be inserted into the vessel and inflated, the balloon prevents mixing of deoxygenated and oxygenated blood. One or both the cannula when inserted or the balloon when inserted and inflated may maintain a circumference of the vessel.

The balloon may comprise a positioning arm, where the positioning arm secures the balloon within the vessel. The positioning arm positions the balloon between a vena cava within a heart of the patient. The cannula may comprise a reinfusion cannula and drainage cannula, where the drainage cannula surrounds the reinfusion cannula. The reinfusion cannula may extend beyond the drainage cannula. The insertion of the reinfusion cannula and drainage cannula may occur simultaneously via a double lumen needle. The double lumen needle further may comprise a first insertion mechanism for the reinfusion cannula and a second insertion mechanism for the drainage cannula.

The first insertion mechanism and second insertion mechanism guide placement of the reinfusion cannula and drainage cannula to different positions within the vessel or a heart. The first insertion mechanism and second insertion mechanisms guide placement of the reinfusion cannula and drainage cannula to one or more directional orientations. At least a portion of the internal end may comprise a plurality of openings configured to allow for flow of fluid. The plurality of openings may be located before the balloon in the insertable end.

The plurality of openings may be located after the balloon in the insertable end. The plurality of openings may be configured to allow for flow of oxygenated fluid in multiple directions within the vessel. The balloon may comprise a plurality of openings configured to allow for flow of fluid. The plurality of openings facilitates drainage of fluid or blood through the balloon. The plurality of openings may comprise reinfusion openings that assist in prevention of ischemia.

The present disclosure relates to a cannula system that may include a reinfusion cannula that may comprise a first tubing with an external end and an internal end insertable into a vessel of a patient for flowing oxygenating fluid through the vessel; a drainage cannula may comprise a second tubing with an external end and an internal end insertable into the vessel of a patient for flowing deoxygenated fluid from the vessel; and a first balloon insertable into the vessel, where the balloon may be configured to surround one or both the reinfusion cannula and the drainage cannula, and when inserted into the vessel and inflated, the first balloon secures one or both the reinfusion cannula and the drainage cannula within the vessel.

Implementations may comprise one or more of the following features. The drainage cannula may surround the reinfusion cannula. The internal end of the reinfusion cannula may extend further than the internal end of the drainage cannula. The first tubing of the reinfusion cannula and the second tubing of the drainage cannula may be coupled together by one or more connection mechanisms. The first balloon may be insertable into a vena cava of the patient. The first balloon may comprise a positioning arm configured to position the first balloon within the vena cava.

The reinfusion cannula may extend into a heart of the patient. The first balloon may limit flow of deoxygenated fluid into the heart. The reinfusion cannula may be configured to insert into one or more of a pulmonary artery, a left atrium, a left ventricle, where insertion into the pulmonary artery, left atrium, or the left ventricle supports a right ventricle. The reinfusion cannula may be configured to insert into an ascending aorta, where insertion into the ascending aorta supports one or more of a left ventricle and a right ventricle.

BRIEF DESCRIPTION OF THE DRAWINGS

The accompanying drawings that are incorporated in and constitute a part of this specification illustrate several embodiments of the disclosure and, together with the description, serve to explain the principles of the disclosure:

FIG. 10A illustrates an exemplary cannula system with balloon cuff, according to some embodiments of the present disclosure.

FIG. 10B illustrates an exemplary cannula system with balloon cuff, according to some embodiments of the present disclosure.

FIG. 10C illustrates an exemplary cannula system with balloon cuff, according to some embodiments of the present disclosure.

FIG. 10D illustrates an exemplary cannula system with balloon cuff, according to some embodiments of the present disclosure.

FIG. 11A illustrates an exemplary cannula system, according to some embodiments of the present disclosure.

FIG. 11B illustrates an exemplary cannula system, according to some embodiments of the present disclosure.

FIG. 12A illustrates an exemplary cannula system, according to some embodiments of the present disclosure.

FIG. 12B illustrates an exemplary cannula system, according to some embodiments of the present disclosure.

FIG. 13C illustrates an exemplary insertion step for a cannula system, according to some embodiments of the present disclosure.

FIG. 31A illustrates an exemplary cannula system with connector mechanism, according to some embodiments of the present disclosure.

FIG. 31B illustrates an exemplary cannula system with connector mechanism, according to some embodiments of the present disclosure.

DETAILED DESCRIPTION

The present disclosure provides generally for an improved cannula system and apparatus for use during ECMO. According to the present disclosure, the cannula system may comprise a cannula and balloon that may be inserted into a vessel. In some aspects, the balloon may limit flow of blood within the vessel to limit mixing or recirculation. In some embodiments, the balloon may limit risk of occlusion.

In the following sections, detailed descriptions of examples and methods of the disclosure will be given. The description of both preferred and alternative examples, though thorough, are exemplary only, and it is understood to those skilled in the art that variations, modifications, and alterations may be apparent. It is therefore to be understood that the examples do not limit the broadness of the aspects of the underlying disclosure as defined by the claims.

GLOSSARY

Balloon: as used herein refers to an inflatable mechanism, wherein inflation occurs when the cannula is inserted in a blood vessel. In some aspects, an inflated balloon may prevent occlusion of the blood vessel during ECMO. In some embodiments, a balloon may comprise a balloon blood flow mechanism that may allow for the free flow of blood in either direction in the blood vessel.

Cannula System: as used herein refers to a combined system of a cannula and balloon.

Flow Mechanism: as used herein refers to any mechanism that may allow for increased blood flow from, to, or through the cannula system.

Vessel: as used herein refers to, unless specifically designated, venous and arterial blood vessels interchangeably.

Artery: as used herein refers to, unless specifically designated, any artery within the human body. This may include, but not be limited to the femoral artery, the aorta, or the subclavian artery.

Figure 1:
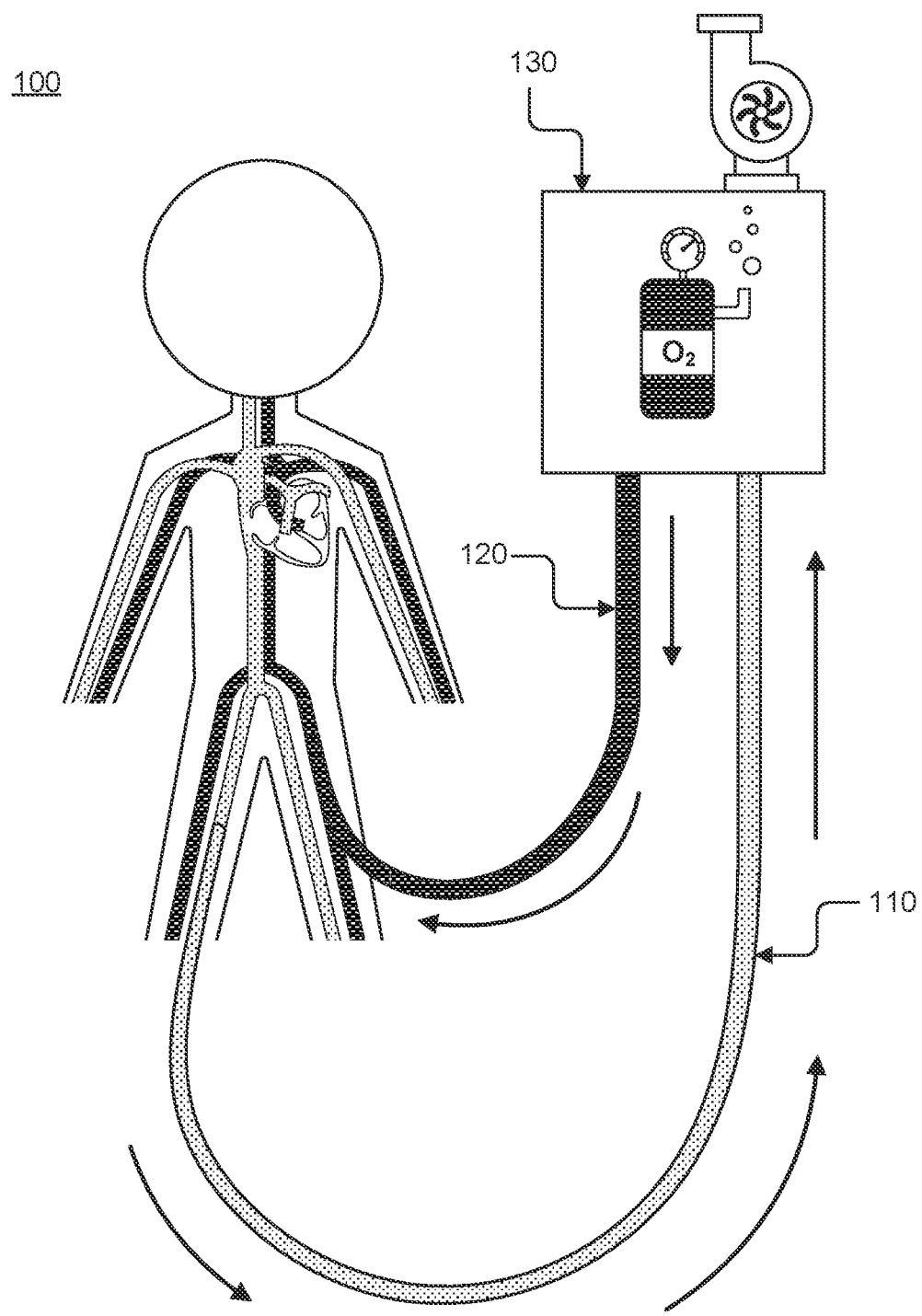
FIG. 1 illustrates an exemplary arterial-venous ECMO system, according to some embodiments of the present disclosure.

Referring now to FIG. 1, an exemplary veno-arterial ECMO system 100 is illustrated, wherein deoxygenated blood 110 is removed from a femoral vein and oxygenated blood 120 is cycled back into the body through the femoral artery. In some embodiments, the system may comprise a number of cannula, pump, oxygenator 130. In some aspects, the ECMO may be initiated percutaneously. In some implementations, the veno-arterial ECMO system may be initiated by surgical cut-down via femoral artery and femoral or internal jugular vein access, or via axillary artery or via right atrium and ascending aorta when chest is open, as a non-limiting list.

Figure 2:
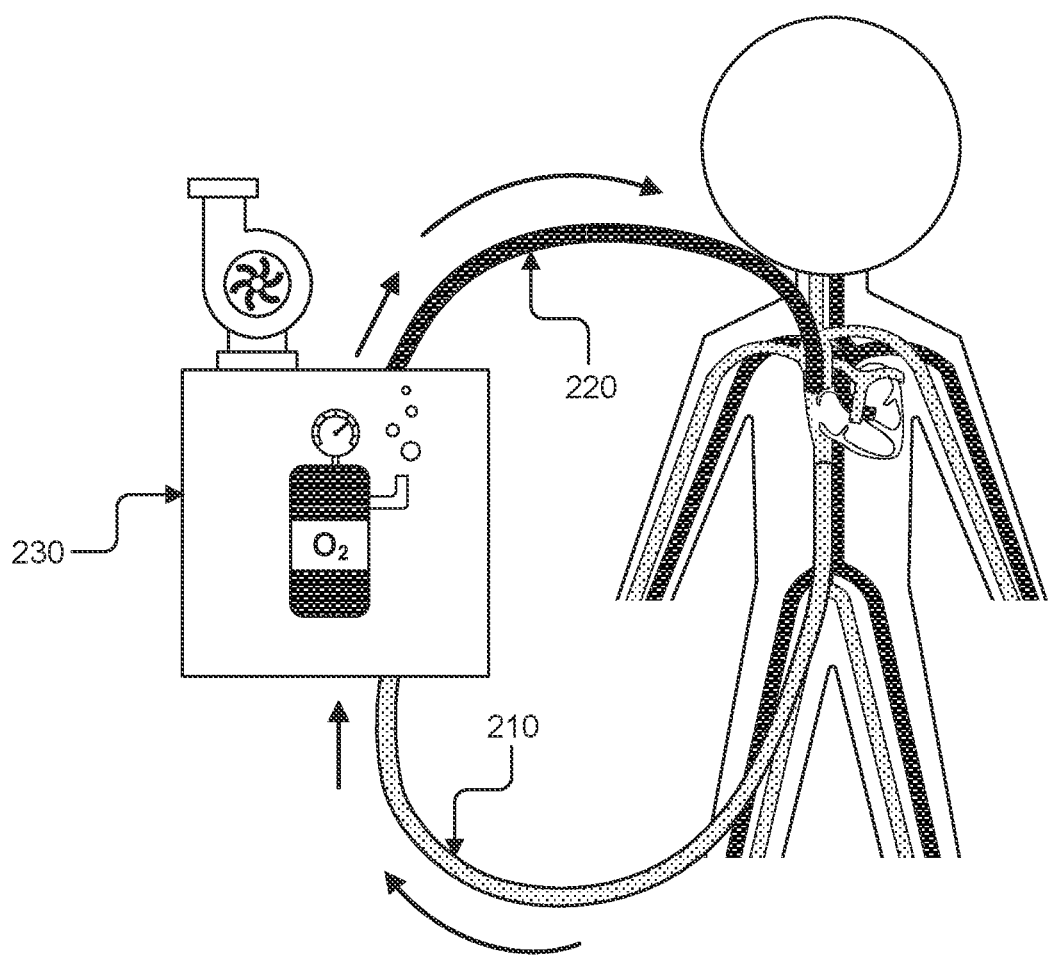
FIG. 2 illustrates an exemplary venous-venous ECMO system, according to some embodiments of the present disclosure.

Referring now to FIG. 2, an exemplary veno-venous ECMO system 200 is illustrated, wherein deoxygenated blood 210 is removed and oxygenated blood 220 is returned to the bloodstream near the heart. In some embodiments, a cannula may be placed within a vein near or inside the heart. For example, the cannula may be able to withdraw deoxygenated blood 210 and return oxygenated blood 220 from the oxygenator 230 to the blood stream. In some implementations, cannulae may be placed in different veins.

Figure 3:
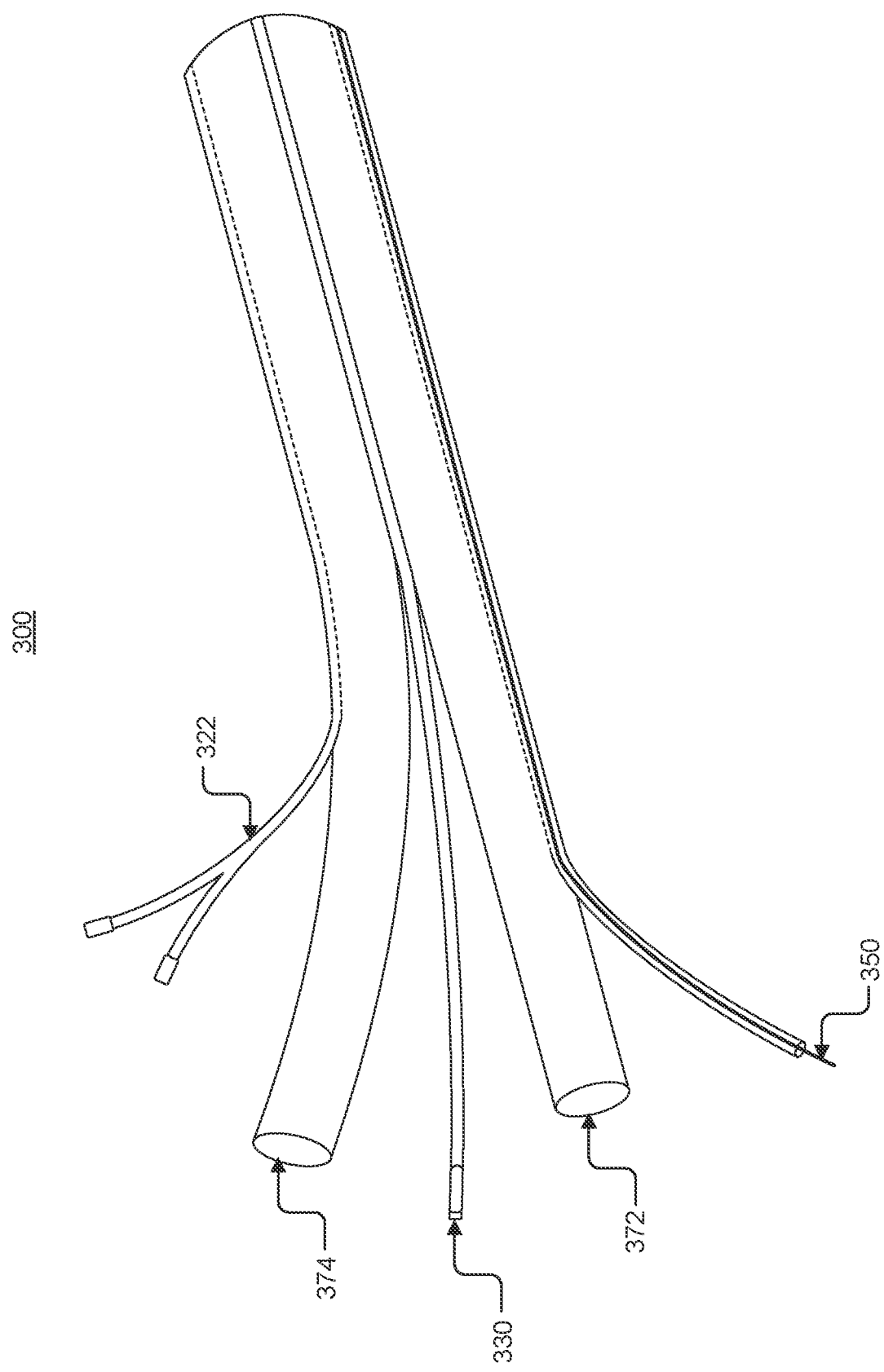
FIG. 3 illustrates an exemplary cannula system, according to some embodiments of the present disclosure.

Referring now to FIG. 3, a partially exploded view of an exemplary cannula system 300 is illustrated. In some embodiments, the cannula system 300 may contain a plurality of cannula. In some aspects, the cannula system 300 may utilize a drainage cannula 372 to remove deoxygenated blood from the body. In some embodiments, a reinfusion cannula 374 may be employed to insert oxygenated blood into the body. There is no limiting order to which the components of the cannula system 300 may be arranged. In some implementations, the cannula system 300 may include a fluids port 322. In some aspects, the fluids port 322 may comprise a plurality of tubes to supply intravenous fluids and medications to the body. For example, the fluids port 322 may allow one or both IV fluids and any of the IV medications to enter the blood stream while utilize another small tube to supply another IV medication. An additional fluid port 322 may allow supply of anti-inflammatory, sedation, paralytic, antibiotic medications or used to provide parenteral nutrition.

In some embodiments, the cannula system 300 may comprise a balloon cuff inflation tube 330 to inflate the balloon 430 to prevent blood mixing from IVC, SVC and right atrium. In some implementations, the balloon cuff inflation tube 330 may allow for inflation of a balloon cuff once inserted and placed within a blood vessel. Inserting a balloon cuff in a deflated state may allow for effective insertion of the cannula system 300 into the blood vessel. In some implementations, the balloon cuff inflation tube 330 may inflate the balloon cuff within the blood vessel via a fluid or gas. As a nonlimiting example, a saline mixture may be inserted into the balloon cuff inflation tube 330 to ensure nothing harmful is released into the bloodstream if the integrity of the balloon cuff is compromised by a small tear in the surface of the balloon cuff inflation tube 330 or balloon cuff. In some implementations, there may be multiple balloon cuff inflation tubes 330 for more than one balloon cuff, or there may be multiple balloon cuffs coupled to a single balloon cuff inflation tube 330.

In some aspects, an insertion mechanism 350 may be utilized to provide guidance and stability while inserting the cannula system 300 into the blood vessel. In some embodiments, the cannula system 300 may utilize the insertion mechanism 350 as a preliminary evaluation of an intended insertion location for the cannula system 300. Combining the different cannulas may allow for a single insertion point, which may reduce risk of misplacement of each of the cannulas if inserted separately.

In some embodiments, the insertion mechanism 350 may reside within the wall of cannula system 300. Internal retention of the insertion mechanism 350 may allow for manipulation of the cannula system 300 in novel ways of placement, withdrawal, advancement, or replacement without accessing the drainage cannula 372 or the reinfusion cannula 374.

Figure 4:
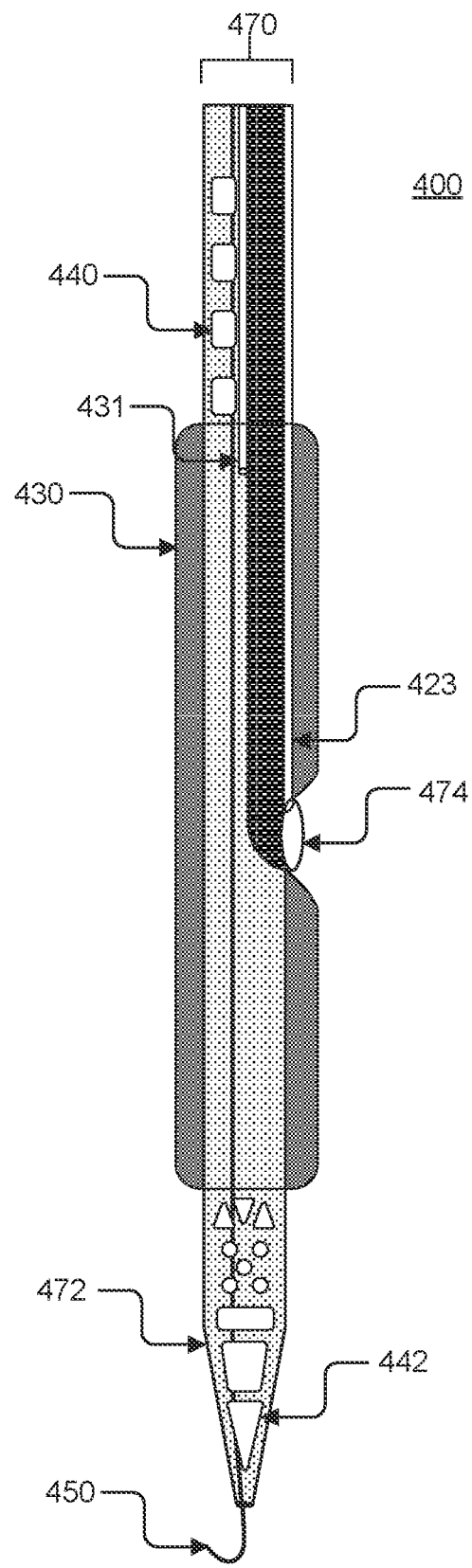
FIG. 4 illustrates an exemplary cannula system, according to some embodiments of the present disclosure.

Referring now to FIG. 4, an exemplary venous cannula system 400 is illustrated. The exemplary venous cannula system 400 may be coupled to and situated opposite from a venous cannula system as referred to in FIG. 3, so that the two systems may be used simultaneously. In some implementations, the venous cannula system 400 depicted within FIGS. 3 and 4 may represent two ends of the same cannula system 400.

In some embodiments, the venous cannula system 400 may contain a dual cannula 470. In some aspects, the dual cannula 470 may possess a reinfusion cannula 474 and a drainage cannula 472, as a nonlimiting list. In some implementations, the reinfusion cannula 474 may release oxygenated blood to an isolated area, wherein a balloon cuff 430 may segment off the area to prevent or limit mixing when inflated. In some embodiments, a fluids tube 423 may be embedded within the reinfusion cannula 474 to facilitate additional IV fluids or IV medication administration within the oxygenated region. In some implementations, the fluids tube 423 may be the distal end of the fluids port 322 referenced in FIG. 3.

In some aspects, a balloon cuff 430 may possess a small cavity along the exterior of the balloon cuff to allow the oxygenated blood to be released from the reinfusion cannula 474. For example, the cannula system 400 may be inserted near the heart and the balloon cuff may inflate to restrict deoxygenated blood flow from both sides of the veins (SVC and IVC) flowing into the heart while oxygenated blood and IV fluids are injected into the heart from the reinfusion cannula. This configuration may prevent or limit risk of occlusion; the mixing of oxygenated and deoxygenated blood may be prevented by the boundary formed by the balloon cuff. In some embodiments, there may be a plurality of balloon cuffs 430 of uniform or varying sizes, shapes, and biocompatible materials. The plurality of balloon cuffs 430 may spiral around the cannula system 400 or be positioned on the surface of the cannula system 400, either on a particular side or in a non-limiting arrangement or pattern around or along the device.

In some implementations, the balloon cuff tube 431 may inflate the balloon cuff from within the dual cannula 470 to reduce the required diameter for inserting the cannula system 400. In some embodiments, there may be a plurality of balloon cuffs 430 coupled to the balloon cuff tube 431. The plurality of balloon cuffs 430 may inflate to differing volumes to accommodate a desired positioning within the vessel or a particular vessel. In some aspects, the insertion mechanism 450 may allow for placing the dual cannula 470 in a position that the balloon cuff restricts movement from one or both sides of the intended vessel. In some implementations, the insertion mechanism 450 may be inserted via a separate channel as illustrated in FIG. 3. This channel may be embedded within the drainage cannula 472. Embedding channels within the dual cannula 470 may allow one or more substances to interface with the body while maintaining the same required insertion diameter for the dual cannula 470.

Maintaining the same diameter may reduce recovery time and damage to surrounding tissue, as non-limiting examples. In some embodiments, the cannula system 400 may possess a plurality of openings that operate as a cannula flow mechanism 440, 442. This may allow deoxygenated blood to enter the drainage cannula with limited to no mixing with the oxygenated blood flowed through a separate cannula. In some implementations, the cannula flow mechanism may extract deoxygenated blood from anterior and superior openings in relation to the balloon cuff 430.

As an illustrative example, the cannula system 400 may be inserted into the either superior or inferior vena cava of a patient. When inflated, the balloon cuff 430 may limit access of the drainage cannula 472 to the superior and inferior vena cava. Access to the reinfusion cannula 474 may be limited to the heart. This separation of access may limit risk of mixing, allowing for a more effective and efficient exchange of blood during ECMO. In some aspects the drainage cannula 472 may comprise a superior vena cava flow mechanism 440 and an inferior vena cava flow mechanism 442, which may allow for collection of deoxygenated blood from both locations.

Figure 5A:
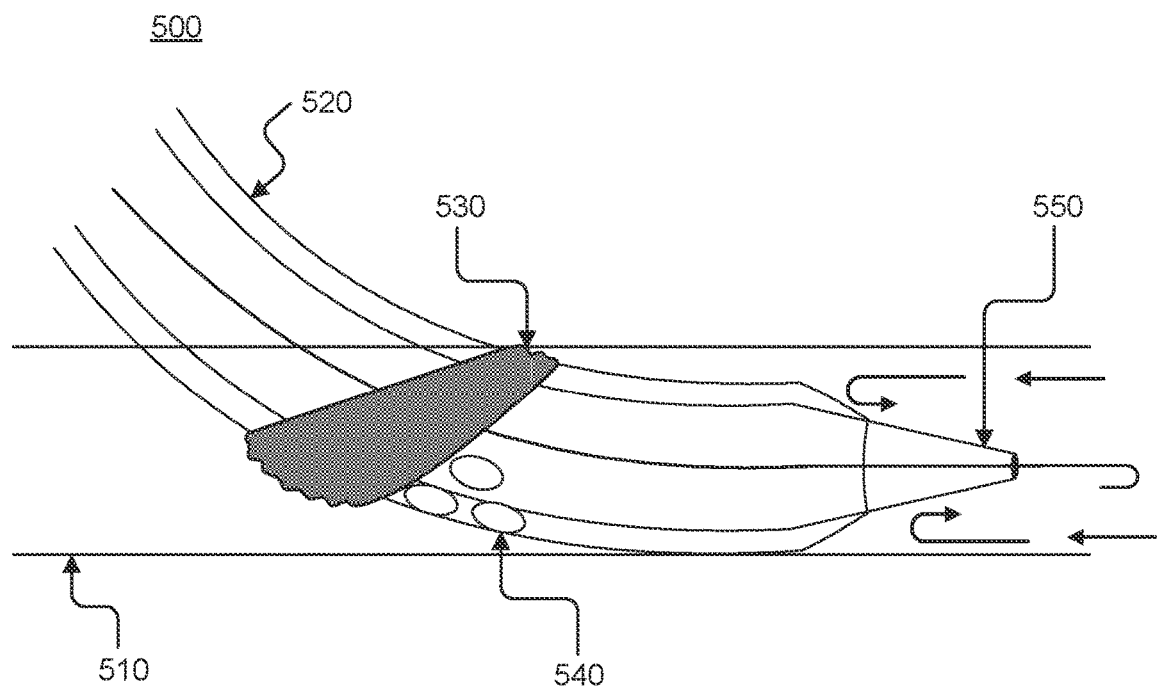
FIG. 5A illustrates an exemplary arterial cannula system, according to some embodiments of the present disclosure.
Figure 5B:
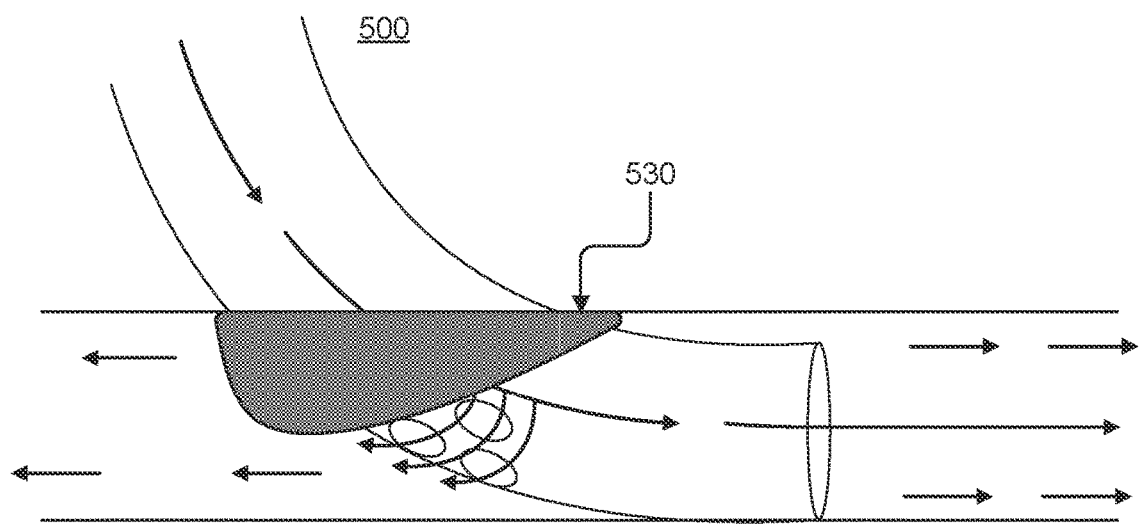
FIG. 5B illustrates an exemplary arterial cannula system, according to some embodiments of the present disclosure.

Referring now to FIG. 5A-5B, an exemplary arterial cannula system 500 is illustrated, wherein the cannula system 500 comprises a cannula 520 and balloon cuff 530. In some embodiments, the cannula 520 may be inserted into a blood vessel 510. The cannula 520 may utilize an insertion mechanism 550 to penetrate the blood vessel 510, allowing for gradual dilation of the vessel 510. In some aspects, the insertion mechanism 550 may be removed. For example, the insertion mechanism may be utilized to enter the blood vessel and removed when the cannula is secured within the blood vessel by the balloon cuff 530. Securing the cannula within the blood vessel by the balloon cuff 530 may aid in the prevention of distal occlusion during treatment.

In some aspects, the cannula 520 may comprise a balloon cuff 530 positioned before a cannula flow mechanism 540. A balloon cuff 530 may allow for secure and dependable positioning of the cannula 520 within the vessel 510. For example, if the cannula 520 was inserted into the femoral artery, the balloon cuff 530 may prevent occlusion by aligning the flow mechanism 540 distal artery, decreasing the serious risk of loss of circulation in the lower leg. The balloon cuff 530 may wrap around the cannula 520 or be positioned on any portion of the surface, such as a particular side of the cannula 520.

The cannula 520 may be inserted into a blood vessel 510 at least as far as the balloon cuff 530. Once in the cannula 520 is advanced into the vessel 510, the balloon cuff 530 may be inflated, which may allow the cannula 520 to be pulled back until the balloon cuff 530 exerts sufficient force on the side walls of the vessel 510 to ensure the correct position and orientation of the cannula flow mechanism 540. Positioning of the cannula flow mechanism 540 is crucial to proper treatment and patient safety to allow blood flow into distal artery. In some implementations, the cannula 520 may comprise more than one balloon cuff 530.

In some aspects, a balloon cuff 530 may ensure the cannula flow mechanism 540 is free of obstruction and secure within the blood vessel 510. Placement of the cannula flow mechanism 540 outside the blood vessel 510 may result in blood loss. Blocked cannula flow mechanism 540 limit the effectiveness of the cannula 520, blocking blood flow or reducing flow capacity, which may be expected with a traditional cannula.

Regulated blood flow via the cannula flow mechanism 540 reduces occlusion, which otherwise may prevent the flow of oxygenated blood to the region of the body subjected to the arterial cannula system. Occlusion is largely due to the size of the cannula preventing blood flow within the blood vessel. A cannula flow mechanism 540 may reduce risk of occlusion, which may prevent free flow of blood within the blood vessel 510. In a short amount of time, preventing oxygenated blood from reaching a portion of the body may cause ischemia and severe damage to the surrounding tissues and organs.

Figure 6A:
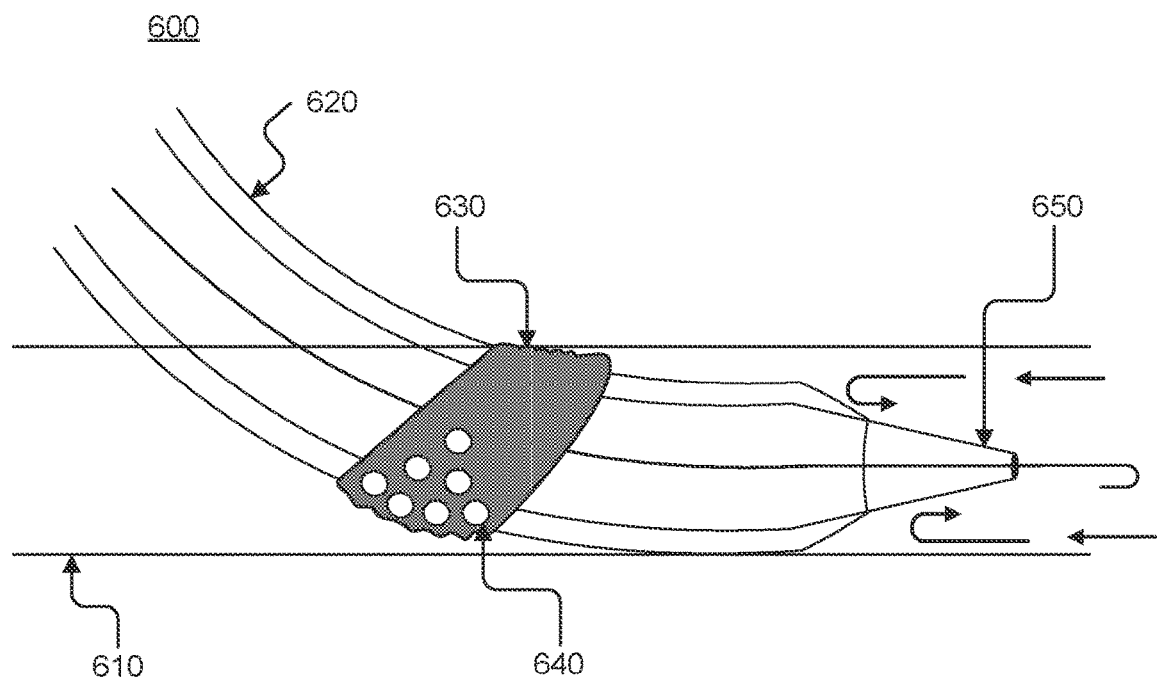
FIG. 6A illustrates an exemplary arterial cannula system, according to some embodiments of the present disclosure.
Figure 6B:
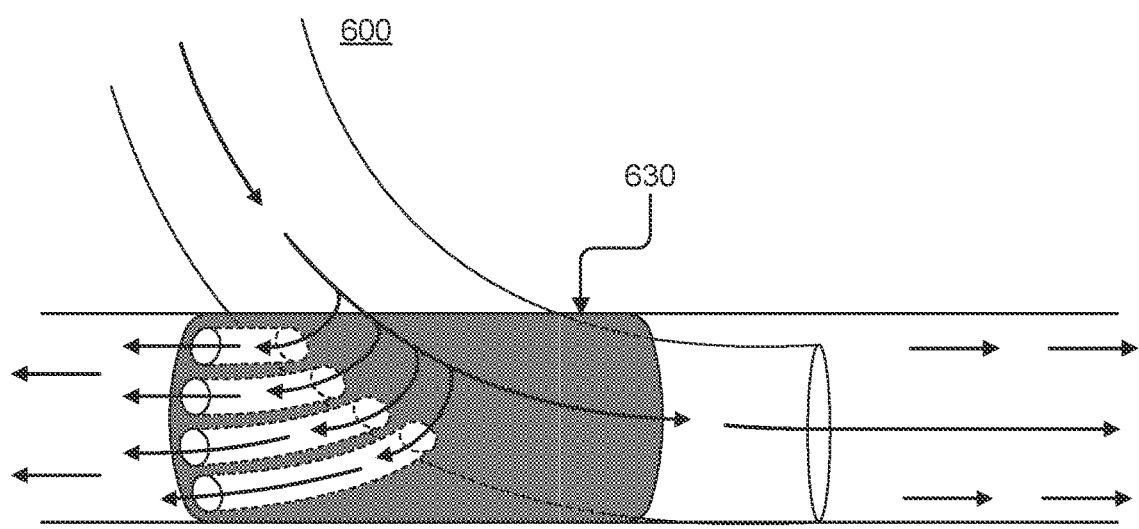
FIG. 6B illustrates an exemplary arterial cannula system, according to some embodiments of the present disclosure.
Figure 7A:
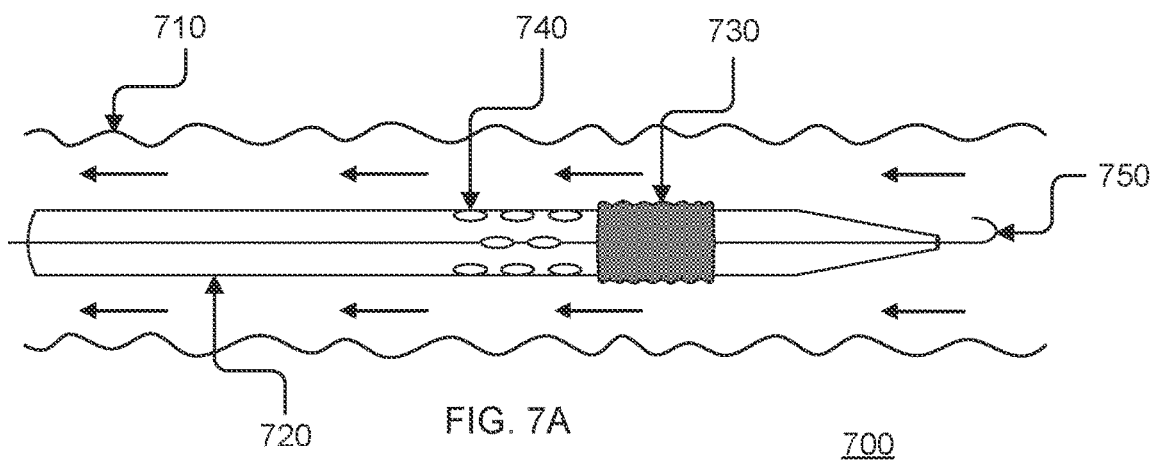
FIG. 7A illustrates an exemplary cannula system with a balloon adapter, according to some embodiments of the present disclosure.
Figure 7B:
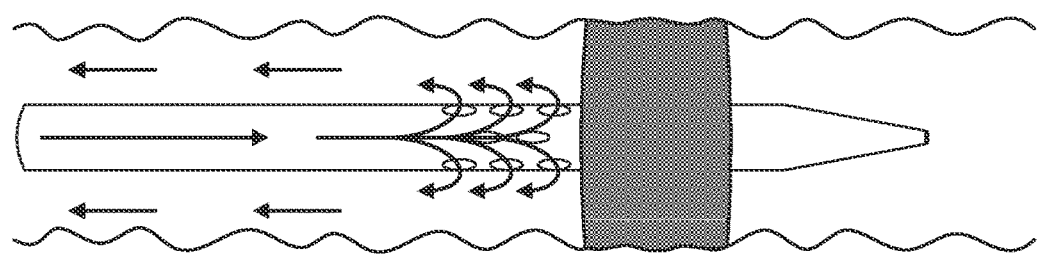
FIG. 7B illustrates an exemplary cannula system with a balloon adapter, according to some embodiments of the present disclosure.
Figure 7C:
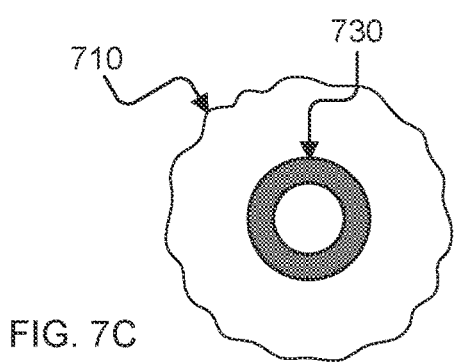
FIG. 7C illustrates an exemplary cannula system with a balloon adapter, according to some embodiments of the present disclosure.
Figure 7D:
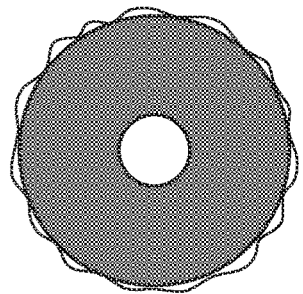
FIG. 7D illustrates an exemplary cannula system with a balloon adapter, according to some embodiments of the present disclosure.
Figure 7E:
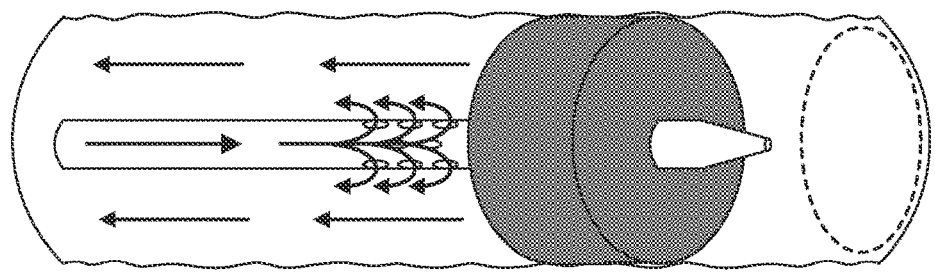
FIG. 7E illustrates an exemplary cannula system with a balloon adapter, according to some embodiments of the present disclosure.
Figure 8A:
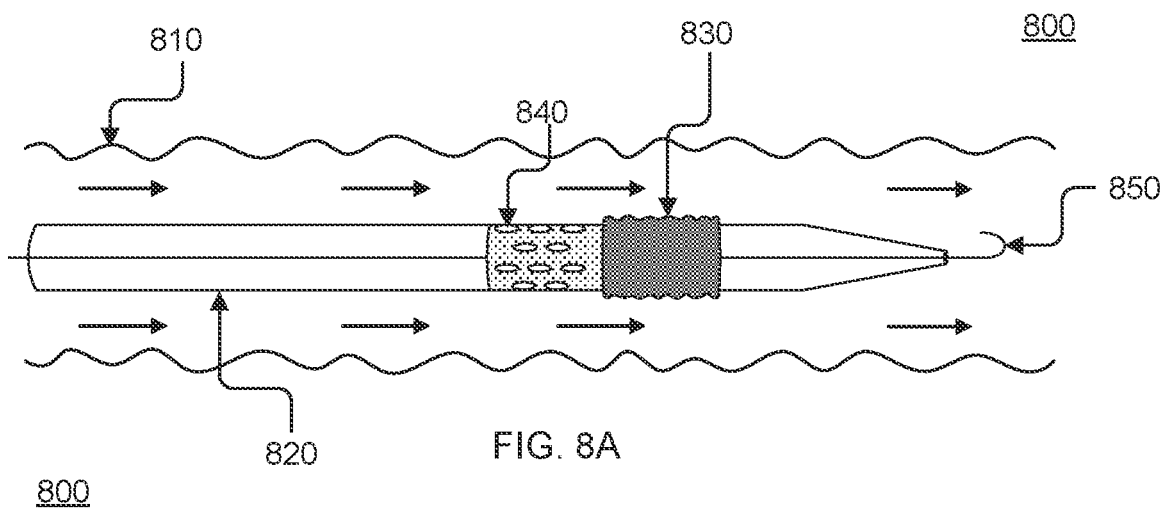
FIG. 8A illustrates an exemplary cannula system with a balloon cuff, according to some embodiments of the present disclosure.
Figure 8B:
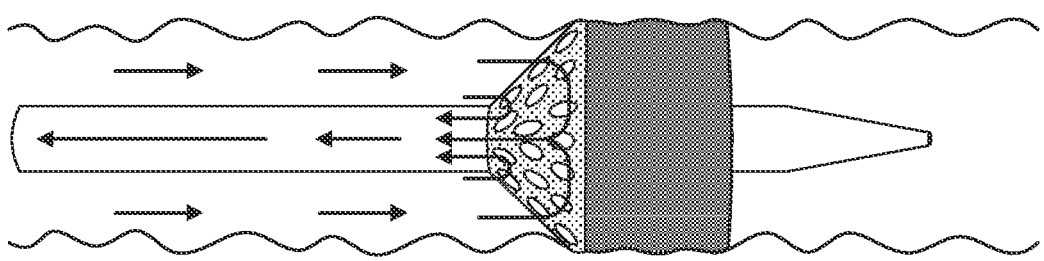
FIG. 8B illustrates an exemplary cannula system with a balloon cuff, according to some embodiments of the present disclosure.
Figure 8C:
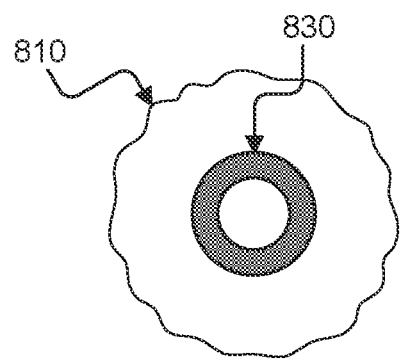
FIG. 8C illustrates an exemplary cannula system with a balloon cuff, according to some embodiments of the present disclosure.
Figure 8D:
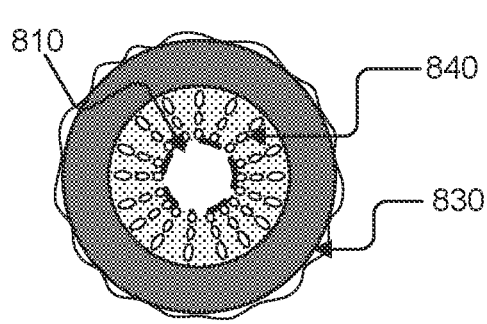
FIG. 8D illustrates an exemplary cannula system with a balloon cuff, according to some embodiments of the present disclosure.
Figure 8E:
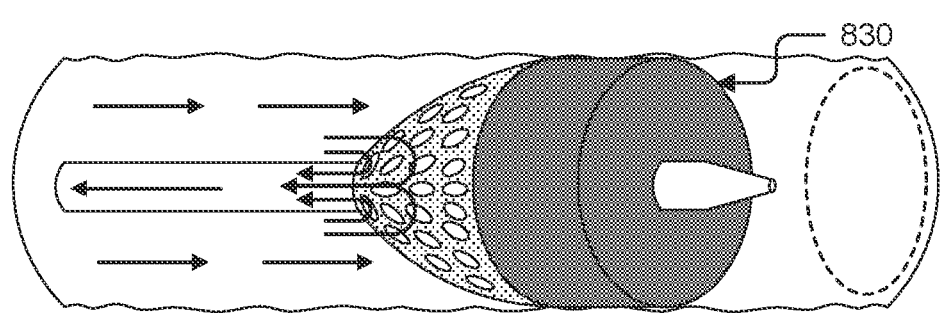
FIG. 8E illustrates an exemplary cannula system with a balloon cuff, according to some embodiments of the present disclosure.
Figure 9A:
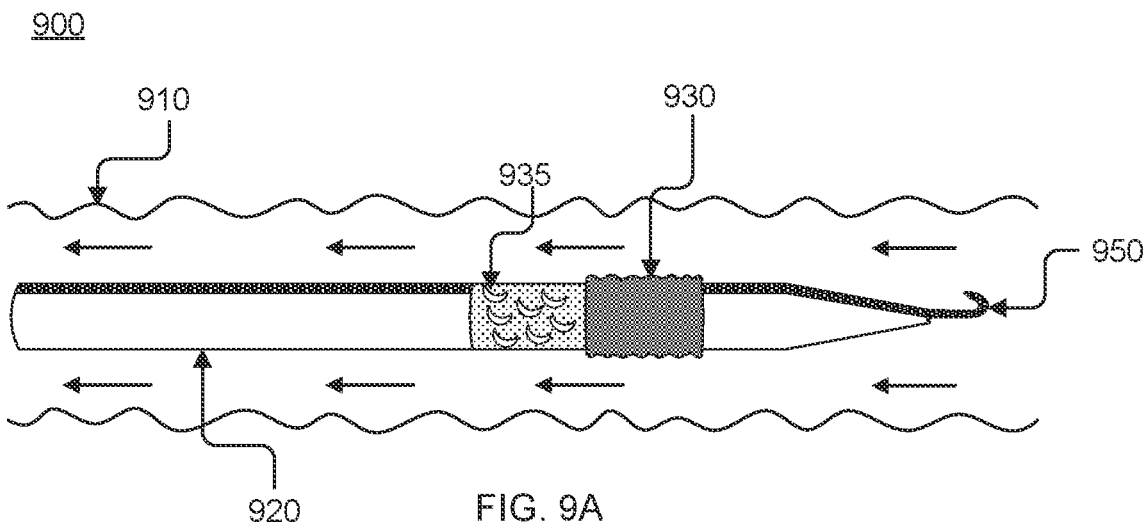
FIG. 9A illustrates an exemplary cannula system with a balloon cuff, according to some embodiments of the present disclosure.
Figure 9B:
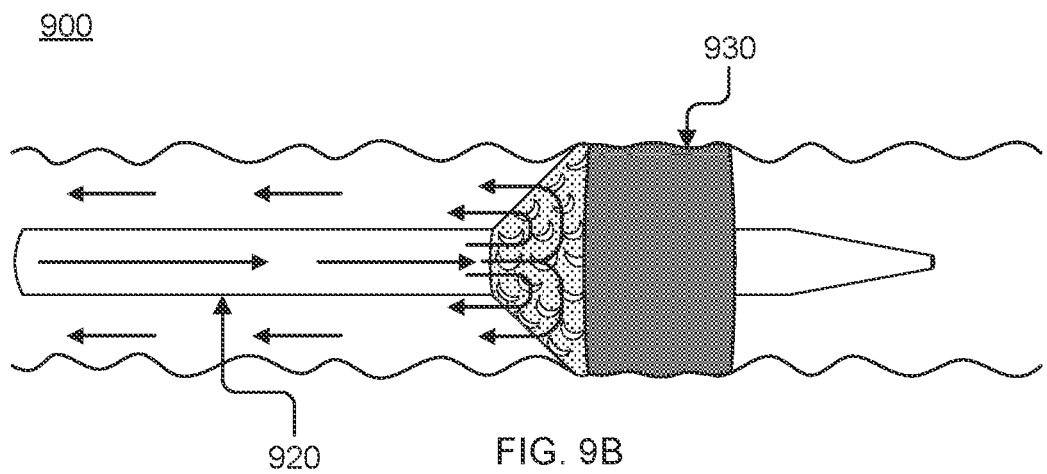
FIG. 9B illustrates an exemplary cannula system with a balloon cuff, according to some embodiments of the present disclosure.
Figure 9C:
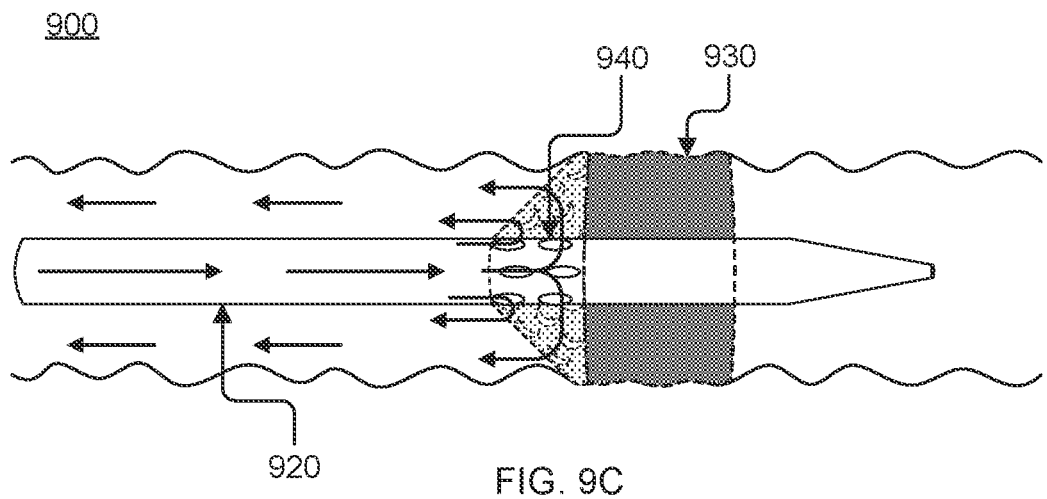
FIG. 9C illustrates an exemplary cannula system with a balloon cuff, according to some embodiments of the present disclosure.
Figure 9D:
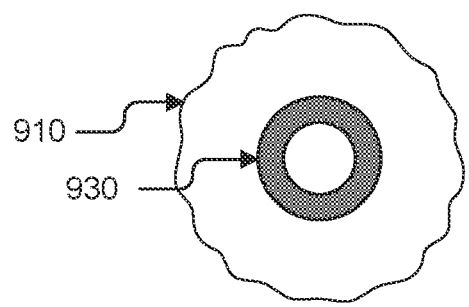
FIG. 9D illustrates an exemplary cannula system with a balloon cuff, according to some embodiments of the present disclosure.
Figure 9E:
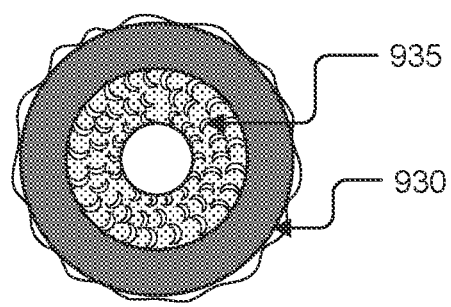
FIG. 9E illustrates an exemplary cannula system with a balloon cuff, according to some embodiments of the present disclosure.
Figure 9F:
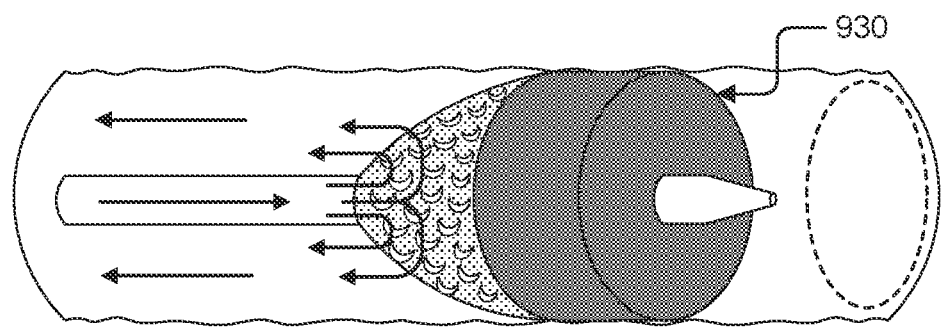
FIG. 9F illustrates an exemplary cannula system with a balloon cuff, according to some embodiments of the present disclosure.

Referring now to FIGS. 6A-6B, an exemplary arterial or reinfusion cannula system 600 is illustrated. In some embodiments, the cannula system 600 may be inserted into a blood vessel 610. In some implementations, the cannula 620 may be inserted via an insertion mechanism 650. In some aspects, the cannula 620 may comprise a balloon cuff 630. In some embodiments, the balloon cuff 630 may comprise a cannula flow mechanism 640.

In some embodiments, blood may be able to flow through the balloon cuff 630. For example, the balloon cuff 630 may not just ensure proper positioning within the vessel. The balloon cuff 630 may also facilitate blood flow through an integrated cannula flow mechanism 640. In some aspects, the cannula flow mechanism 640 may comprise a plurality of pores 642 or openings, arranged generally or specifically to accommodate a desired blood vessel, such as one that may have a higher, faster blood flow. The cannula flow mechanism 640 may be coupled to channels housed within the balloon cuff 630 connecting to the interior of the cannula 620. The channels may allow for proper blood flow diversion by the exemplary cannula system 600.

Referring now to FIGS. 7A-7E, an exemplary venous cannula system 700 is illustrated. In some implementations, the cannula 720 may be inserted into the blood vessel 710 in an orientation parallel to blood flow. In some aspects, the cannula 720 may comprise balloon cuff 730, insertion mechanism 750, and cannula flow mechanism 740. In some embodiments, the cannula 720 may possess an insertion mechanism 750 to orient the cannula 720 within the blood vessel 710. In some implementations, the balloon cuff 730 and cannula flow mechanism 740 may be embedded within the structure of the cannula 720. For example, the balloon cuff 730 may be welded into the walls of the cannula 720. In some aspects, the balloon cuff 730 may be adhered or coupled to the cannula 720.

In some embodiments, the balloon cuff 730 may be expanded to control blood flow within the blood vessel 710. For example, the balloon cuff 730 may be expanded to restrict the flow of deoxygenated blood and inject oxygenated blood into the blood stream, wherein restriction may limit mixing. Mixing may be an issue when collection of deoxygenated blood and injection of oxygenated blood occurs in proximate locations within the body. In some aspects, the cannula flow mechanism 740 may supply blood into the blood vessel 710 from the structure of the cannula 720. The cannula flow mechanism 740 may be placed in any position that allows the balloon cuff 730, when inflated, to prevent the mixing of deoxygenated and oxygenated blood. In some embodiments, there may be more than one balloon cuff 730.

Referring now to FIGS. 8A-8E, an exemplary cannula system 800 with a balloon cuff 830 is illustrated. In some aspects, the cannula system 800 may be positioned within the blood vessel 810 via an insertion mechanism 850, parallel and in the direction of blood flow. In some embodiments, the cannula 820 may comprise a balloon cuff 830. In some implementations, the balloon cuff 830 may comprise a cannula flow mechanism 840. The balloon cuff 830 may be arranged around the cannula 820 near the insertion mechanism 850 end. In some embodiments, the balloon cuff 830 may have a blunt end that, when inflated, completely blocks blood flow, forcing blood to flow into the cannula 820.

For example, the cannula flow mechanism 840 may supply blood into the cannula 820 from the blood vessel 810 from a position coupled to the structure of the cannula 820 and the balloon cuff 830. For example, the cannula flow mechanism 840 may comprise a flexible, porous material that transitions from a restricted first position to an expanded second position when the balloon cuff 830 is inflated. The porous material may contain a plurality of pores 842 coupled to the interior of the vessel 810 on one end and the interior of the cannula 820 on an opposite end. The plurality of pores 842 may facilitate deoxygenated blood flow from the vessel 810 into the cannula 820 for treatment. In some embodiments, there may be more than one balloon cuff 830.

Referring now to FIGS. 9A-9F, an exemplary cannula system with cannula adapter is illustrated. In some aspects, the cannula system 900 may be positioned within the blood vessel 910 via an insertion mechanism 950 parallel to and in a direction opposing blood flow. In some embodiments, the cannula 920 may comprise a balloon cuff 930. The balloon cuff 930 may comprise a blunt end so as to block blood flow through the vessel 910 when inflated. In some implementations, the balloon cuff may comprise a cannula flow mechanism 935.

The cannula flow mechanism 935 may comprise a plurality of pores 942 further comprising a uniform or non-limiting variety of sizes, shapes, and arrangements. The plurality of pores 942 may be coupled to channels housed in the balloon cuff 930 coupled to the interior of the cannula 920, allowing for the flow of blood from the cannula 920 to the vessel 910.

Referring now to FIG. 10A-10D, an exemplary cannula system 1000 with balloon cuff 1030 is illustrated. In some embodiments, the cannula 1020 may comprise a balloon cuff 1030. In some implementations, the balloon cuff 1030, 1032, 1034 may be adjustable. There may be one or more than one balloon cuff 1030. In some aspects, the balloon cuff 1030 may allow the cannula 1020 to be adjusted within the blood vessel 1010.

In some embodiments, the cannula flow mechanism 1040 orientation may be adjusted in relation to the balloon cuff 1030. In some implementations, an adapter mechanism 1035 may be utilized to facilitate fluid flow when the cannula flow mechanism 1040 and the balloon cuff 1030 occupy the same location on the cannula 1020. An adjustable balloon cuff 1030, 1032, 1034 may allow for partial or total overlap of the cannula flow mechanism 1040, allowing for restriction or allowance of a particular quantity of blood flow through the cannula 1020.

Referring now to FIG. 11, an exemplary cannula system 1100 is illustrated. In some embodiments, a plurality cannula 1120, 1125 may attach via fitted connection. In some implementations, the cannula 1120 may comprise a cannula flow mechanism 1140. In some aspects, a cannula 1120 may comprise a balloon cuff 1130. The fitted connection may allow for integration of cannula 1120 with pre-existing cannulae not specified in this application.

Referring now to FIG. 12, an exemplary cannula system 1200 is illustrated. In some embodiments, a plurality cannula 1220, 1225 may attach via an adapter mechanism 1215. In some implementations, the cannula 1220 may comprise a cannula flow mechanism 1240. In some aspects, a cannula 1220 may comprise a balloon cuff 1230. The balloon cuff 1230 may be fixed in a position, either wrapped around the cannula 1220 or coupled to a side, or adjustable.

For example, the adapter mechanism 1215 may comprise an inner circumference and an outer circumference. In some embodiments, the inner circumference may be coupled to the interior walls of the cannula 1220, so that an end of the inner circumference and an end of the cannula 1220 seamlessly align. The outer circumference may be coupled to the outer surface of the cannula 1220 on the same end as the inner circumference, creating a space the circumference of the cannula 1225 may insert into, either by sliding in or snapping into place, as non-limiting examples. When the cannula 1225 is inserted into the adaptor mechanism 1215, the two pieces may be held together, so as to allow for proper, secure functioning of the cannula 1220.

Figure 13A:
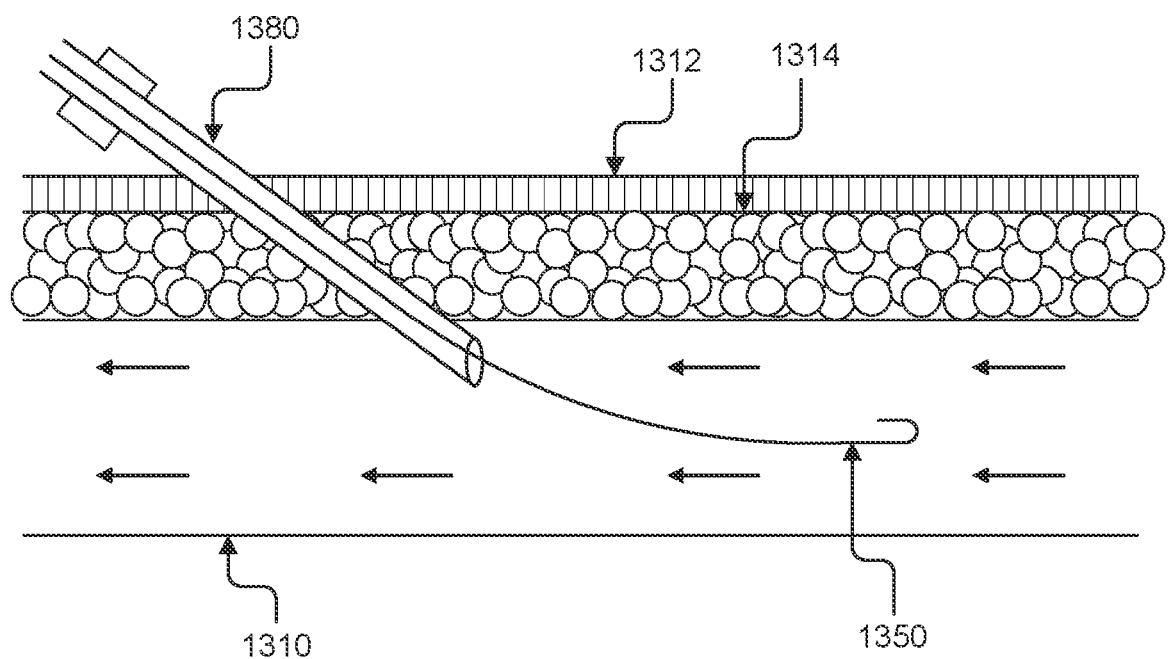
FIG. 13A illustrates an exemplary insertion step for a cannula system, according to some embodiments of the present disclosure.
Figure 13B:
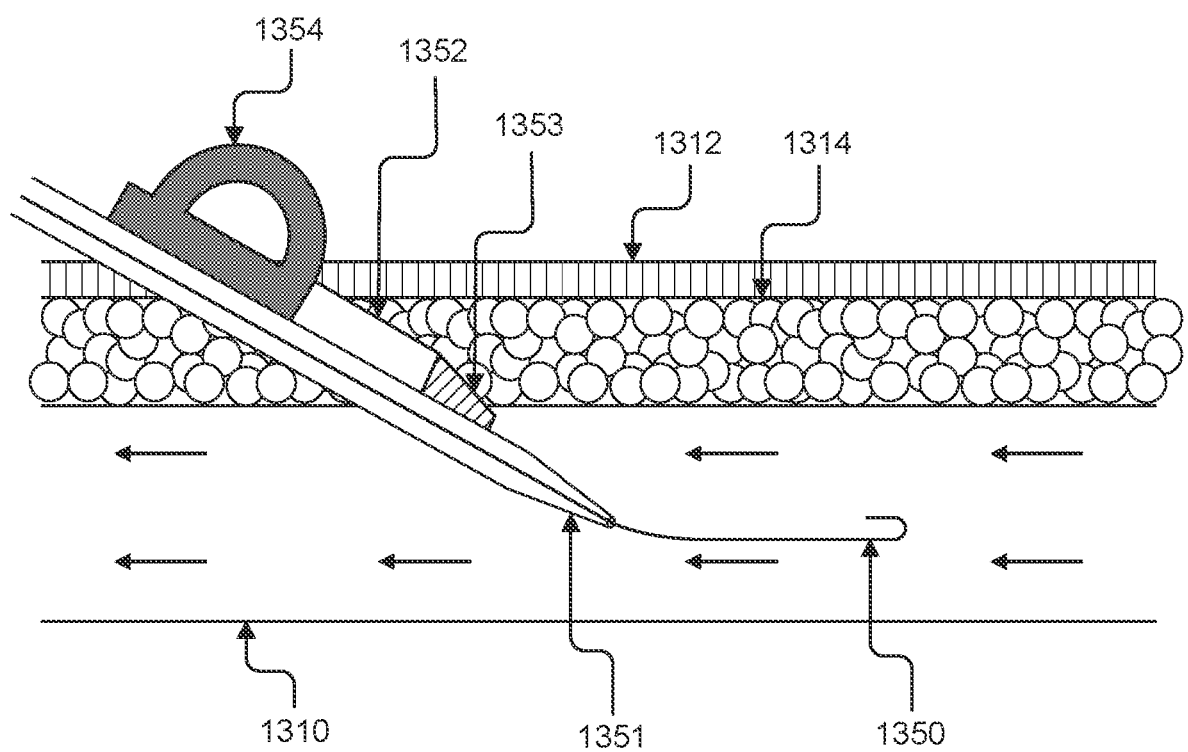
FIG. 13B illustrates an exemplary insertion step for a cannula system, according to some embodiments of the present disclosure.

Referring now to FIGS. 13A-13C, exemplary insertion steps for a cannula system is illustrated. In some embodiments, an insertion needle 1380 may penetrate the skin 1312 and tissue 1314 to enter the bloodstream of the intended blood vessel 1310. In some implementations, the insertion needle 1380 may place an insertion mechanism 1350 into the blood vessel, wherein the insertion mechanism 1350 may assist in placement of the cannula system. For example, an insertion needle 1380 may contain an insertion mechanism 1350 comprising a wire that may guide a cannula system into placement within the blood vessel 1310. After the wire is inserted into the blood vessel 1310 via the center of the insertion needle 1380, the insertion needle 1380 may be extracted while the wire remains to guide the subsequent insertion of the cannula system.

In some embodiments, the insertion mechanism 1350 may guide a dilator 1352 into the blood vessel 1310. In some implementations, a dilator tube 1351 may be connected or threaded with the insertion mechanism 1350, which may assist in positioning the dilator 1352. In some aspects, the dilator tube 1351 may be connected to a dilator razor 1353 that may dilate by penetrating the skin 1312, tissue 1314, and blood vessel 1310. In some implementations, a dilator 1352 may be attached to the insertion mechanism 1350 to increase the diameter of the point of insertion so that it is sufficient to insert the cannula system.

This may allow for safe insertion of a cannula system into the blood vessel 1310. In some embodiments, the depth of incision caused by the dilator tip 1353 may be limited by a dilator handle 1354. The dilator handle 1354 may be located on the dilator 1352 so that the dilator tip 1353 may only penetrate to a safe and effective distance into the blood vessel 1310.

In some aspects, the dilator 1352 may possess an anterior dilator tip 1353, 1356 that allows the diameter of the incision to increase. In some embodiments, the dilator tip 1353, 1356 may possess the sharpness of a sharp to allow the dilator 1352 to increase the diameter of the insertion location. The incorporation of a knife edge to the dilator tip 1353, 1356 may allow the dilation of the insertion to the precise diameter of the cannula without forming a skin bridge. In some aspects, the sharp edge may extend beyond the dilator tip 1356 to the length of the dilator 1352. In some implementations, the dilator 1352 may possess a dilator handle 1354 to prevent the dilator tip 1353, 1356 from proceeding too deep within the blood vessel 1310.

Figure 14A:
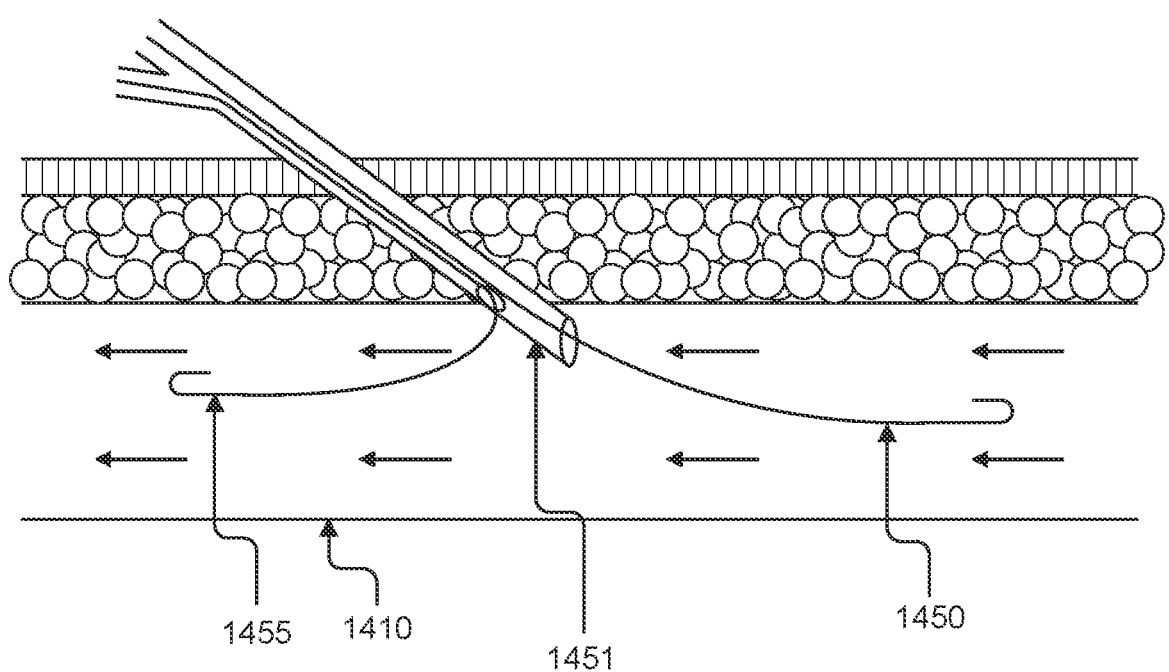
FIG. 14A illustrates an exemplary insertion step, according to some embodiments of the present disclosure.
Figure 14B:
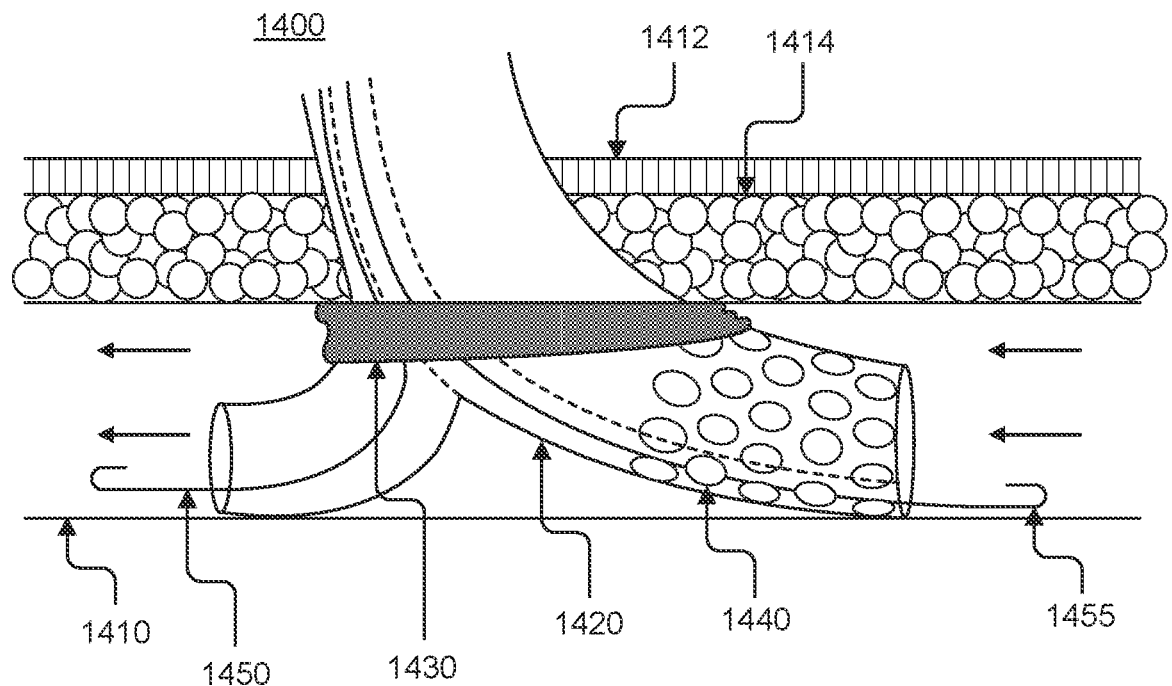
FIG. 14B illustrates an exemplary insertion step, according to some embodiments of the present disclosure.
Figure 14C:
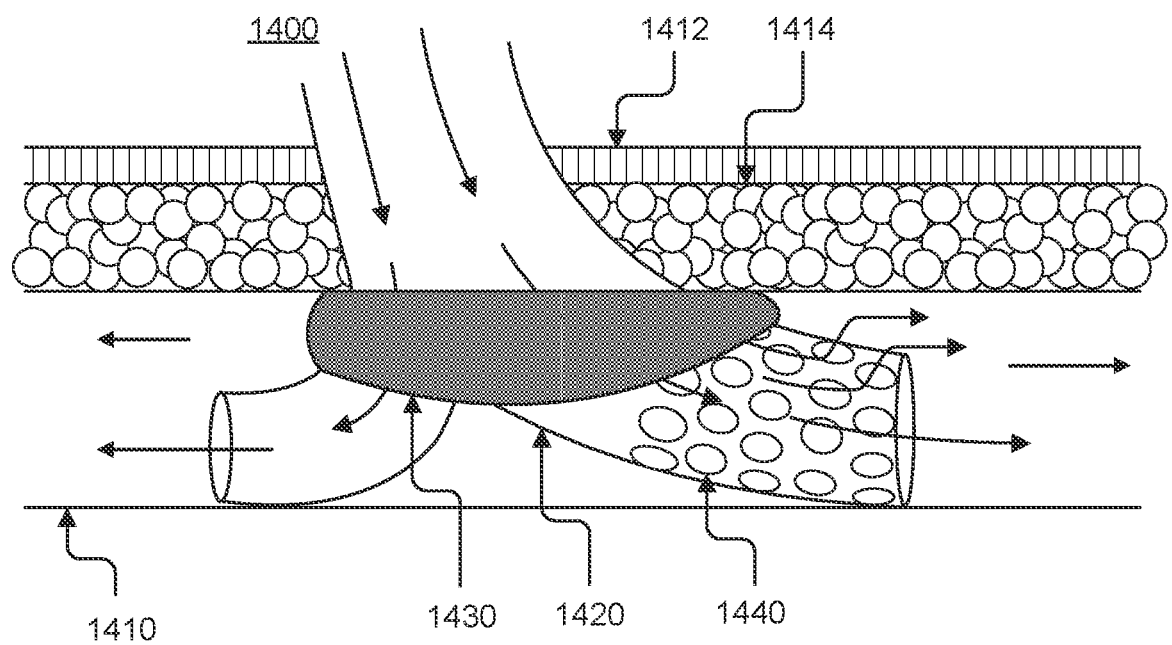
FIG. 14C illustrates an exemplary insertion step, according to some embodiments of the present disclosure.

Referring now to FIG. 14A-14C, insertion steps for an exemplary cannula system 1400 are illustrated. As illustrated in FIG. 14A, in some embodiments an insertion needle 1480 may assist in positioning the insertion mechanism 1450. In some implementations, the insertion needle 1480 may comprise a double lumen needle. In some aspects, the insertion needle 1480 may penetrate the skin 1412, tissue 1414, and blood vessel 1410 to place the insertion mechanism 1450 within the blood vessel 1410. In some implementations, the insertion needle 1480 may allow for the insertion of a plurality of insertion mechanisms 1450. In some aspects, a plurality of insertion mechanisms 1450 may be inserted into the blood vessel 1410 in a plurality of orientations depending on the size and type of blood vessel 1410.

An as illustrative example, a hollow needle may facilitate the insertion of two insertion mechanisms 1450. The insertion mechanisms 1450 may enter the blood vessel 1410 from two openings in the insertion needle 1480. One of the insertion mechanisms 1450 may enter the blood vessel 1410 with an upstream orientation and the other insertion mechanism 1450 may enter the blood vessel 1410 with a downstream orientation with relation to blood flow. In some embodiments, the insertion mechanisms 1450, 1455 are spaced apart at least enough so they do not interfere, although this does not limit them to a particular position or orientation within the wall of the hollow needle. The insertion needle 1480 may comprise a hollow needle with partitioned segments, which may limit risk of entangling. It may allow for more independent control of each insertion mechanism 1450, 1455.

Referring now to FIGS. 14B-14C, insertion steps for an exemplary arterial cannula system 1400 are illustrated. In some embodiments, the cannula system 1400 may comprise dual cannula 1420, which may comprise separate cannula 1420, a cannula 1420 with separated segments, or cannula 1420 with shared flow that terminates in multiple directions, as non-limiting examples. In some implementations, the cannula system 1400 may be used in venous applications. In some aspects, the orientation of the cannula 1420 within the blood vessel 1410 may be defined by the insertion path provided by the insertion mechanism 1450.

In some implementations, a plurality of cannula 1420 may flow in the same direction while placed in a variety of orientation within the blood vessel 1410. For example, the cannula system 1400 may utilize two cannula 1420 that provide oxygenated blood into the blood vessel 1410. Within the blood vessel 1410, one cannula 1420 may provide oxygenated blood in the upstream region of the insertion site of the cannula system 1400 and the other cannula 1420 may provide oxygenated blood to the downstream region of the insertion site of the blood vessel 1410. This may prevent occlusion by providing oxygenated blood to both divided regions of the blood vessel 1410.

In some aspects, a balloon cuff 1430 may inflate within the blood vessel 1410 to provide stability to the cannula system 1400. This would ensure intentional placement of the cannula system 1400 remains in a fixed state for the duration of the insertion. In some embodiments, the cannula system 1400 may possess a cannula flow mechanism 1440 that may comprise openings that allow free flow of fluid through the cannula 1420. This cannula flow mechanism 1440 may be separate or integrated with the balloon cuff 1430. In some implementations, the tip of the cannula 1420 may taper towards the insertion mechanism 1455.

In some implementations, the cannula flow mechanism 1440 may exist as a passive form of fluid flow to prevent occlusion within the blood vessel 1410. In some aspects, the cannula flow mechanism 1440 may exist as shapes within the wall of the cannula 1420. These shapes may be uniform or vary according to a pattern or randomly, as non-limiting examples. In some embodiments, the cannula flow mechanism 1440 may comprise configurations that reduce the amount of drag and vorticity generated from the insertion of the cannula system 1400.

In some embodiments, the cannula flow mechanism 1440 may allow for an even distribution and extraction of blood from the blood vessel 1410 to reduce pressure differentials within the blood vessel 1410. In some implementations, the insertion mechanism 1450 may be removed. For example, the balloon cuff 1430 may be inflated and provide stability to the cannula 1420. After the cannula 1420 is fixed in the desired orientation, the insertion mechanism 1450 may be removed.

Figure 15:
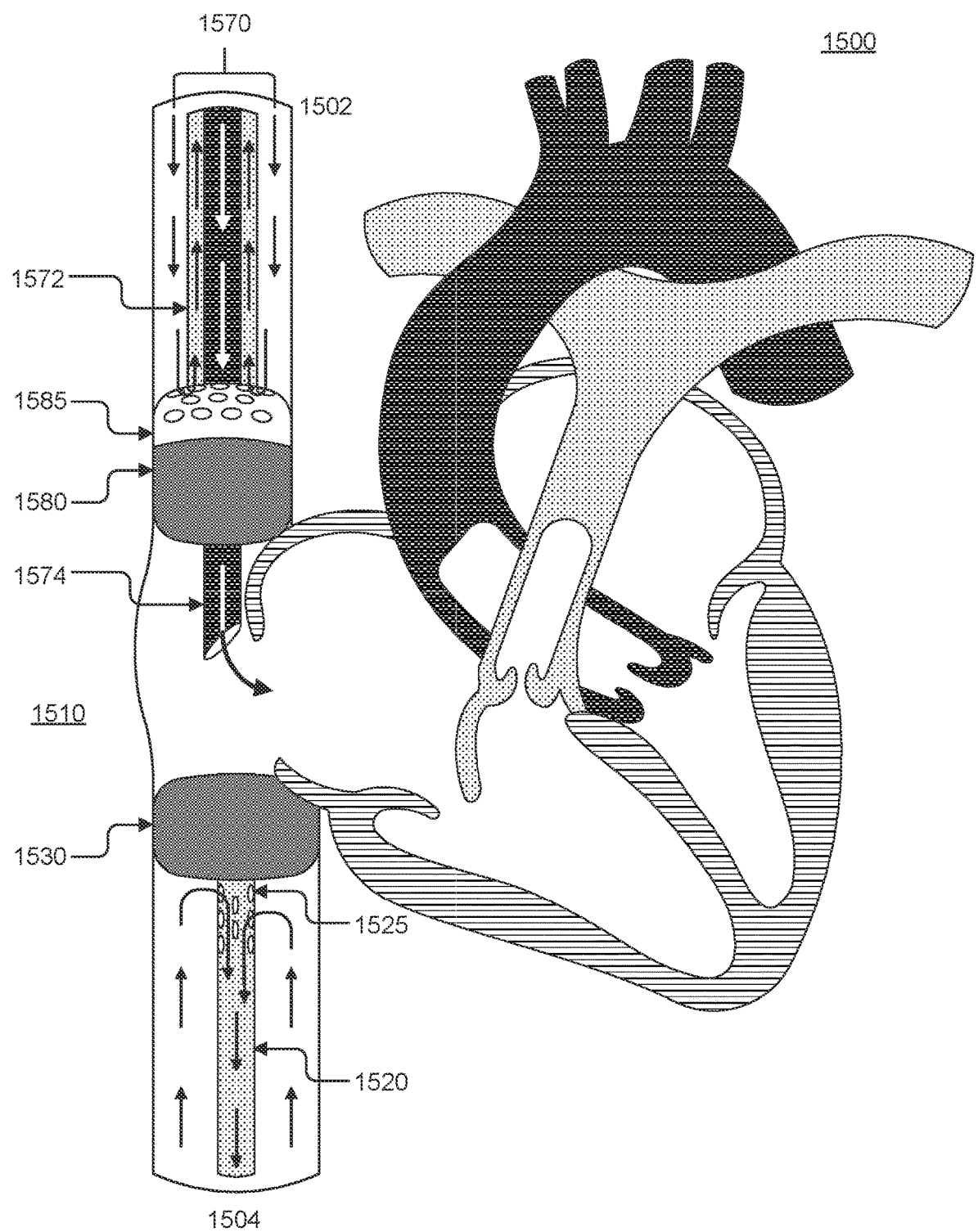
FIG. 15 illustrates an exemplary heart with cannula system, according to some embodiments of the present disclosure.

Referring now to FIG. 15, an exemplary heart 1500 with cannula system 1510 is illustrated. In some aspects, a cannula system 1510 may comprise separate cannulas 1570, 1520, wherein each cannula 1570, 1520 may comprise balloons 1580, 1530. In some embodiments, the cannula system 1510 may include dual cannula 1570 with dual positioning balloon 1580. A dual cannula 1570 may comprise a collecting cannula 1572 for removing deoxygenated blood and a reinfusion cannula 1574. In some aspects, a reinfusion cannula 1574 may extend beyond the dual positioning balloon 1580, which may allow for flow of oxygenated blood into the heart 1500.

A dual positioning balloon 1580 may block free flow of deoxygenated blood from a superior vena cava 1502 to the heart 1500, and a single cannula balloon 1530 may block free flow of deoxygenated blood from an inferior vena cava 1504 to the heart 1500. Blocking free flow of deoxygenated blood may limit risk of mixing and recirculation, particularly when oxygenated blood is flowed into the heart 1500 through a reinfusion cannula 1574 positioned beyond the dual positioning balloon 1580. In some embodiments, dual cannula 1570 may be inserted into inferior vena cava and cannula 1504 into superior vena cava.

In some embodiments, the dual positioning balloon 1580 and single positioning balloon 1530 may block blood flow into the heart 1500, which may allow for efficient collection of deoxygenated blood from the superior vena cava 1502 and the inferior vena cava 1504, respectively. The reinfusion cannula 1574 may flow oxygenated blood into the heart 1500 with limited to no risk of mixing and recirculation of oxygenated and deoxygenated blood. For example, a cannula may only extract deoxygenated blood and another cannula within the cannula system 1510 may extract deoxygenated blood and inject oxygenated blood into a separate region. In some aspects, the balloon cuff 1530 acts as a barrier and director, ensuring the oxygenated blood from the reinfusion cannula 1574 flows into the heart 1500.

In some implementations, a cannula system 1510 may restrict blood flow in a number of regions within a blood vessel. As an illustrative example, a cannula system 1510 may be utilized in a blood vessel near the heart 1500 and multiple cannulae 1570, 1520 with balloons 1580, 1530 may be utilized to prevent deoxygenated blood from entering the heart 1500. This may occur in situations where oxygenated blood from an extracorporeal oxygenator is inserted directly into the heart 1500.

In some aspects, cannula 1570, 1520 may comprise flow mechanisms 1585, 1525, which may allow for collection of deoxygenated blood. In some implementations, a balloon flow mechanism 1585 may extend around a dual cannula 1570, where the drainage cannula 1572 may terminate before the balloon 1580 allowing for collection of deoxygenated blood. In some embodiments, balloons 1580, 1530 may control and guide positioning within the superior vena cava 1502 and inferior vena cava 1504, which may ensure the oxygenated blood is effectively provided to the heart 1500. Balloons 1580, 1530 may have a plurality of inflation circumferences, so as to accommodate blood vessels of different sizes.

Figure 16A:
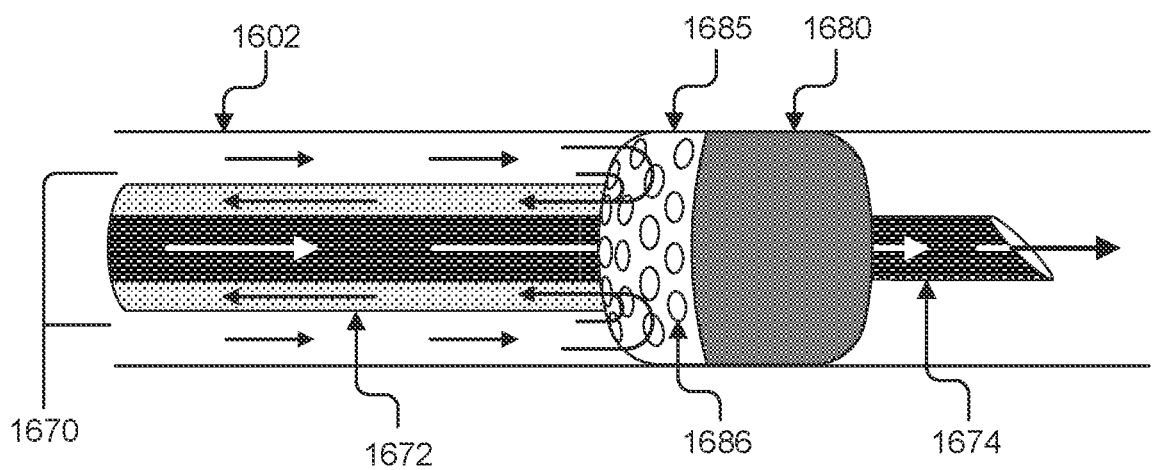
FIG. 16A illustrates an exemplary cannula system with dual cannula, according to some embodiments of the present disclosure.
Figure 16B:
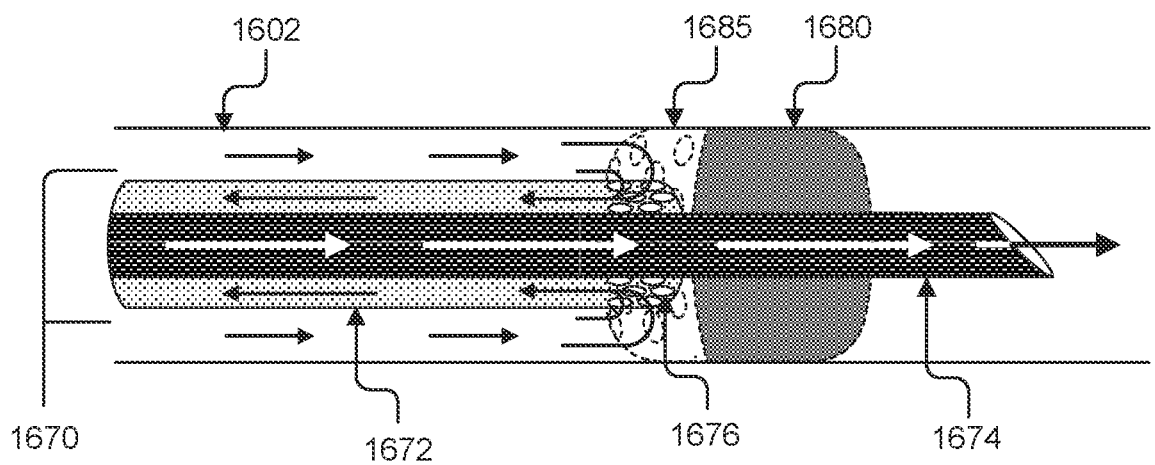
FIG. 16B illustrates an exemplary cannula system with dual cannula, according to some embodiments of the present disclosure.
Figure 16C:
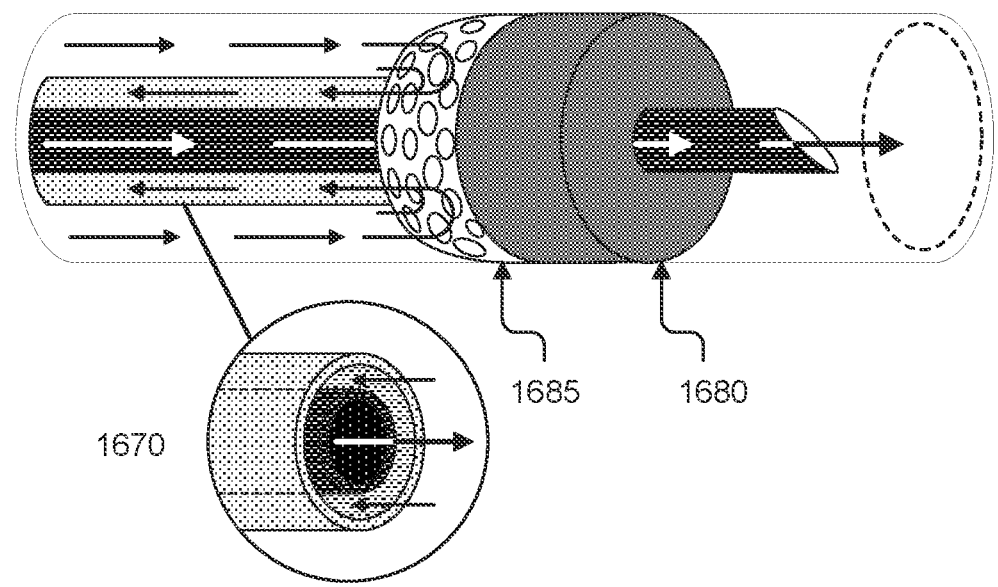
FIG. 16C illustrates an exemplary cannula system with dual cannula, according to some embodiments of the present disclosure.

Referring now to FIGS. 16A-16C, exemplary cannula system with dual cannula 1670 is illustrated. In some embodiments, the cannula 1670 may contain drainage cannula 1672 to remove deoxygenated blood and reinfusion cannula to infuse oxygenated blood. In some aspects, the cannula may be embedded within the other cannula within the dual cannula 1670. For example, the reinfusion cannula 1674 within the cannula 1670 may be embedded within the drainage cannula 1672 that extracts deoxygenated blood from the superior vena cava 1602. In this example, the two functions may be separated by at least one inflated balloon 1680.

In some embodiments, the balloon 1680 may contain a balloon flow mechanism 1685 with pores 1686. In some aspects, the side of the balloon 1680 containing the cannula flow mechanism 1685 may extract deoxygenated blood and the restriction of blood flow may allow the oxygenated blood to be released into the blood stream on the opposing side of the balloon 1680. In some implementations, the balloon 1680 may comprise a number of segments to better regulate inflation. For example, the balloon 1680 may contain a segment containing a balloon flow mechanism 1685 and a segment without a balloon flow mechanism. In some aspects, the balloon 1680 may consist of segments that may perform a variety of functions including blood collection, blood flow restriction, as a non-limiting list. The balloon 1680 may have varying inflation circumferences so as to accommodate blood vessels of varying diameters. In some embodiments, there may be a plurality of balloons 1680 for more customizable use.

Figure 17:
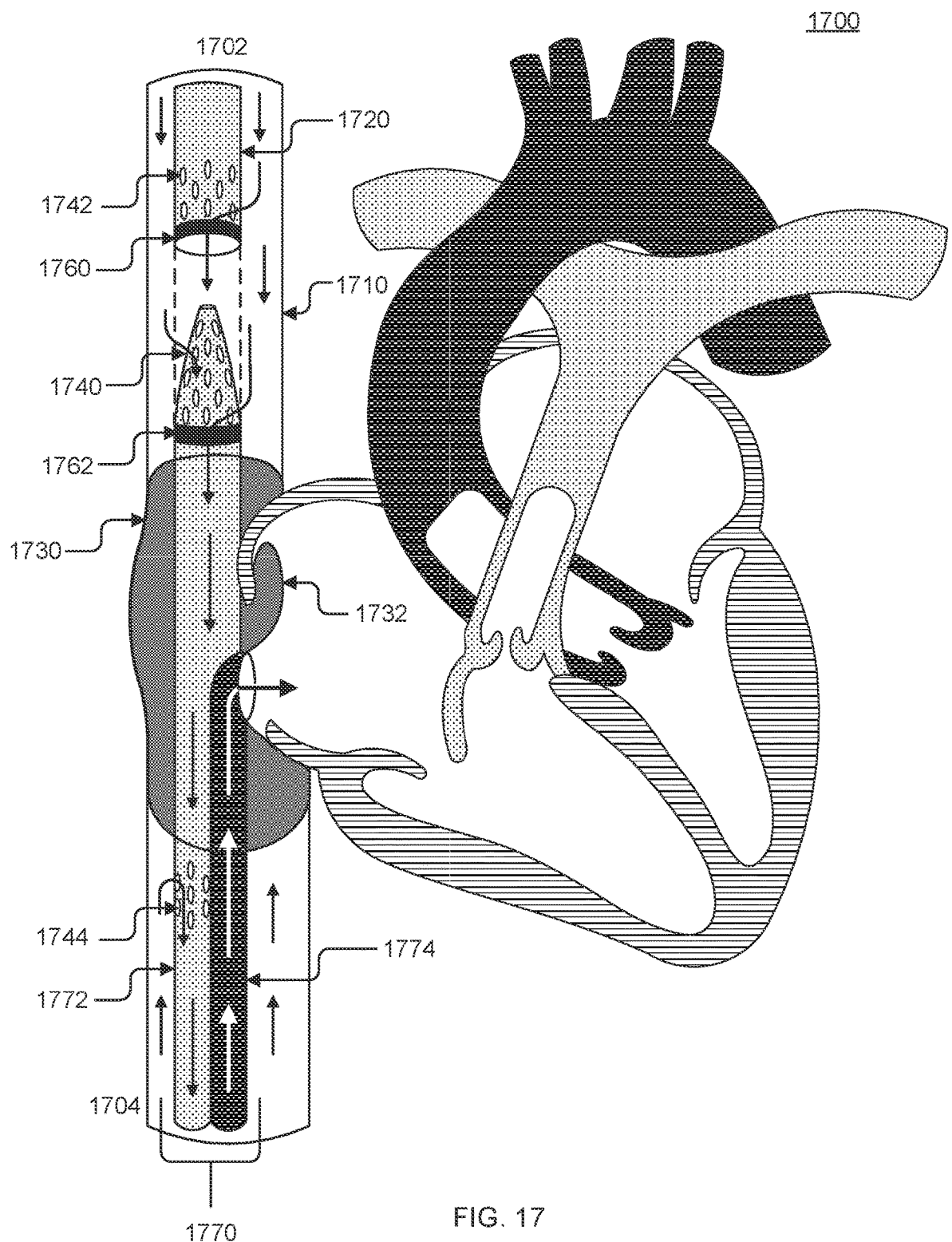
FIG. 17 illustrates a heart with an exemplary cannula system with connector mechanism, according to some embodiments of the present disclosure.

Referring now to FIG. 17, an exemplary cannula 1720 and dual cannula 1770 with connector mechanisms 1760, 1762 is illustrated. In some embodiments, the cannula 1720 and the dual cannula may attach via connector mechanisms 1760, 1762. For example, the cannula 1720 and the dual cannula 1770 may comprise an embedded magnetic strip that encircles the distal end of the cannula 1720 and the dual cannula 1770 respectively. As the cannula 1720 and the dual cannula 1770 increase in proximity, the magnetic ends attract and assist in aligning and connecting the cannula 1720 and the dual cannula 1770. In some implementations, the dual cannula 1770 may comprise at least one balloon cuff 1730.

In some aspects, the balloon cuff 1730 may comprise a positioning arm 1732. In some embodiments, the positioning arm 1732 may allow the reinfusion cannula 1774 to inject oxygenated blood directly into the heart. In some aspects, the balloon cuff 1730 may surrounding the distal end of the reinfusion cannula 1774 as it deposits blood into the heart. This separation from the blood vessel 1710 may prevent occlusion and mixing. The flow within the blood vessel 1710 may be facilitated via the drainage cannula 1772 and the associated plurality of cannula flow mechanism 1740, 1742, 1744.

In some implementations, the cannula 1720 and the dual cannula 1770 may connect in proximity to the heart. In some aspects, the cannula 1720 and the dual cannula 1770 may connect between the SVC 1702 and the IVC 1704. In some embodiments, the dual cannula 1770 may comprise a drainage cannula 1772. In some implementations, the distal end of the drainage cannula 1772 may comprise a cannula flow mechanism 1740. In some aspects, the cannula 1720 may comprise a cannula flow mechanism 1742.

In some embodiments, the blood collected via the cannula flow mechanism 1742 may enter the cannula flow mechanism 1740 of the dual cannula 1770. For example, the cannula 1720 and the dual cannula 1770 may connect via connector mechanisms 1760, 1762. The connection may cause the cannula flow mechanism of the dual cannula 1770 to become embedded within the joined cannula. The cannula flow mechanism 1740 may facilitate deoxygenated blood flow from the blood vessel 1710 that passes through the cannula flow mechanism 1742 within the joined cannula as it is extracted from the blood vessel 1710.

Figure 18:
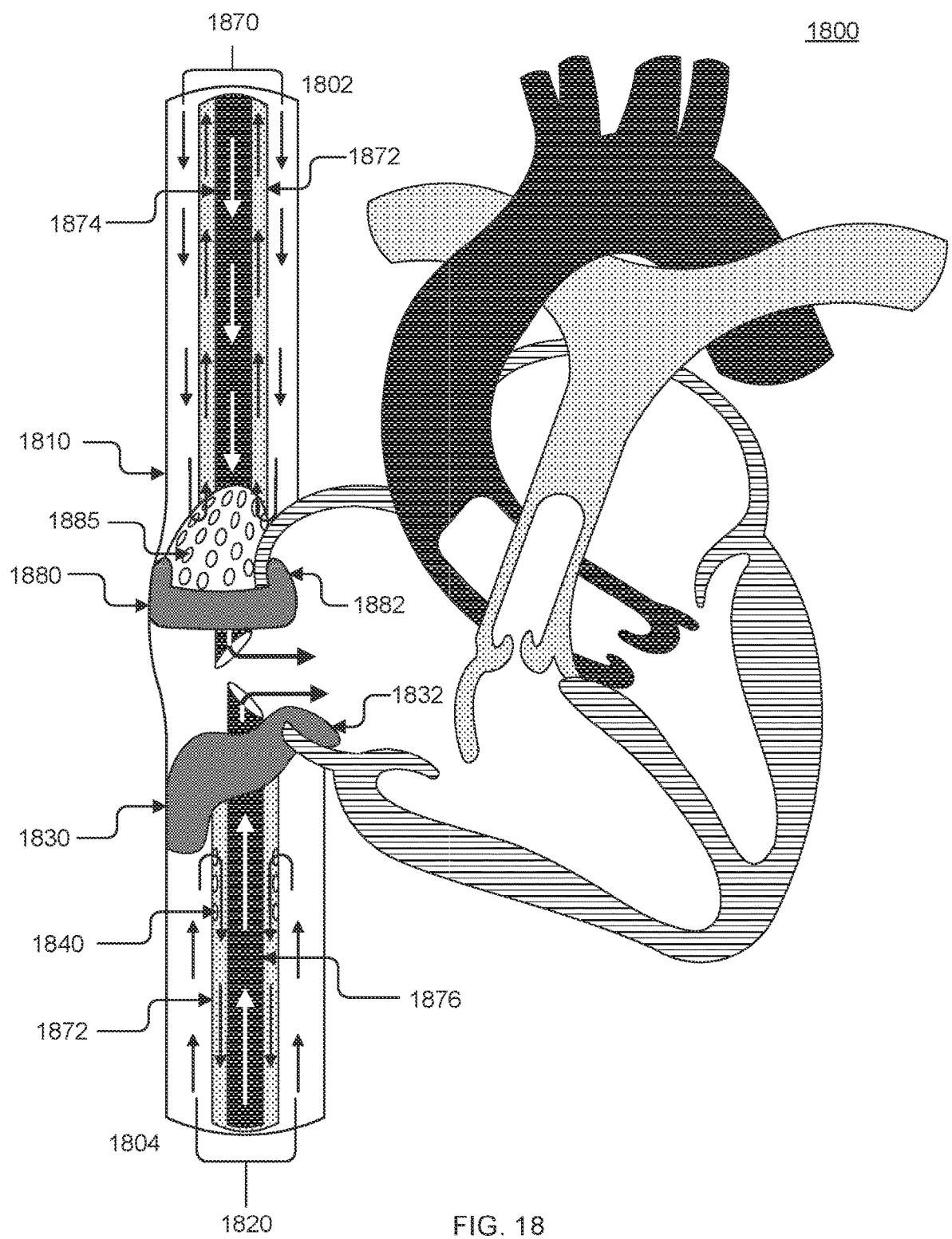
FIG. 18 illustrates a heart with an exemplary cannula system, according to some embodiments of the present disclosure.

Referring now to FIG. 18, a plurality of exemplary dual cannula 1820, 1870 is illustrated. In some embodiments, the dual cannula 1820, 1870 may exist within the same blood vessel 1810. For example, a dual cannula 1870 may near proximity to the heart from the direction of the SVC 1802. The dual cannula 1870 may approach entrance of the heart, where it deposits oxygenated blood into the heart while a balloon cuff 1880 prevents occlusion. An additional dual cannula 1820 may enter the blood vessel 1810 from the direction of the IVC 1804.

The dual cannula 1820 may approach entrance of the heart, where it deposits oxygenated blood into the heart while a balloon cuff 1830 prevents occlusion. In some embodiments, a plurality of reinfusion cannula 1874, 1876 may deposit oxygenated blood directly into the heart. In some implementations, the dual cannula 1820, 1870 may comprise a balloon cuff 1830, 1880. In some aspects, the balloon cuff 1830, 1870 may comprise a positioning arm 1832, 1882. In some embodiments, the positioning arm 1832, 1882 may allow the reinfusion cannula 1874, 1876 to inject oxygenated blood directly into the heart. In some aspects, the balloon cuff 1830, 1880 may surrounding the distal end of the reinfusion cannula 1874, 1876 as it deposits blood into the heart.

This separation from the blood vessel 1810 may prevent occlusion. This separation may improve oxygenation efforts by reducing the mixing of oxygenated and deoxygenated blood. The flow within the blood vessel 1810 may be facilitated via the drainage cannula 1872 and the associated cannula flow mechanism 1840. In some implementations, the balloon cuff may comprise a balloon flow mechanism 1885. The balloon flow mechanism 1885 may direct deoxygenated blood flow into the drainage cannula 1872.

The dual cannula 1820 may approach entrance of the blood vessel 1810 into the heart, where it deposits oxygenated blood into the heart while a balloon cuff 1830 prevents occlusion. In some embodiments, a plurality of reinfusion cannula 1874, 1876 may deposit oxygenated blood directly into the heart. In some implementations, the dual cannula 1820, 1870 may comprise a balloon cuff 1830, 1880.

Figure 19:
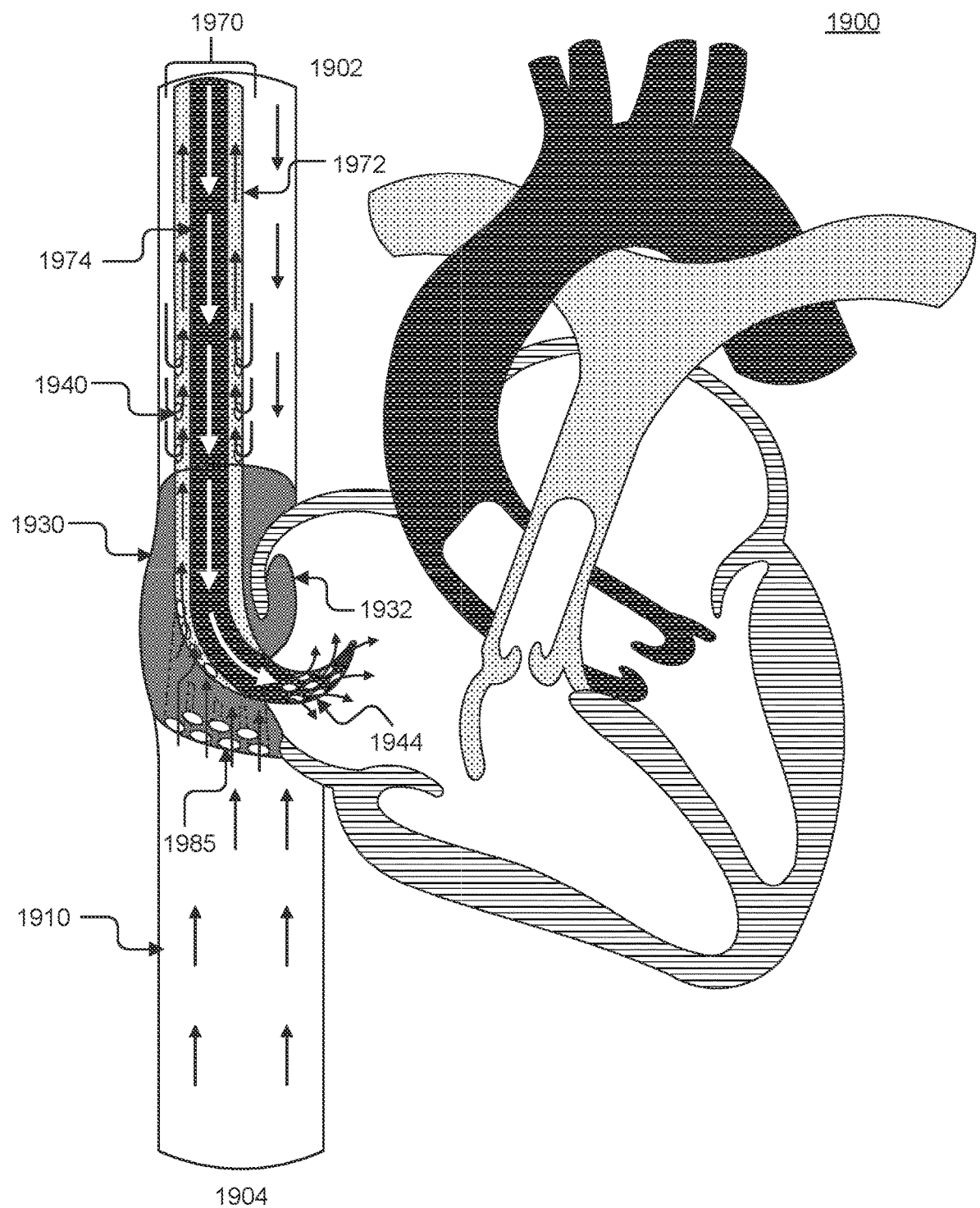
FIG. 19 illustrates an exemplary heart with cannula system, according to some embodiments of the present disclosure.

Referring now to FIG. 19, an exemplary cannula system 1900 is illustrated. In some embodiments, a dual cannula 1970 may comprise reinfusion cannula 1974 that enter the heart from the direction of the SVC 1902. The dual cannula 1970 may approach via entrance of the heart, where it deposits oxygenated blood into the heart while a balloon cuff 1930 prevents occlusion. This separation may improve oxygenation efforts by reducing the mixing and recirculation of oxygenated and deoxygenated blood. The end of reinfusion cannula 1974 may comprise a plurality of openings 1944 to facilitate reinfusion of oxygenated blood into the right atrium.

As an illustrative example, the dual cannula 1970 may be placed via SVC 1902 as depicted or via the IVC 1904. Openings within the balloon flow mechanism 1985 may be connected to drainage cannula 1972 and facilitate drainage from IVC 1904. If the dual cannula 1970 is placed from IVC 1904, then a cannula flow mechanism may collect venous blood from SVC 1902. The balloon cuff 1930 may prevent mixing and occlusion.

In some aspects, the balloon cuff 1930 may comprise a positioning arm 1932. In some embodiments, the positioning arm 1932 may allow the reinfusion cannula 1974 to inject oxygenated blood directly into the heart. In some aspects, the balloon cuff 1930 may surround the distal end of the reinfusion cannula 1974 as it deposits blood into the heart. The flow within the blood vessel 1910 may be facilitated via the drainage cannula 1972 and the associated cannula flow mechanism 1940. In some implementations, the balloon cuff 1930 may comprise a balloon flow mechanism 1985. The balloon flow mechanism 1985 may direct deoxygenated blood flow into the drainage cannula 1972.

Figure 20A:
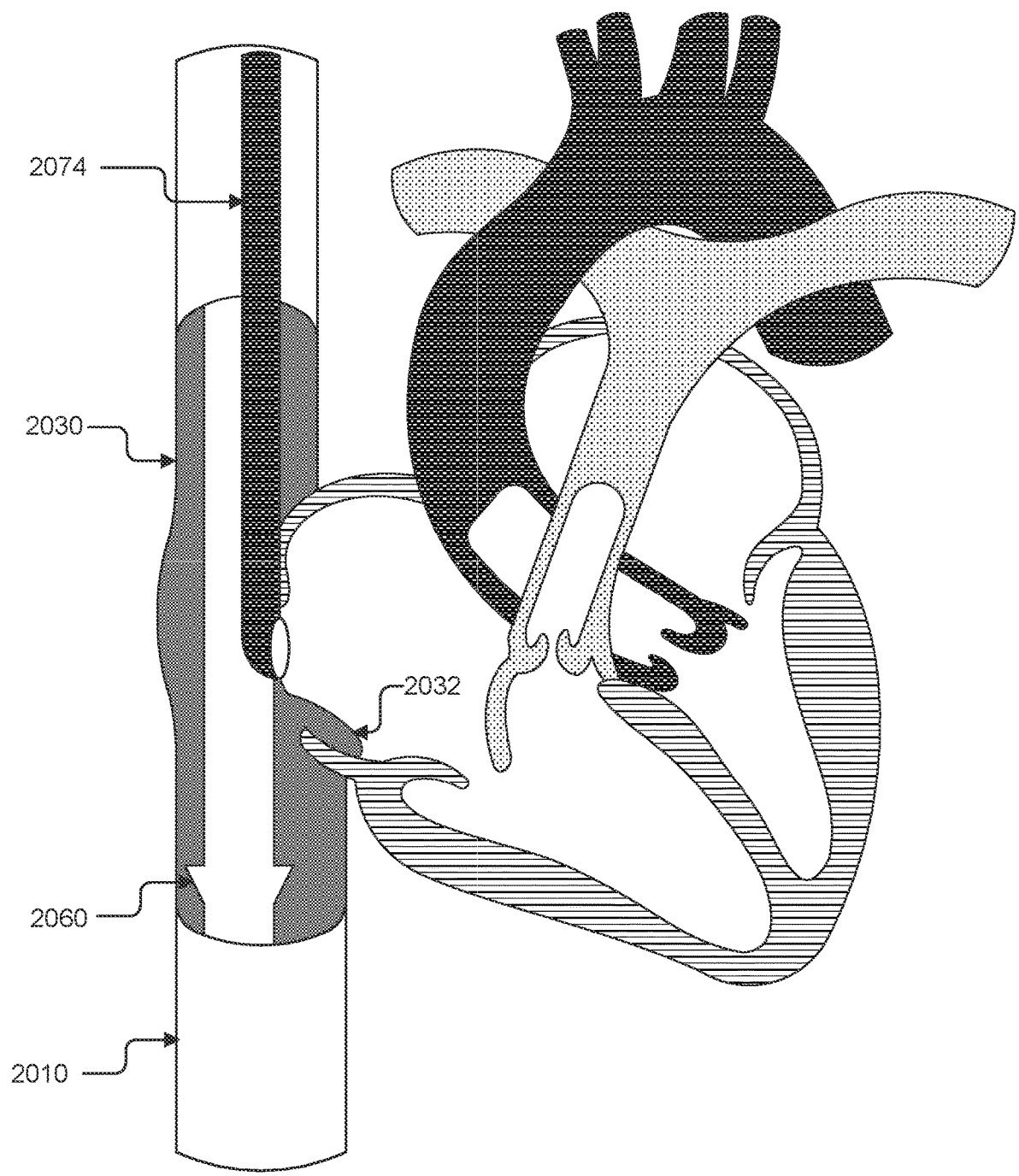
FIG. 20A illustrates an exemplary heart with cannula system, according to some embodiments of the present disclosure.
Figure 20B:
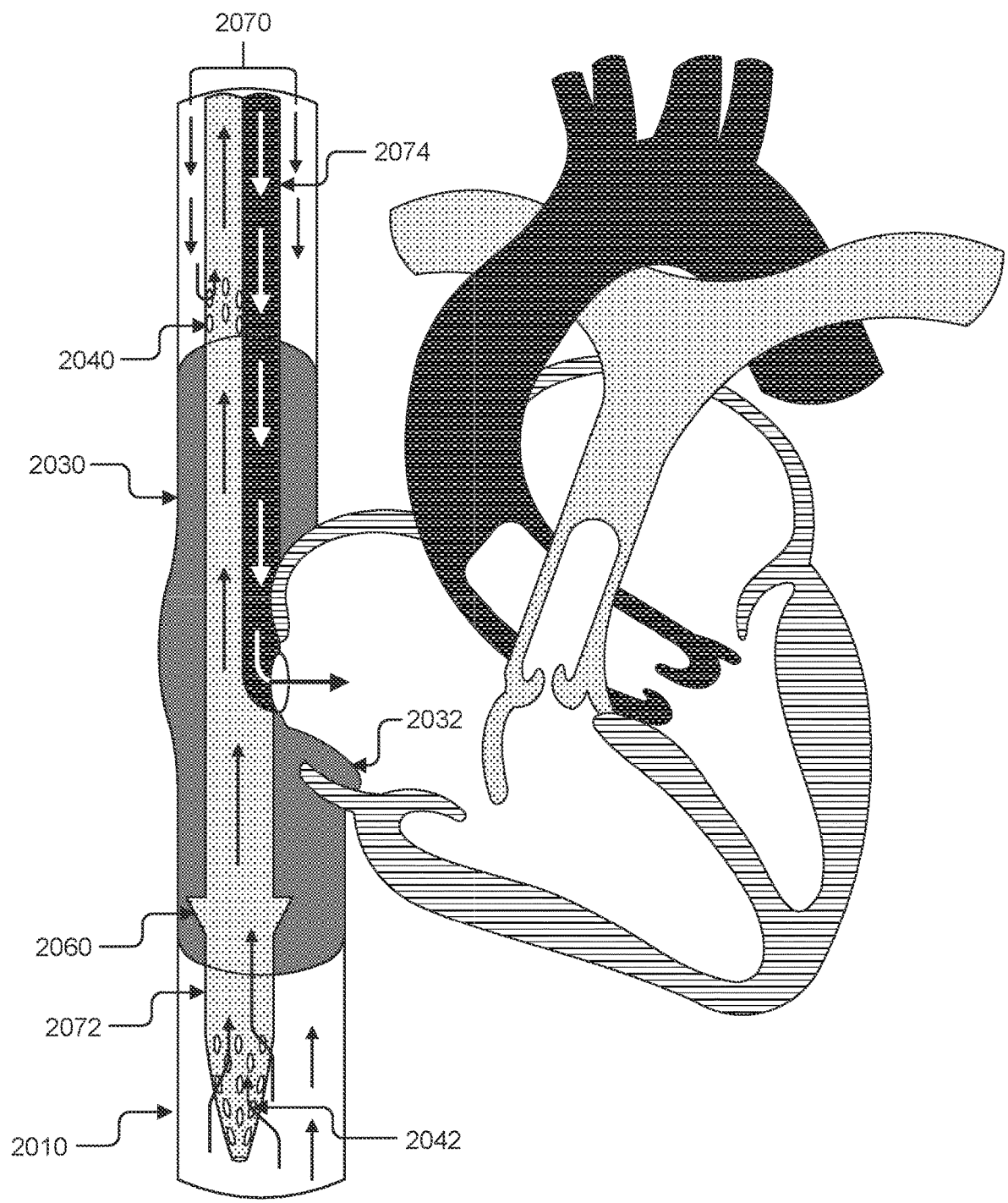
FIG. 20B illustrates an exemplary heart with cannula system, according to some embodiments of the present disclosure.

Referring now to FIGS. 20A-20B, an exemplary heart with cannula system is illustrated. In some embodiments, a drainage cannula 2074 may comprise a balloon cuff 2030. The positioning of the balloon cuff 2030 may be secured via a positioning arm 2032 that may apply a securing force on the entrance wall of the heart. In some implementations, the balloon cuff 2030 may comprise a balloon flow mechanism. In some aspects, the balloon flow mechanism may comprise an empty cavity that may be occupied by additional cannula. In some embodiments, the balloon flow mechanism may comprise a cannula connection mechanism 2060.

In some implementations, the dual cannula 2070 may comprise one or more cannula. In some aspects, the cannula may be separate cannula that are positioned via a balloon cuff 2030. For example, after inserting the reinfusion cannula 2074 and inflating the balloon cuff 2030, the drainage cannula 2072 may be inserted into the balloon flow mechanism. The cannula connection mechanism 2060 within the balloon flow mechanism may secure the position of the drainage cannula 2072 within the blood vessel 2010.

In some embodiments, the drainage cannula 2072 may comprise one or more cannula flow mechanism 2040, 2042. In some implementations, the cannula flow mechanism 2040, 2042 may allow for deoxygenated blood extract from one or more locations within the blood vessel 2010. For example, the drainage cannula 2072 may extrude from both sides of a balloon cuff 2030. A cannula flow mechanism 2042 may collect deoxygenated blood from one side of the balloon cuff 2030 and another cannula flow mechanism 2040 may collect blood from the alternative side of the balloon cuff 2030. This plurality of cannula flow mechanism 2040 may allow deoxygenated blood to continue flowing through the blood vessel while the balloon cuff 2030 is inflated and may otherwise block fluid through the blood vessel 2010.

Figure 21A:
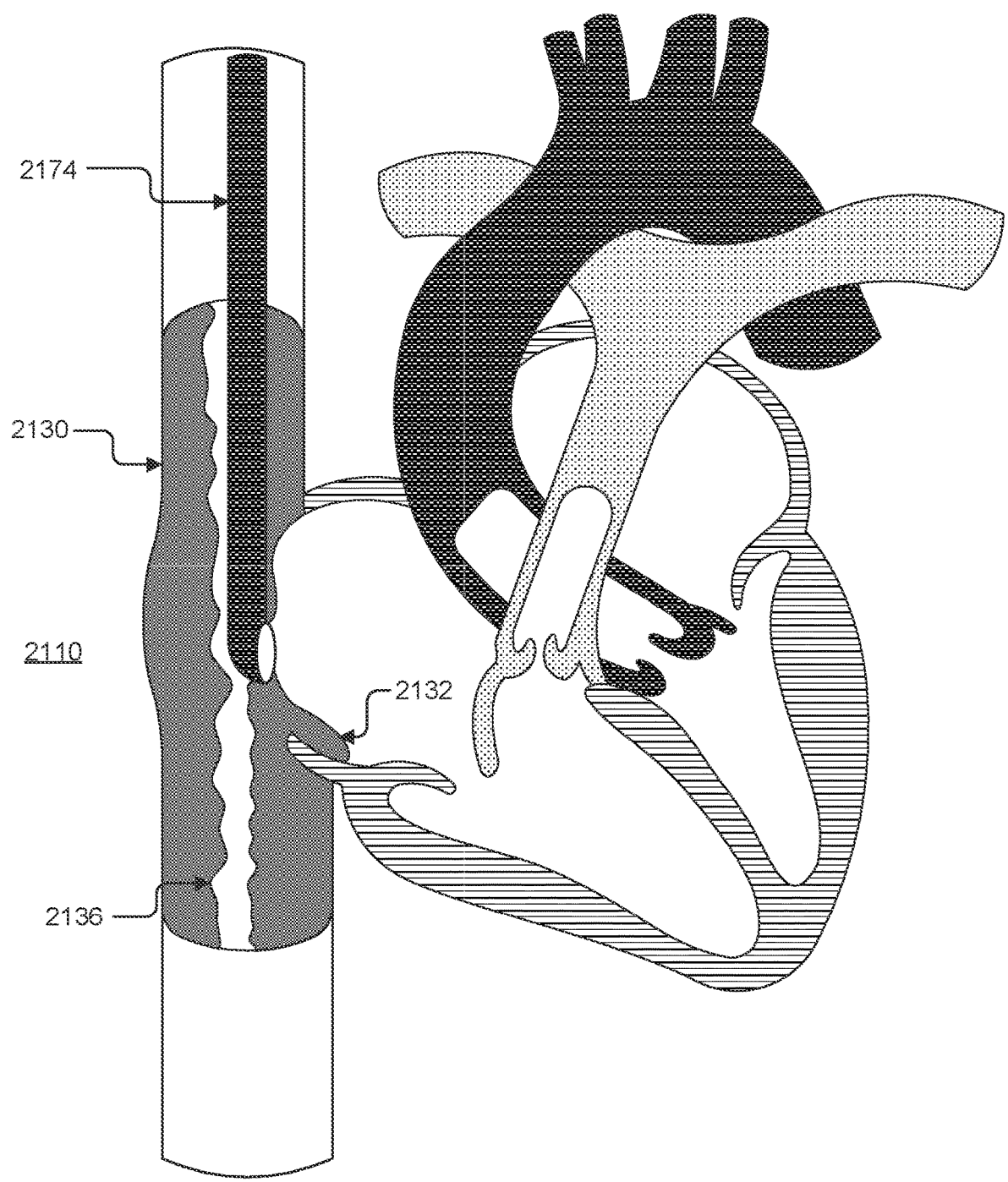
FIG. 21A illustrates an exemplary heart with cannula system, according to some embodiments of the present disclosure.
Figure 21B:
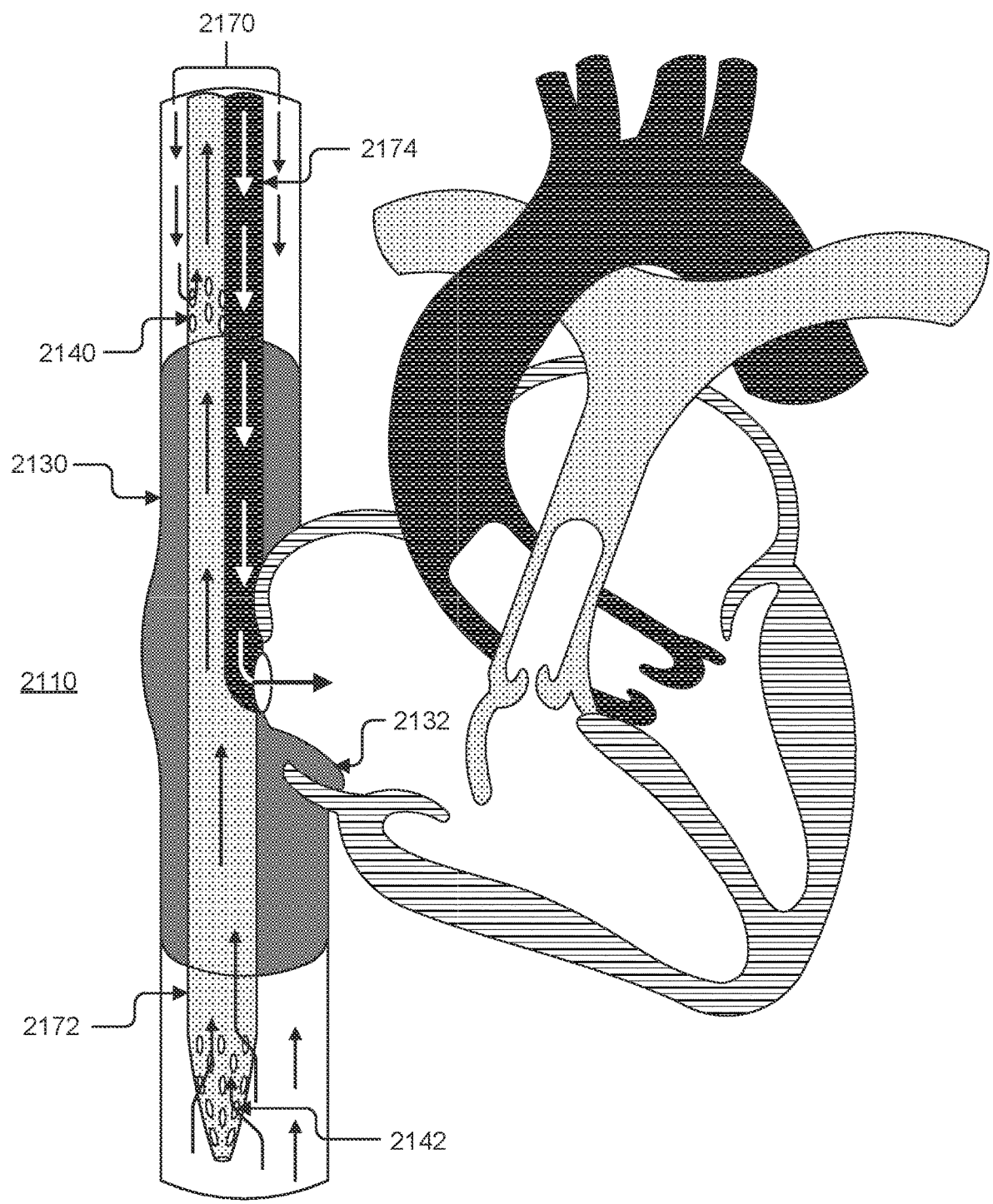
FIG. 21B illustrates an exemplary heart with cannula system, according to some embodiments of the present disclosure.

Referring now to FIGS. 21A-21B, an exemplary heart with cannula system is illustrated. In some embodiments, a reinfusion cannula 2174 may comprise a balloon cuff 2130. The positioning of the balloon cuff 2130 may be secured via a positioning arm 2132 that may apply a stabilizing force on the entrance wall of the heart. In some implementations, the balloon cuff 2130 may comprise a balloon flow mechanism 2136. In some aspects, the balloon flow mechanism 2136 may comprise an empty cavity that may be occupied by additional cannula.

In some implementations, the dual cannula 2170 may comprise one or more cannula. In some aspects, the cannula may be separate cannula that are positioned via a balloon cuff 2130. For example, after inserting the reinfusion cannula 2174 and inflating the balloon cuff 2130, the drainage cannula 2172 may be inserted into the balloon flow mechanism 2136. In some embodiments, a small quantity of composite material may be embedded within the tip of the drainage cannula 2172 that is traceable external to the body. This may assist in ensuring correct placement of the drainage cannula 2172 within the heart.

In some implementations, a small tracer may be embedded within the tip of the inserted cannula. This tracer may comprise electronic components that may emit traceable frequencies or signals, as non-limiting options. In some aspects, an embedded magnetic may assist the guidance of the insertion of the cannula externally. In some embodiments, the drainage cannula 2172 may comprise one or more cannula flow mechanism 2140, 2142. In some implementations, the cannula flow mechanism 2140, 2142 may allow for deoxygenated blood extraction from one or more locations within the blood vessel 2110.

For example, the drainage cannula 2172 may extrude from both sides of a balloon cuff 2130. A cannula flow mechanism 2142 may collect deoxygenated blood from one side of the balloon cuff 2130 and another cannula flow mechanism 2140 may collect blood from the alternative side of the balloon cuff 2130. This plurality of cannula flow mechanism 2140 may allow deoxygenated blood to continue flowing through the blood vessel while the balloon cuff 2130 is inflated and may otherwise block fluid through the blood vessel 2110.

Figure 22A:
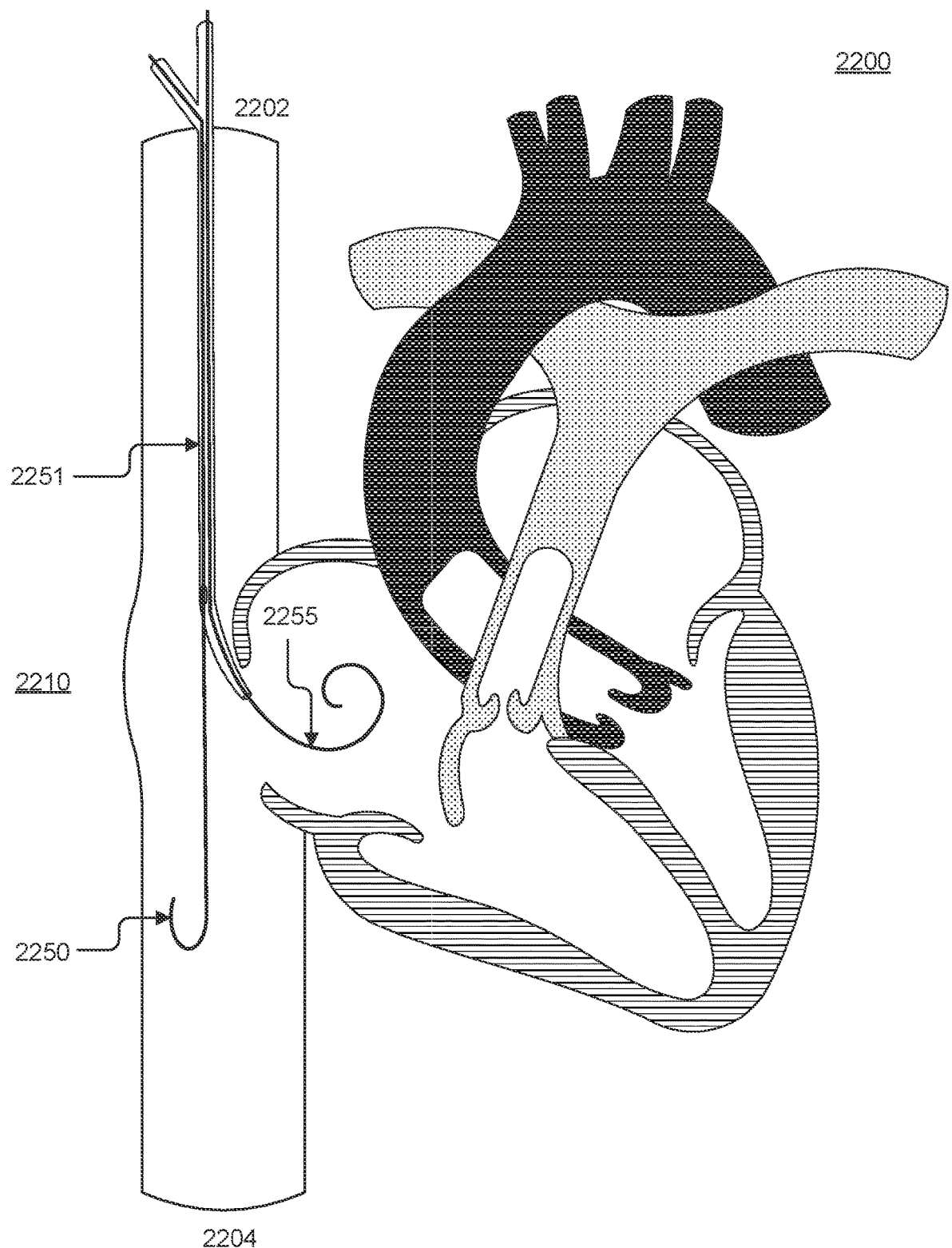
FIG. 22A illustrates an exemplary insertion step for a heart with cannula system, according to some embodiments of the present disclosure.
Figure 22B:
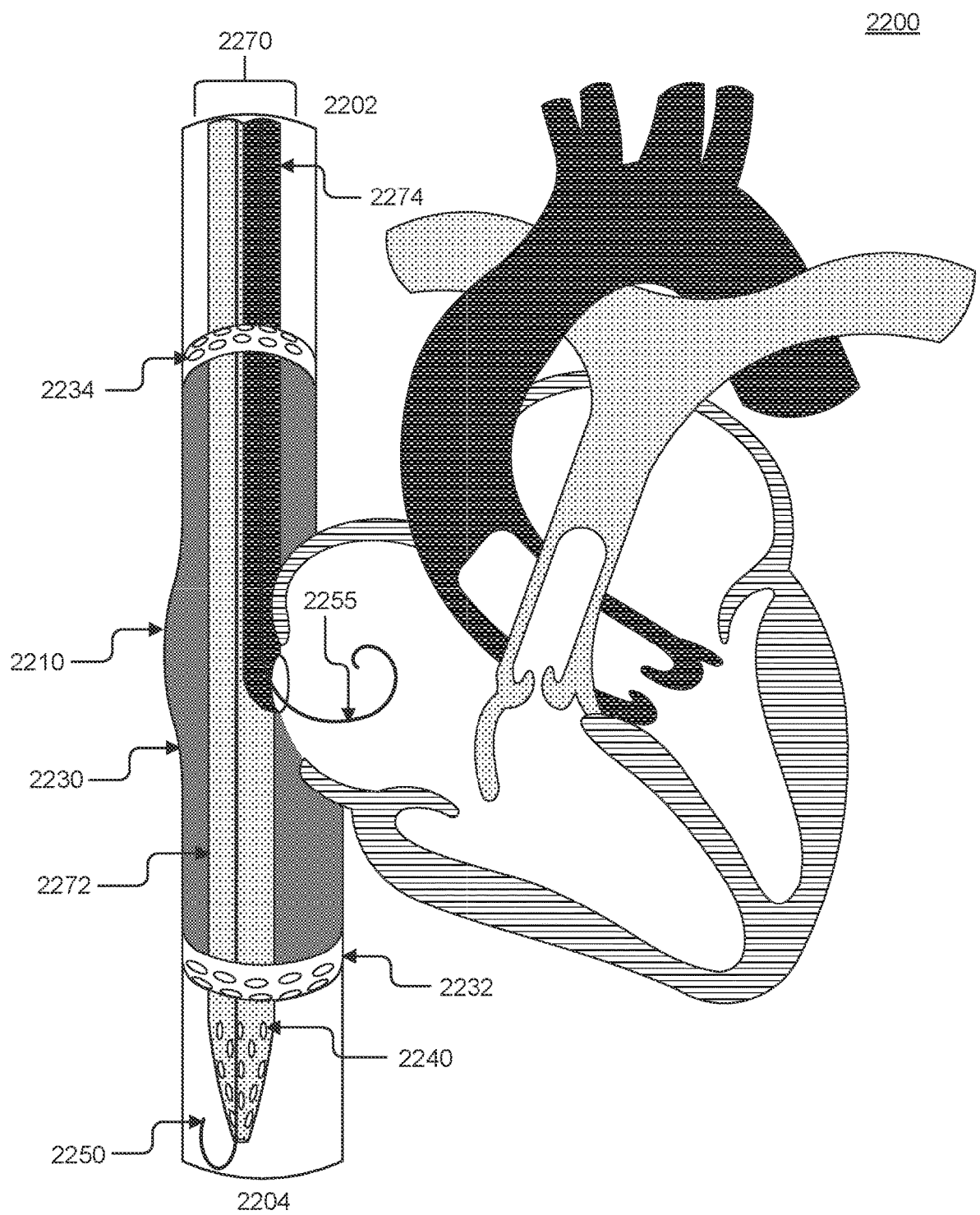
FIG. 22B illustrates an exemplary heart with cannula system, according to some embodiments of the present disclosure.
Figure 22C:
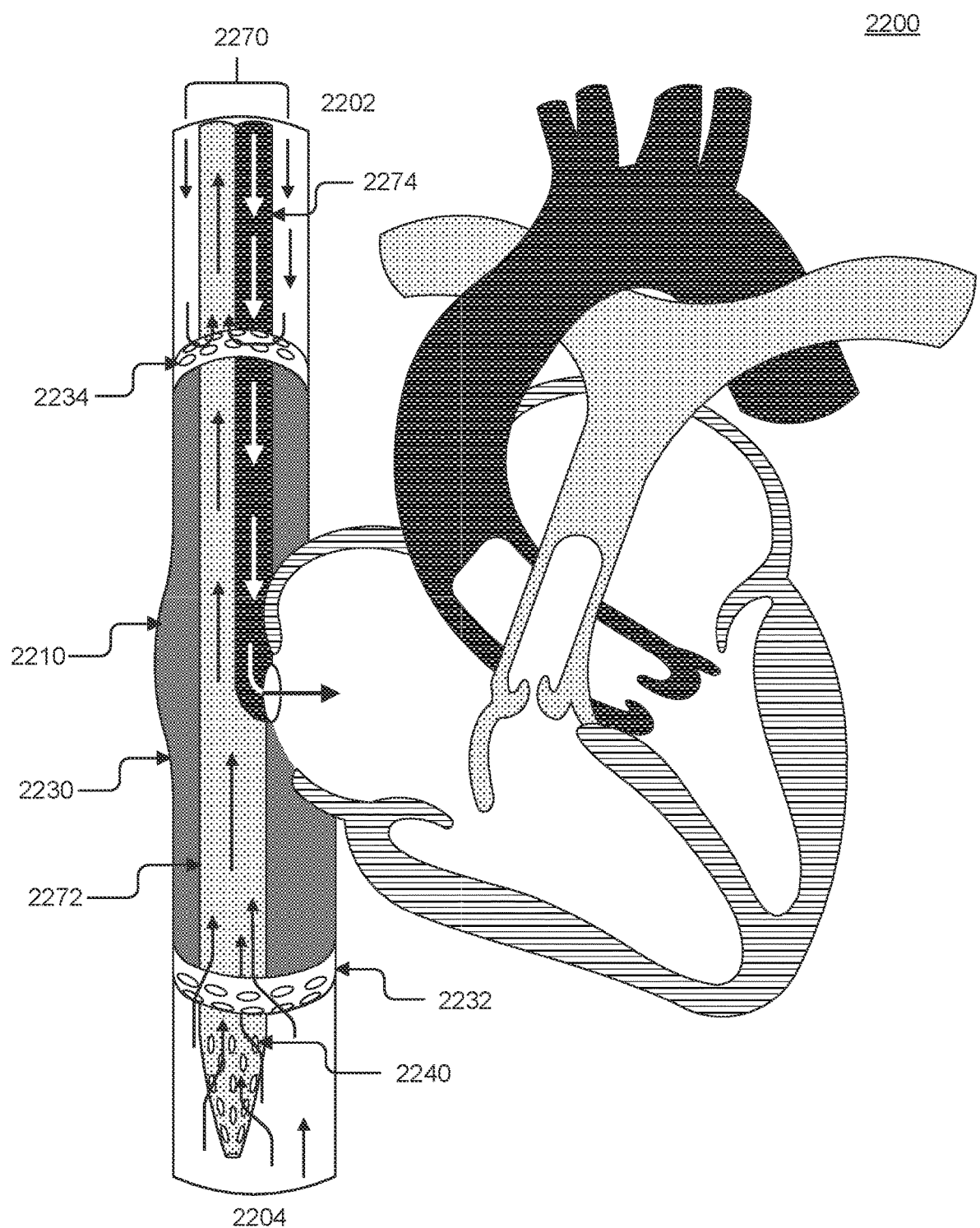
FIG. 22C illustrates an exemplary heart with cannula system, according to some embodiments of the present disclosure.
Figure 23A:
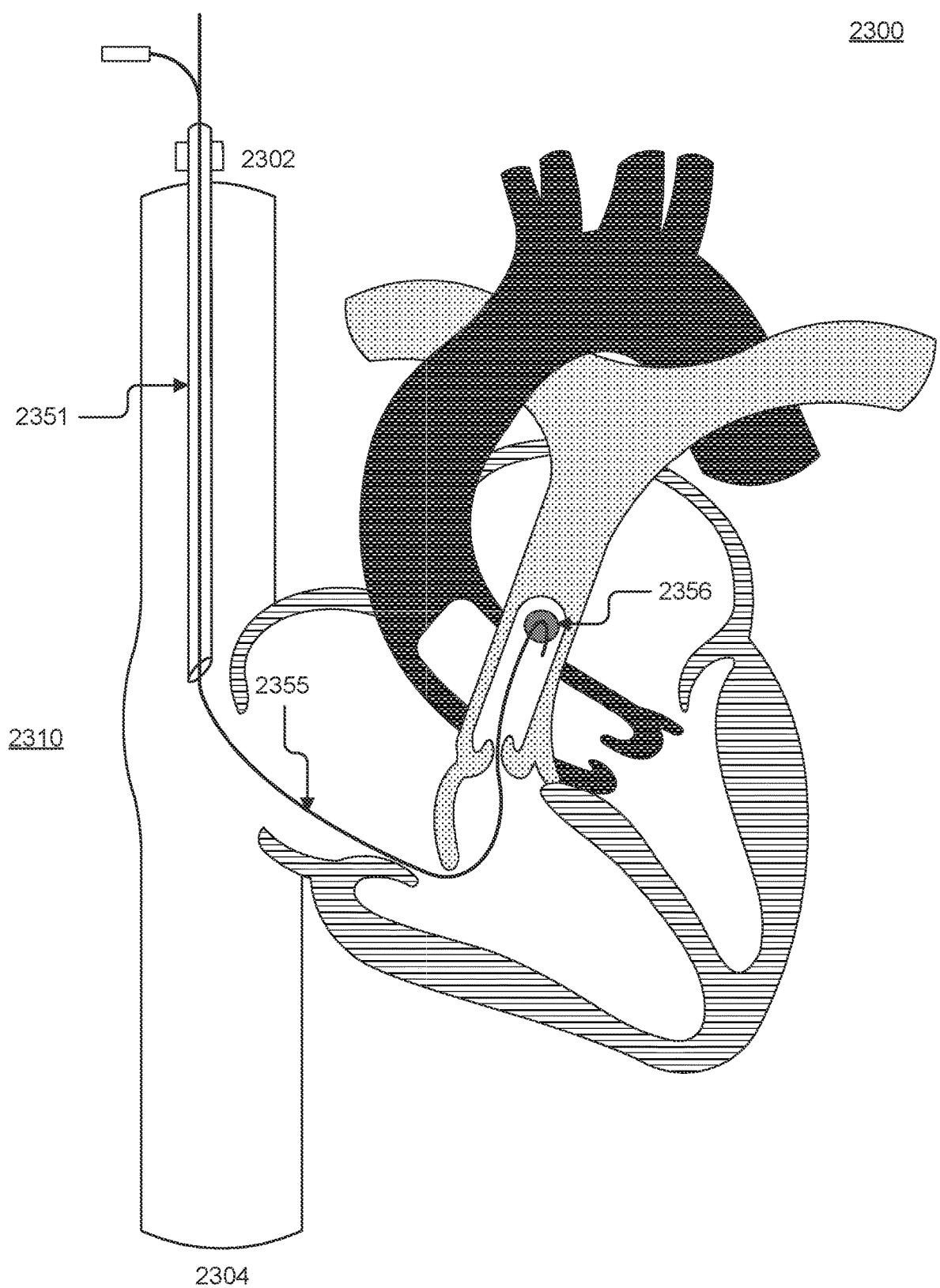
FIG. 23A illustrates an exemplary insertion step for a heart with cannula system, according to some embodiments of the present disclosure.
Figure 23B:
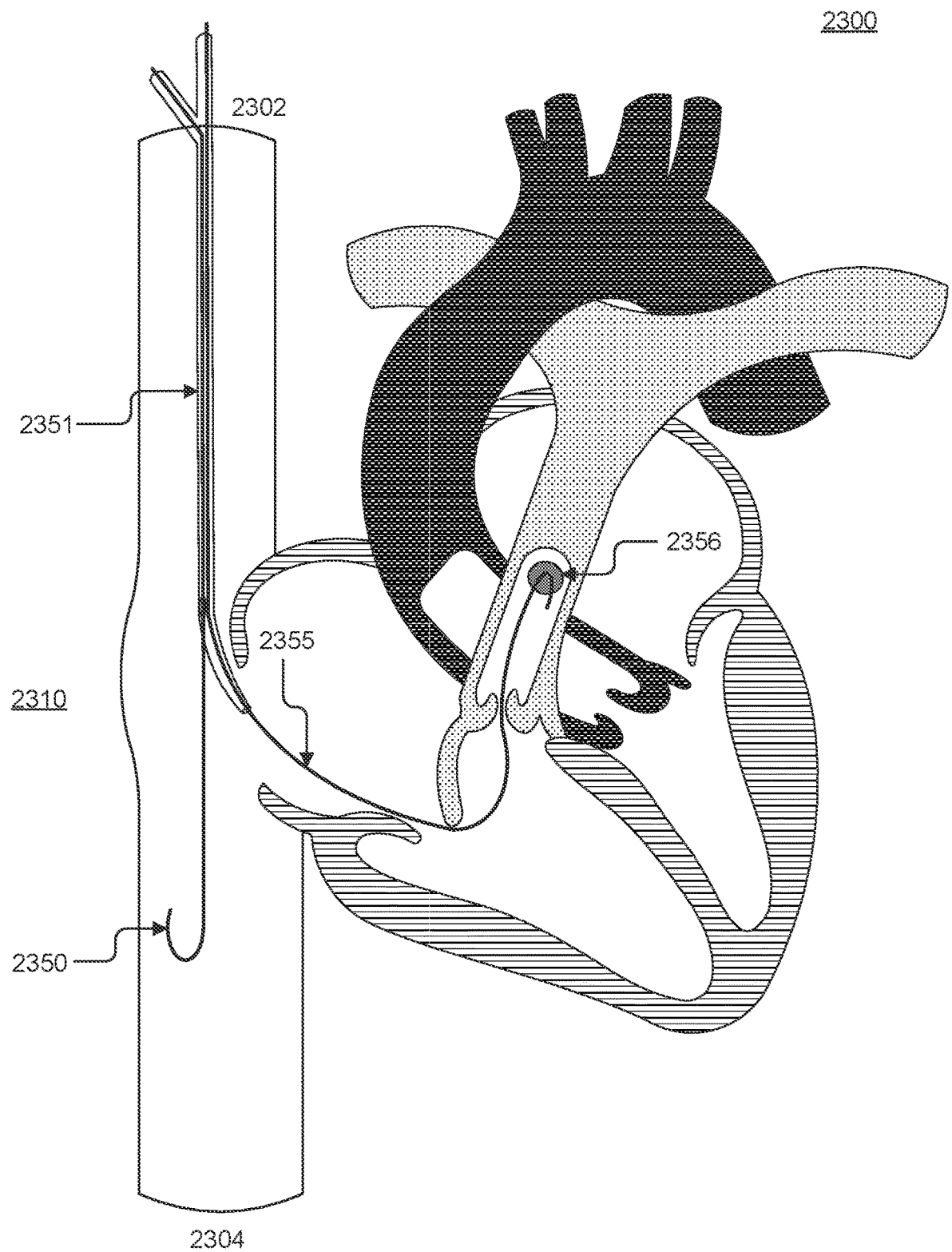
FIG. 23B illustrates an exemplary heart with cannula system, according to some embodiments of the present disclosure.
Figure 23C:
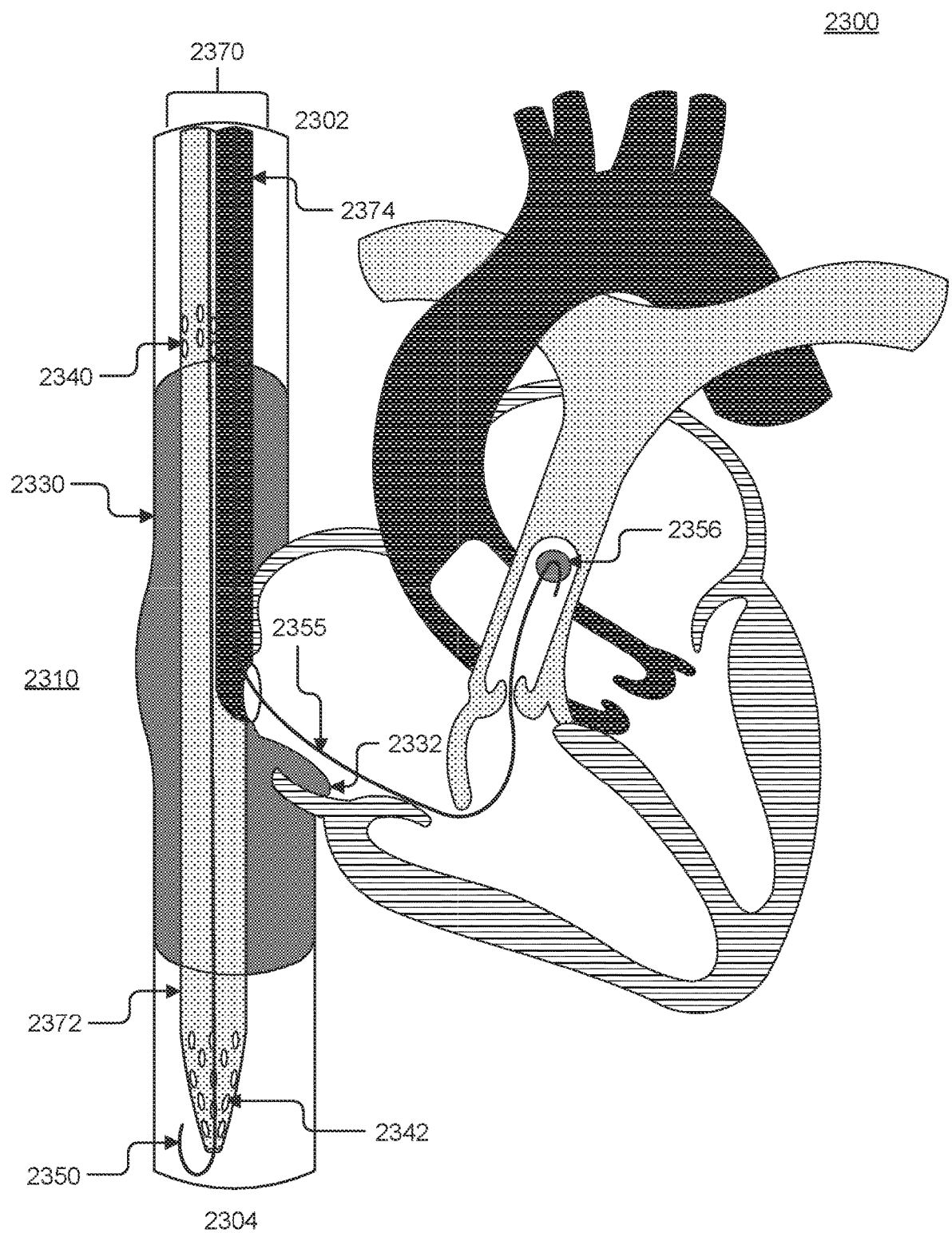
FIG. 23C illustrates an exemplary heart with cannula system, according to some embodiments of the present disclosure.
Figure 23D:
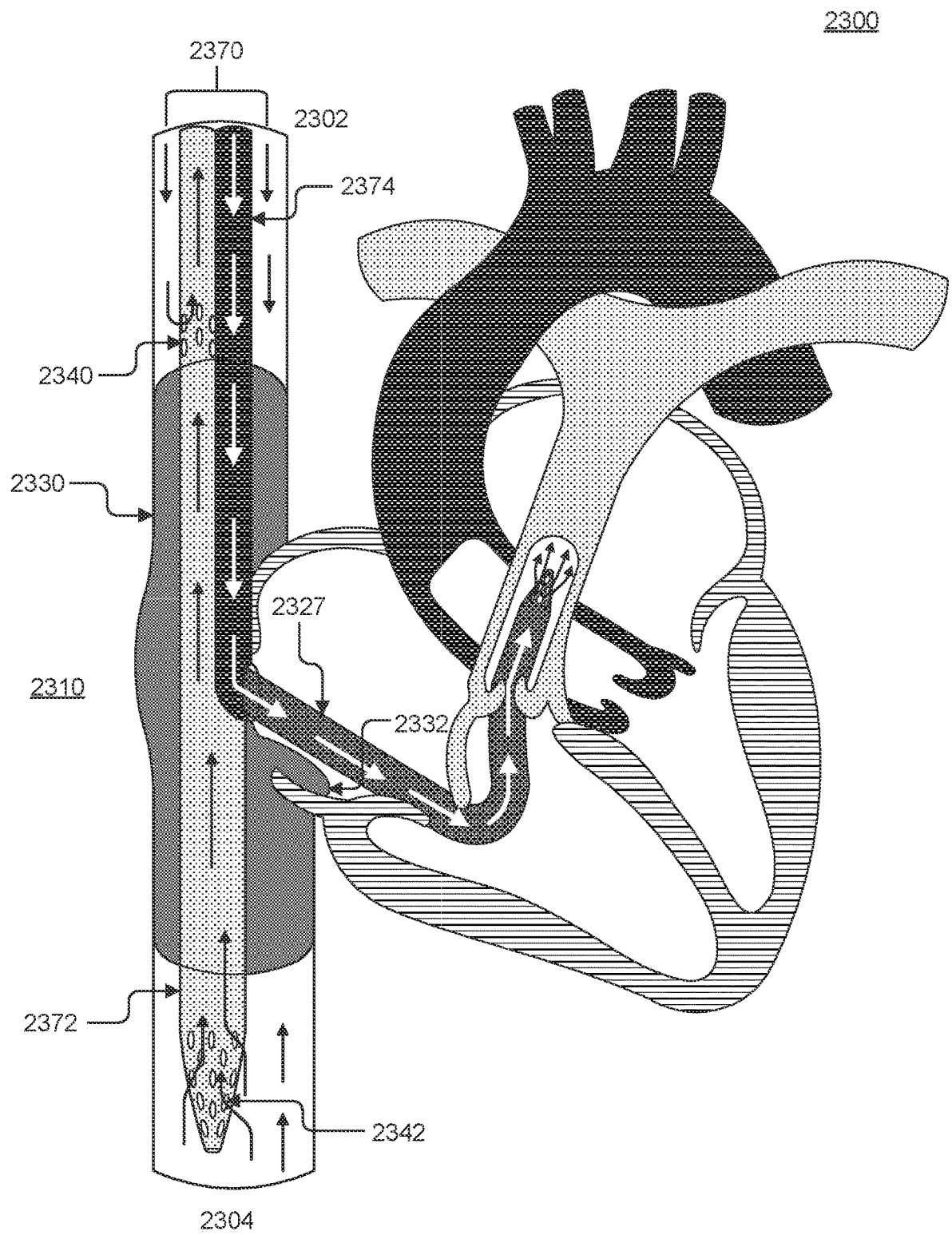
FIG. 23D illustrates an exemplary heart with cannula system, according to some embodiments of the present disclosure.
Figure 23E:
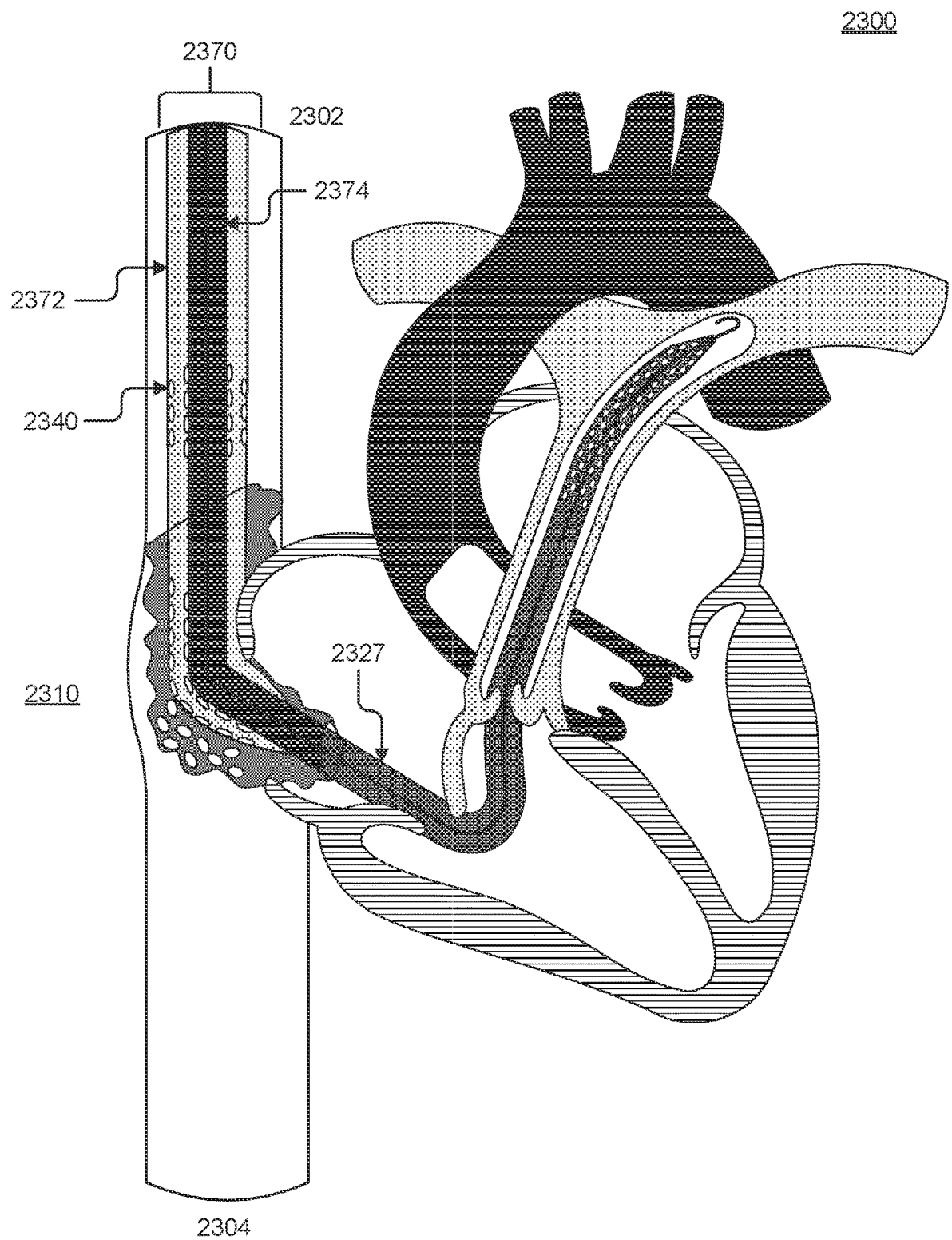
FIG. 23E illustrates an exemplary heart with cannula system, according to some embodiments of the present disclosure.
Figure 23F:
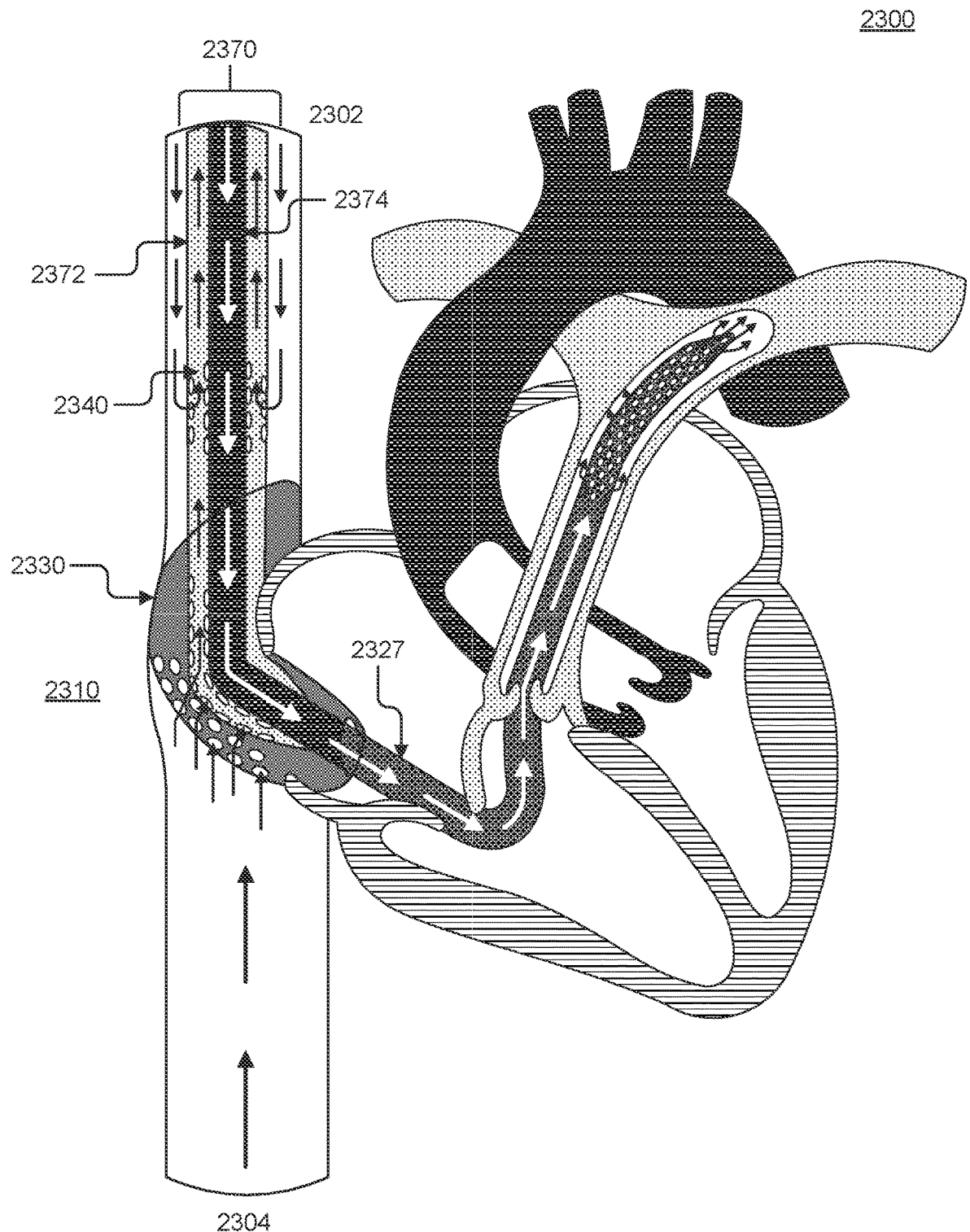
FIG. 23F illustrates an exemplary heart with cannula system, according to some embodiments of the present disclosure.

Referring now to FIGS. 22A-22C, an exemplary heart with cannula system 2200 is illustrated. In some embodiments, a cannula system 2200 may comprise one or more insertion devices 2250, 2255. The positioning of the insertion mechanisms 2250, 2255 may result in the placement of the insertion mechanisms in one or more locations.

For example, the injection device 2251 may be inserted via the SVC 2202 and one insertion mechanism 2250 may extend toward the IVC 2204 and a second insertion mechanism 2255 may enter the heart. In some implementations, the injection device 2251 may comprise a tapered diameter to prepare the insertion point for introduction to the blood vessel 2210. In some aspects, the positioning of the insertion mechanisms 2250, 2255 may be assisted by an external location indicator.

In some embodiments, a reinfusion cannula 2274 may comprise a balloon cuff 2230. In some implementations, the dual cannula 2270 may comprise one or more cannula. In some aspects, the dual cannula 2270 may comprise separate cannula that are positioned via a balloon cuff 2230. In some implementations, the insertion mechanisms 2250, 2255 may assist in positioning the cannulae within the blood vessel 2210. In some embodiments, the drainage cannula 2272 may comprise a cannula flow mechanism 2240. In some implementations, the cannula flow mechanism 2040 may allow for deoxygenated blood extraction from within the blood vessel 2210.

In some embodiments, the balloon cuff may comprise a plurality of balloon cuff 2232, 2234. In some implementations, the balloon cuff 2232, 2234 may assist in securing the balloon in place. In some embodiments, the balloon cuff 2232, 2234 may assist in drainage of blood into the reinfusion cannula 2274 by preventing collapse of SVC 2202 IVC 2204 accordingly. In some aspects, the balloon cuffs 2232, 2234 may assist securing the cannulae. In some embodiments, the balloon cuffs 2232, 2234 may maintain openings for the insertion of cannulae. In some implementations, the balloon cuffs 2232, 2234 may allow for some flexibility with fit to ensure that the cannula openings are not blocked once inserted. In some aspects, the insertion mechanism 2255 may facilitate proper positioning of the reinfusion cannula 2274 opening toward the heart.

Referring now to FIGS. 23A-23F, an exemplary heart with cannula system 2300 is illustrated. In some embodiments, a cannula system 2300 may comprise one or more insertion devices 2350, 2355. The positioning of the insertion mechanisms 2350, 2355 may result in the placement of the insertion mechanisms in one or more locations. For example, the injection device 2351 may be inserted via the SVC 2302 and one insertion mechanism 2350 may extend toward the 2304 IVC and a second insertion mechanism 2355 may enter the heart. The insertion mechanism 2355 may comprise a balloon 2356 at predetermined locations along the insertion mechanism 2355 to allow the insertion mechanism 2355 to be floated into pulmonary artery, as a non-limiting example. In some implementations, the injection device 2351 may comprise a tapered diameter to prepare the insertion point for introduction to the blood vessel 2310.

In some embodiments, a reinfusion cannula 2374 may comprise a balloon cuff 2330. In some implementations, the dual cannula 2370 may comprise one or more cannula. In some aspects, the dual cannula 2370 may comprise separate cannula that are positioned via a balloon cuff 2330. In some implementations, the insertion mechanisms 2350, 2355 may assist in positioning the cannulae within the blood vessel 2310. In some aspects, the insertion mechanisms 2355 may comprise a small balloon 2356 at the curvature of the insertion mechanisms 2355 near the tip to assist with secure placement in the pulmonary artery.

In some embodiments, a reinfusion cannula 2374 may comprise a balloon cuff 2330. The positioning of the balloon cuff 2330 may be secured via a positioning arm 2332 that may apply a stabilizing force on the entrance wall of the heart. In some implementations, the cannula system 2300 may comprise a cannula extender 2327. In some embodiments, the cannula extender 2327 may comprise an insertion mechanism 2355 to facilitate secure placement with the vessel. In some implementations, the cannula extender 2327 may comprise a cannula flow mechanism to facilitate blood flow to a targeted region of a vessel or heart. In some aspects, the cannula extender 2327 may extend the range of the cannula.

As an illustrative example, the tip of the cannula extender 2327 may be advanced into the left atrium via crossing the interatrial septum. In some implementations, the tip of the cannula extender 2327 may be advanced into left ventricle or ascending aorta via crossing interatrial septum then mitral valve then aortic valve.

As another example, a reinfusion cannula 2374 may comprise a cannula extender 2327 that allows the reinfusion cannula 2374 to bypass chambers within the heart to insert oxygenated blood at a deeper point within the heart. The cannula extender 2327 may proceed through the right atrium and right ventricle of the heart into the pulmonary artery, thereby facilitating blood flow from the superior and inferior vena cavas to the pulmonary artery while bypassing the right atrium and right ventricle.

The cannula extender 2327 may be tapered to penetrate regions of the body that require a smaller diameter than a standard blood vessel 2310. The cannula extender 2327 may comprise a thinner material wall that provides greater flexibility to the cannula extender 2327.

In some embodiments, the drainage cannula 2372 may comprise one or more cannula flow mechanism 2340, 2342. In some implementations, the cannula flow mechanism 2340, 2342 may allow for deoxygenated blood extract from one or more locations within the blood vessel 2310. For example, the drainage cannula 2372 may extrude from both sides of a balloon cuff 2030. A cannula flow mechanism 2342 may collect deoxygenated blood from one side of the balloon cuff 2330 and another cannula flow mechanism 2340 may collect blood from the alternative side of the balloon cuff 2330. This plurality of cannula flow mechanism 2340 may allow deoxygenated blood to continue flowing through the blood vessel while the balloon cuff 2330 is inflated and may otherwise block fluid through the blood vessel 2310.

Figure 24A:
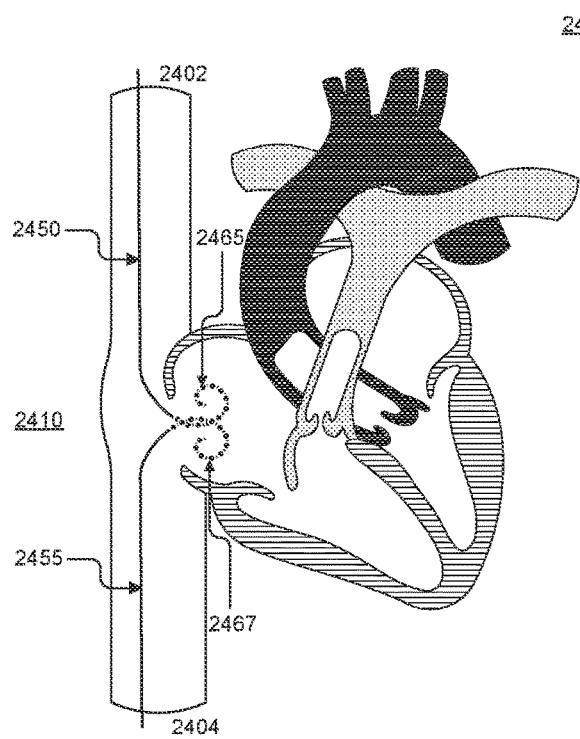
FIG. 24A illustrates an exemplary heart with cannula system, according to some embodiments of the present disclosure.
Figure 24B:
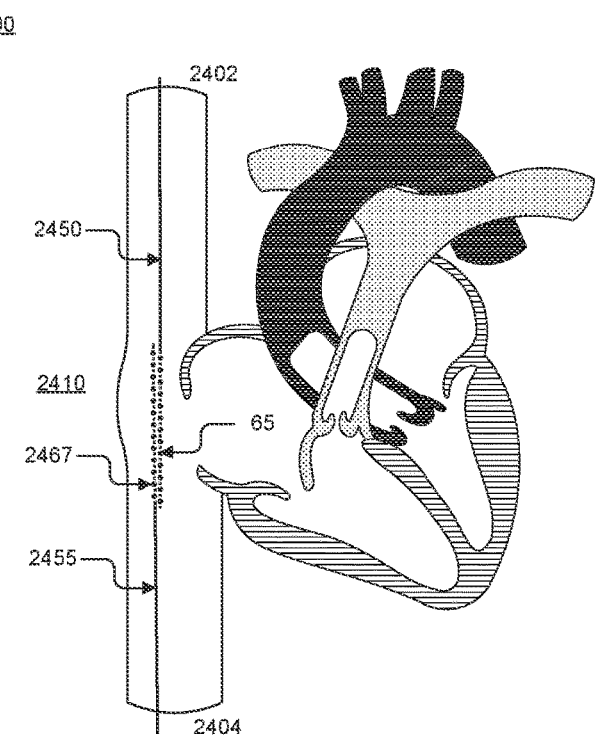
FIG. 24B illustrates an exemplary heart with cannula system, according to some embodiments of the present disclosure.
Figure 24C:
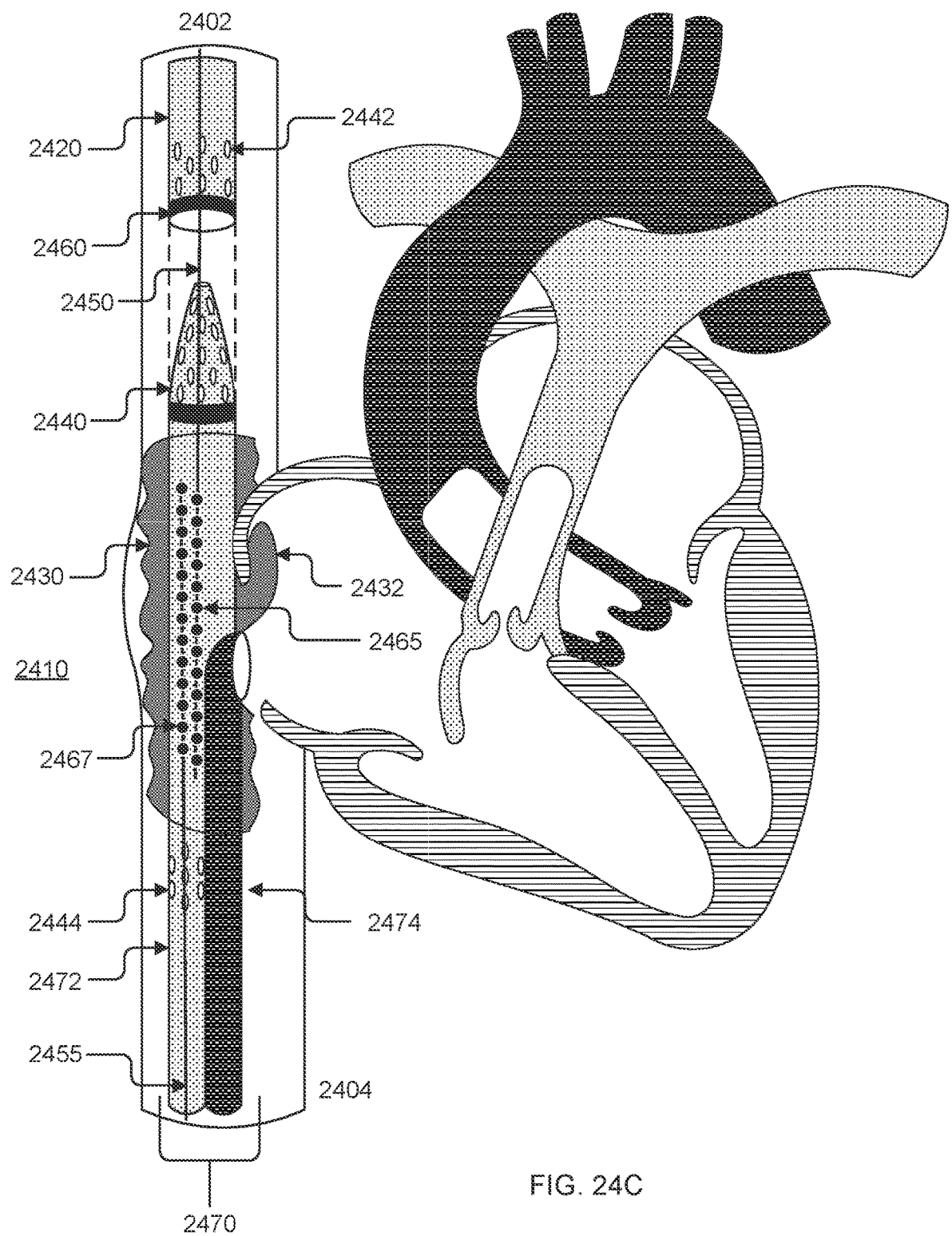
FIG. 24C illustrates an exemplary heart with cannula system, according to some embodiments of the present disclosure.

Referring now to FIGS. 24A-24C, an exemplary heart with cannula system 2400 is illustrated. In some embodiments, a cannula system 2400 may comprise one or more insertion devices 2450, 2455. The positioning of the insertion mechanisms 2450, 2455 may be assisted by one or more connection mechanisms 2465, 2467. For example, an insertion mechanism 2450 may be inserted via the SVC 2402 and one insertion mechanism 2450 may be inserted via the IVC 2404. The distal ends of the insertion mechanisms 2450, 2455 may possess magnetic characteristics. The magnetic force may allow the insertion mechanisms 2450, 2455 to become aligned in parallel or they may constrain an intertwined configuration.

In some implementations, the insertion mechanisms 2450, 2455 may facilitate insertion and orientation of one or more cannula within the blood vessel 2410. For example, a cannula 2420 may be inserted via the SVC 2402 and a dual cannula 2470 may be inserted via IVC 2404. The drainage cannula 2472 may comprise an insertion mechanism 2455 that aligns the dual cannula 2470 with the cannula 2420. The cannula 2420 and the dual cannula may connect via a cannula connection mechanism 2460. In some aspects, the reinfusion cannula 2474 may be attached to the drainage cannula 2472 via balloon cuff 2430.

In some embodiments, a drainage cannula 2472 may comprise a balloon cuff 2430. The positioning of the balloon cuff 2430 may be secured via a positioning arm 2432 that may apply a securing force on the entrance wall of the heart. In some implementations, the dual cannula 2470 may comprise one or more cannula. In some aspects, the cannula may be separate cannula that are positioned via a balloon cuff 2430.

For example, after inserting the reinfusion cannula 2474 and inflating the balloon cuff 2430, the drainage cannula 2472 may be inserted into the balloon flow mechanism. In some embodiments, the drainage cannula 2472 may comprise one or more cannula flow mechanism 2440, 2442, 2444. In some implementations, the cannula flow mechanism 2440, 2442, 2444 may allow for deoxygenated blood extract from one or more locations within the blood vessel 2410.

For example, the drainage cannula 2472 may extrude from both sides of a balloon cuff 2430. A cannula flow mechanism 2442 may collect deoxygenated blood from one side of the balloon cuff 2430 and another cannula flow mechanism 2440 may collect blood from the alternative side of the balloon cuff 2430. This plurality of cannula flow mechanism 2440 may allow deoxygenated blood to continue flowing through the blood vessel while the balloon cuff 2430 is inflated and may otherwise block fluid through the blood vessel 2410.

Figure 25:
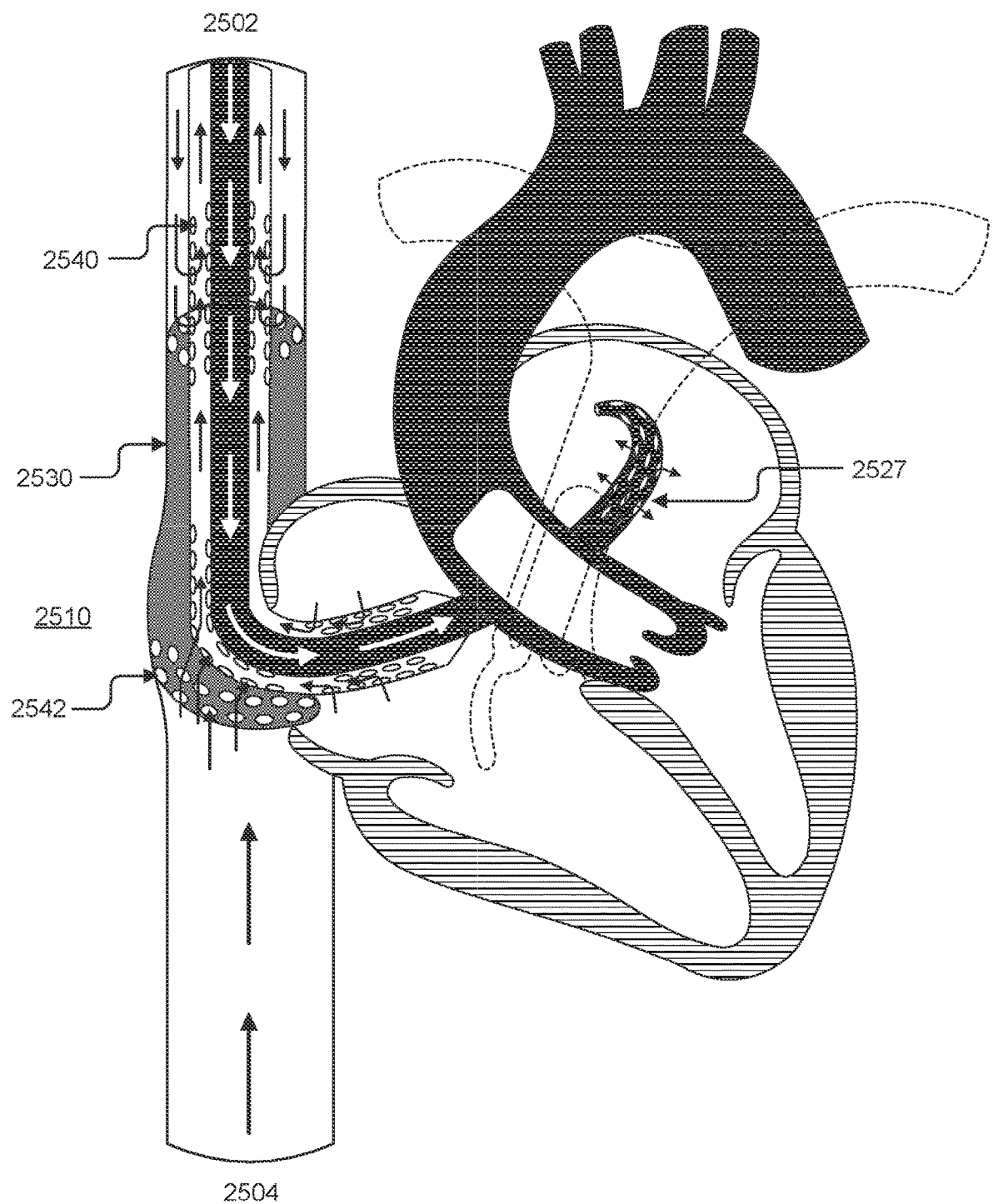
FIG. 25 illustrates an exemplary heart with cannula system, according to some embodiments of the present disclosure.

Referring now to FIG. 25, an exemplary heart with cannula system 2500 is illustrated. In some embodiments, the cannula system 2500 may be inserted via the SVC 2502. In some implementations, the dual cannula 2570 may comprise one or more cannula 2572, 2574. In some aspects, the cannulae 2572, 2574 may interact with different regions of the vessels and heart. As an example, the drainage cannula 2572 may extend toward the 2504 IVC and enter the right atrium of the heart and a reinfusion cannula 2574 extend into the left atrium via crossing interatrial septum. For example, a reinfusion cannula 2574 may comprise a cannula extender 2527 that allows the reinfusion cannula 2574 to bypass chambers within the heart to insert oxygenated blood at a deeper point within the heart. The cannula extender 2527 may proceed through the right atrium and right ventricle of the heart into the pulmonary artery, thereby facilitating blood flow from the superior vena cava to the pulmonary artery while bypassing the right atrium and right ventricle.

In some implementations, the cannulae may comprise a tapered diameter to allow for insertion into smaller blood vessels. In some embodiments, a drainage cannula 2574 may comprise a balloon cuff 2530. In some implementations, the dual cannula 2570 may comprise one or more cannula. In some aspects, the dual cannula 2570 may comprise separate cannula that are positioned via a balloon cuff 2530.

In some embodiments, a reinfusion cannula 2574 may comprise a balloon cuff 2530. In some embodiments, the drainage cannula 2572 may comprise one or more cannula flow mechanism 2540, 2542. In some implementations, the cannula flow mechanism 2540, 2542 may allow for deoxygenated blood extract from one or more locations within the blood vessel 2510.

For example, the drainage cannula 2572 may extrude from both sides of a balloon cuff 2030 and extract blood from the blood vessel 2510 as well as the right atrium of the heart. A cannula flow mechanism 2542 may collect deoxygenated blood from one side of the balloon cuff 2530 and another cannula flow mechanism 2540 may collect blood from the alternative side of the balloon cuff 2530. This plurality of cannula flow mechanism 2540 may allow deoxygenated blood to continue flowing through the blood vessel while the balloon cuff 2530 is inflated and may otherwise block fluid through the blood vessel 2510.

Figure 26:
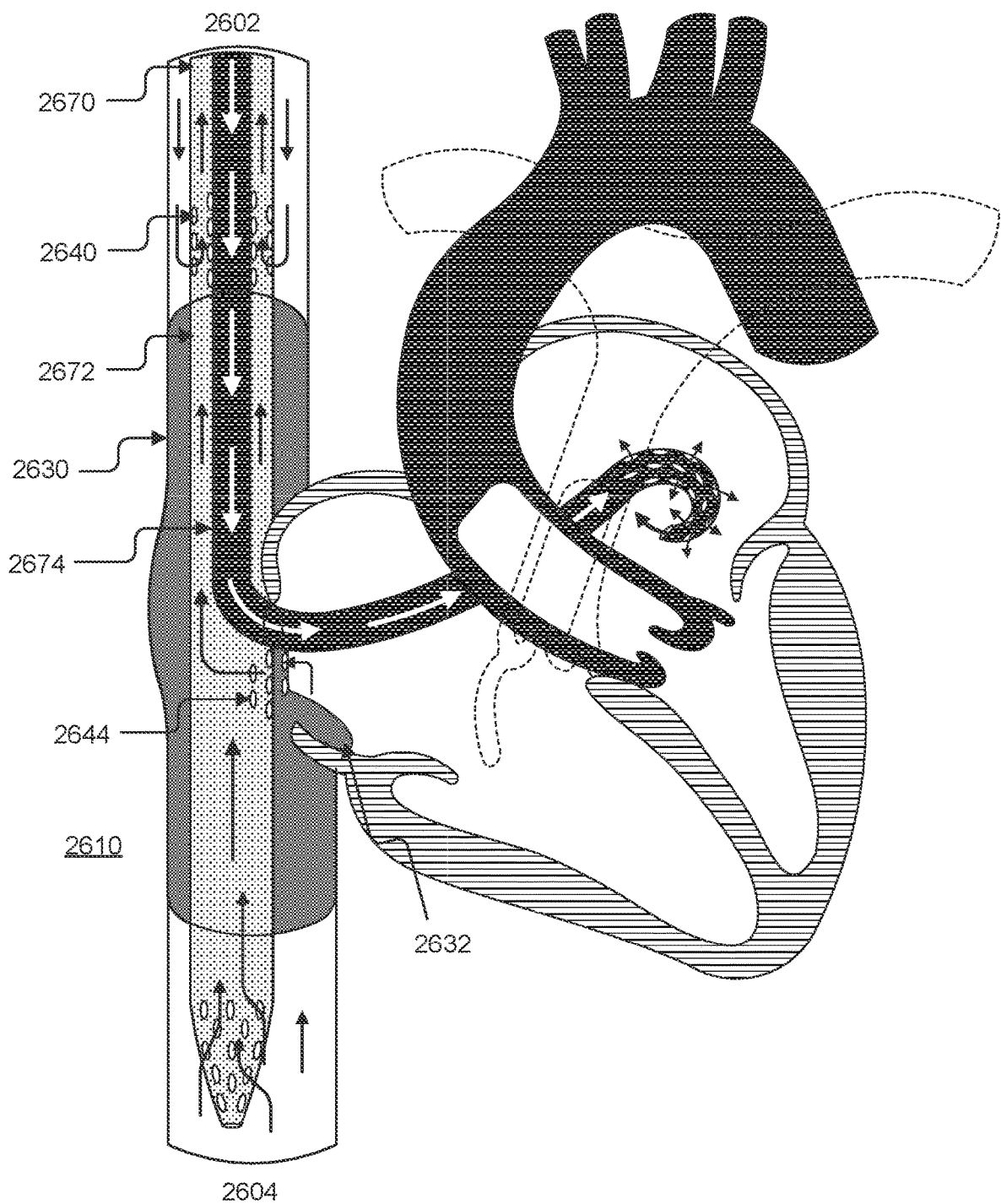
FIG. 26 illustrates an exemplary heart with cannula system, according to some embodiments of the present disclosure.

Referring now to FIG. 26, an exemplary heart with cannula system 2600 is illustrated. In some implementations, the dual cannula 2670 may comprise one or more cannula. In some embodiments, a drainage cannula 2672 may comprise a balloon cuff 2630. In some aspects, the dual cannula 2670 may be positioned via a balloon cuff 2630. In some aspects, the cannulae 2672, 2674 may interact with different regions of the vessels and heart. As an example, the drainage cannula 2672 may extend toward the 2604 IVC and a reinfusion cannula 2674 may extend into the left atrium.

In some embodiments, a reinfusion cannula 2674 may comprise a balloon cuff 2630. The positioning of the balloon cuff 2630 may be secured via a positioning arm 2632 that may apply a stabilizing force on the entrance wall of the heart. In some embodiments, the drainage cannula 2672 may comprise one or more cannula flow mechanism 2640, 2642.

In some implementations, the cannula flow mechanism 2640, 2642 may allow for deoxygenated blood extraction from one or more locations within the blood vessel 2610. For example, the drainage cannula 2672 may extrude from both sides of a balloon cuff 2630 in addition to collecting from the right atrium of the heart. A cannula flow mechanism 2642 may collect deoxygenated blood from one side of the balloon cuff 2630 and another cannula flow mechanism 2640 may collect blood from the alternative side of the balloon cuff 2630. In some implementations, a flow mechanism 2644 may collect blood from inside of the right atrium. This plurality of cannula flow mechanism 2640 may allow deoxygenated blood to continue flowing through the blood vessel while the balloon cuff 2630 is inflated and may otherwise block fluid through the blood vessel 2610.

Figure 27A:
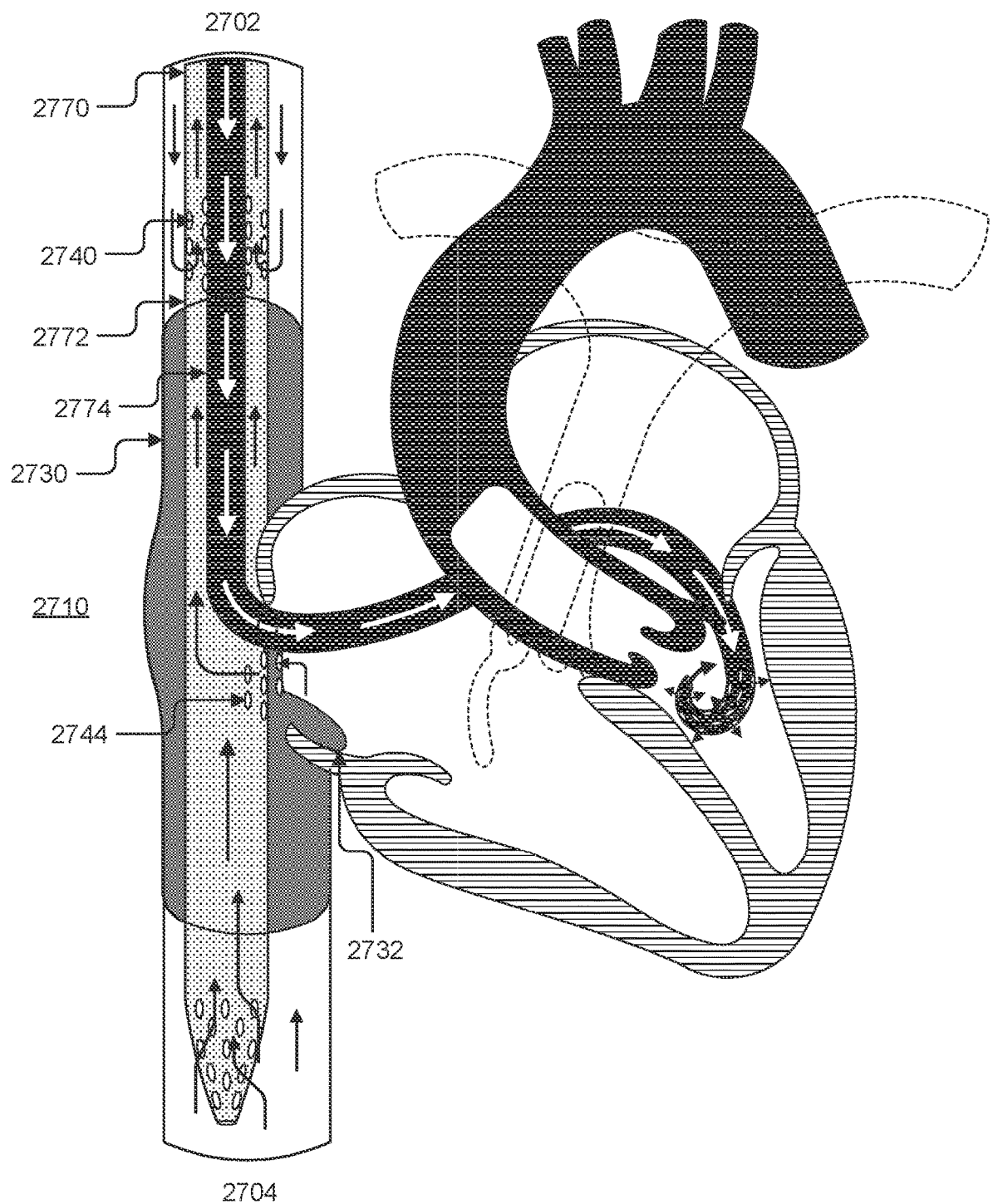
FIG. 27A illustrates an exemplary heart with cannula system, according to some embodiments of the present disclosure.
Figure 27B:
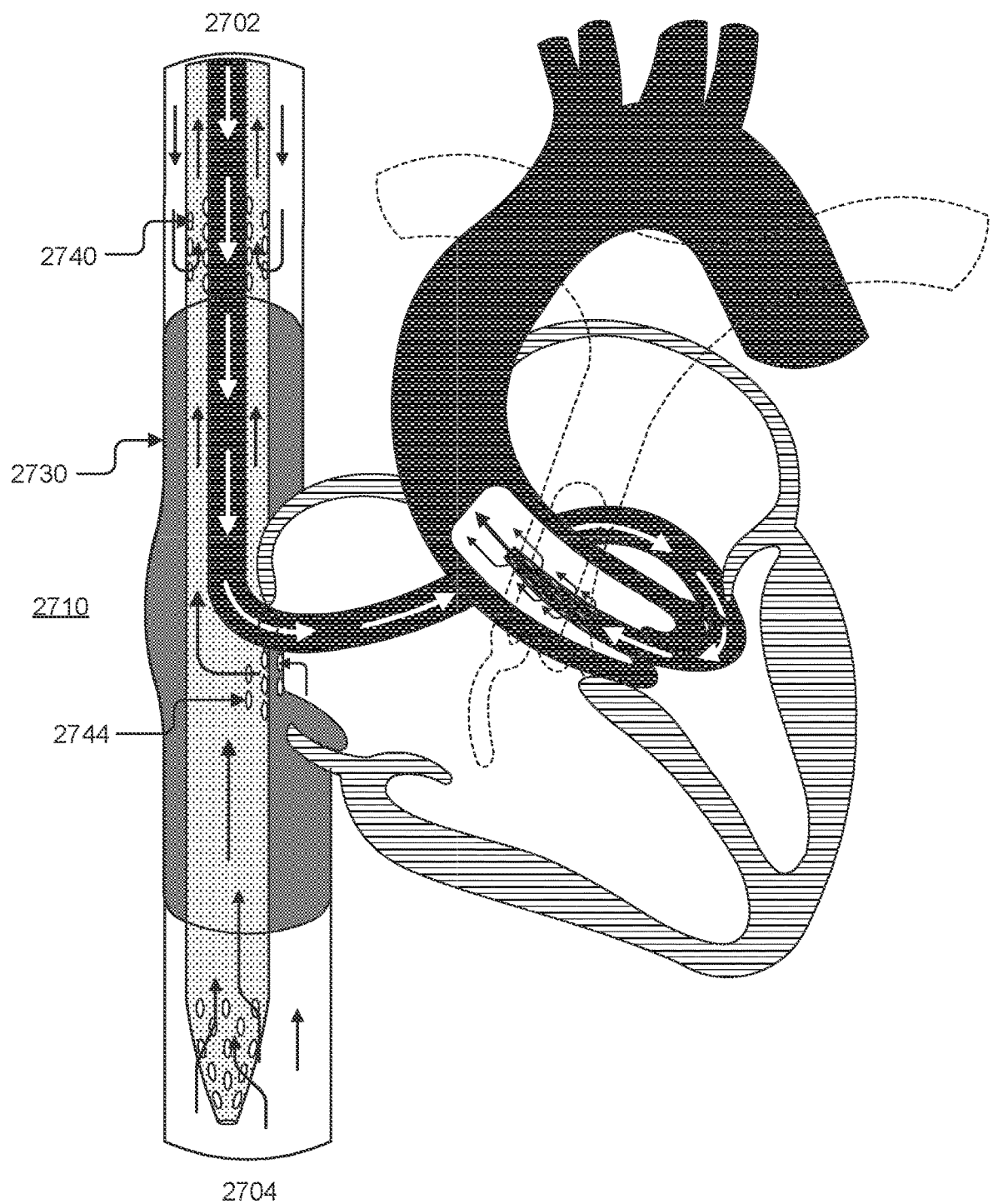
FIG. 27B illustrates an exemplary heart with cannula system, according to some embodiments of the present disclosure.

Referring now to FIGS. 27A-27B, an exemplary heart with cannula system 2700 is illustrated. In some implementations, the dual cannula 2770 may comprise one or more cannula. In some embodiments, a drainage cannula 2772 may comprise a balloon cuff 2730. In some aspects, the dual cannula 2770 may be positioned via a balloon cuff 2730. In some aspects, the cannulae 2772, 2774 may interact with different regions of the vessels and heart. As an example, the drainage cannula 2772 may extend toward the IVC 2704 and a reinfusion cannula 2774 may extend into the left ventricle. In some implementations, additional flow mechanism 2744 may collect blood from inside of right atrium.

As another example, a reinfusion cannula 2774 may comprise a cannula extender that allows the reinfusion cannula 2774 to bypass the chambers within the heart to insert oxygenated blood into the aortic arch. The cannula may thereby facilitate blood flow from the superior vena cava to the left ventricle or aortic arch while bypassing the chambers within the heart. In some embodiments, a reinfusion cannula 2774 may comprise a balloon cuff 2730. The positioning of the balloon cuff 2730 may be secured via a positioning arm 2732 that may apply a stabilizing force on the entrance wall of the heart. In some embodiments, the dual cannula system 2770 may be inserted from IVC 2704 instead of SVC 2702.

In some embodiments, the drainage cannula 2772 may comprise one or more cannula flow mechanism 2740, 2742, 2744. In some implementations, the cannula flow mechanism 2740, 2742 may allow for deoxygenated blood extraction from one or more locations within the blood vessel 2710. For example, the drainage cannula 2772 may extrude from both sides of a balloon cuff 2730 in addition to collecting from the right atrium of the heart. A cannula flow mechanism 2742 may collect deoxygenated blood from one side of the balloon cuff 2730 and another cannula flow mechanism 2740 may collect blood from the alternative side of the balloon cuff 2730. In some implementations, the flow mechanism 2744 may collect blood from inside of right atrium. This plurality of cannula flow mechanism 2740 may allow deoxygenated blood to continue flowing through the blood vessel while the balloon cuff 2730 is inflated and may otherwise block fluid through the blood vessel 2710.

Figures 28A, 28B:
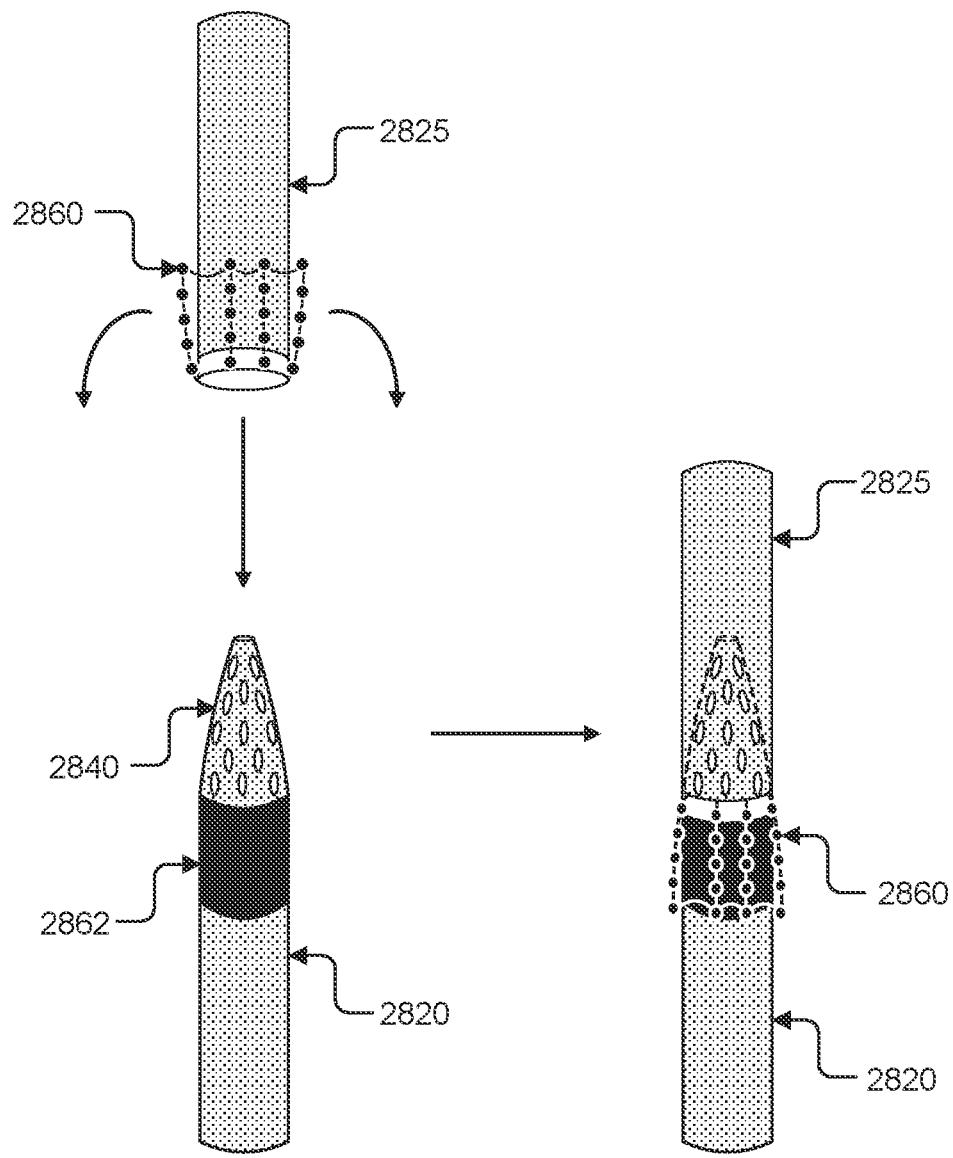
FIG. 28A illustrates an exemplary cannula system with connector mechanism, according to some embodiments of the present disclosure.
FIG. 28B illustrates an exemplary cannula system with connector mechanism, according to some embodiments of the present disclosure.

Referring now to FIGS. 28A-28B, exemplary cannulas 2820, 2825 with connector mechanisms 2860, 2862 are illustrated. In some embodiments, a number of connector mechanisms 2860, 2862 may interface to join a number of cannulas 2820, 2825. In some implementations, a cannula flow mechanism 2840 may extend from the distal end of the cannula 2820.

Figures 29A, 29B:
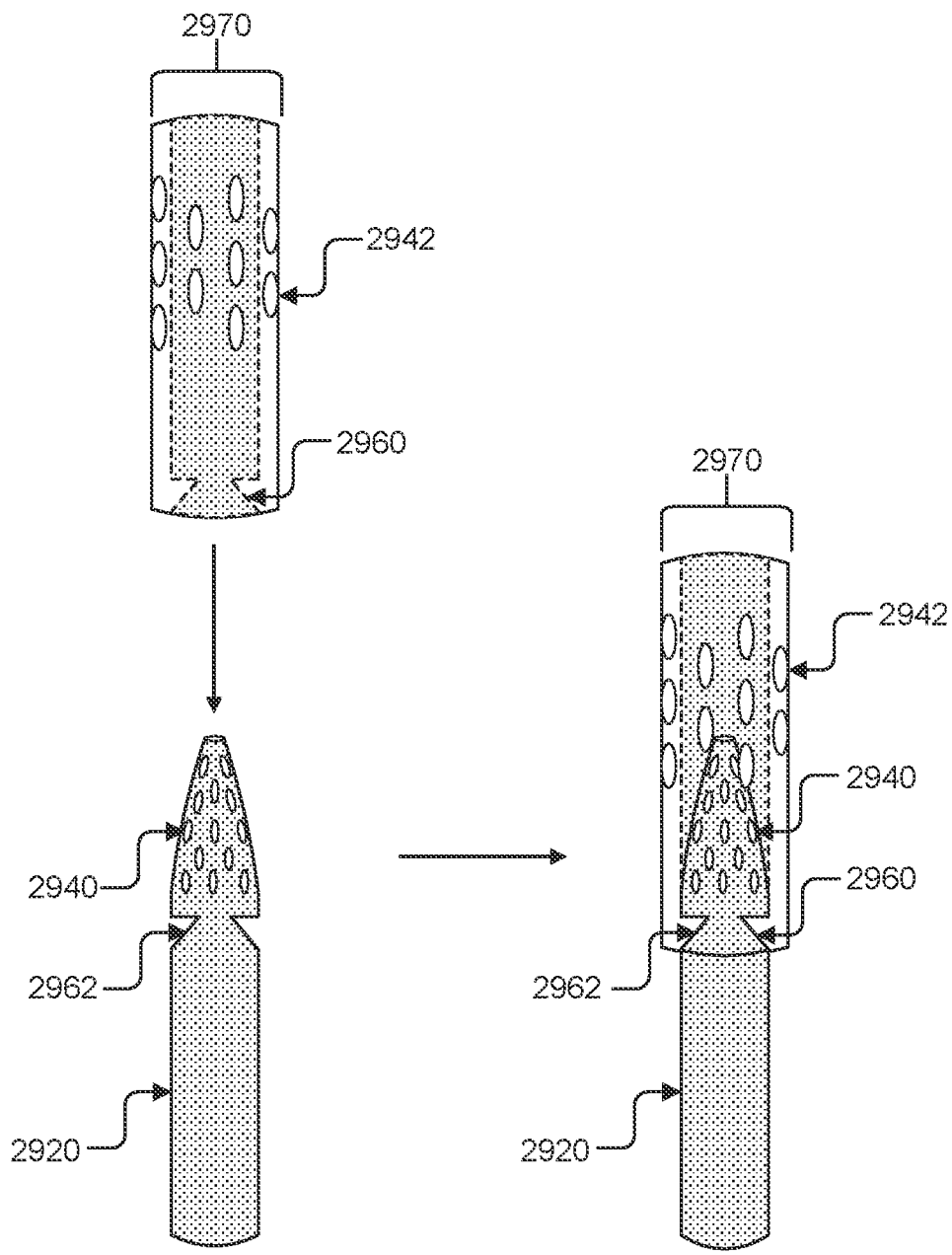
FIG. 29A illustrates an exemplary cannula system with connector mechanism, according to some embodiments of the present disclosure.
FIG. 29B illustrates an exemplary cannula system with connector mechanism, according to some embodiments of the present disclosure.

Referring now to FIGS. 29A-29B, exemplary cannulas 2920, 2970 with connector mechanisms 2960, 2962 are illustrated. In some embodiments, a number of connector mechanisms 2960, 2962 may interface to join a number of cannulas 2920, 2970. In some implementations, a cannula flow mechanism 2940 may extend from the distal end of the cannula 2520. In some aspects, the cannula 2920 may be inserted into a dual cannula 2970. In some embodiments, the cannula 2920 may be inserted into the end of a dual cannula without obstructing fluid flow.

For example, oxygenated blood may flow into the blood vessel through a cannula flow mechanism 2942 in the dual cannula 2970. The dual cannula 2970 may connect to a cannula 2920 via an inner cannula within the dual cannula 2970 that extracts blood via a cannula flow mechanism 2940 that is inserted into the inner cannula of the dual cannula 2970. The mated connection between the connector mechanisms 2960, 2962 may prevent occlusion.

Figures 30A, 30B:
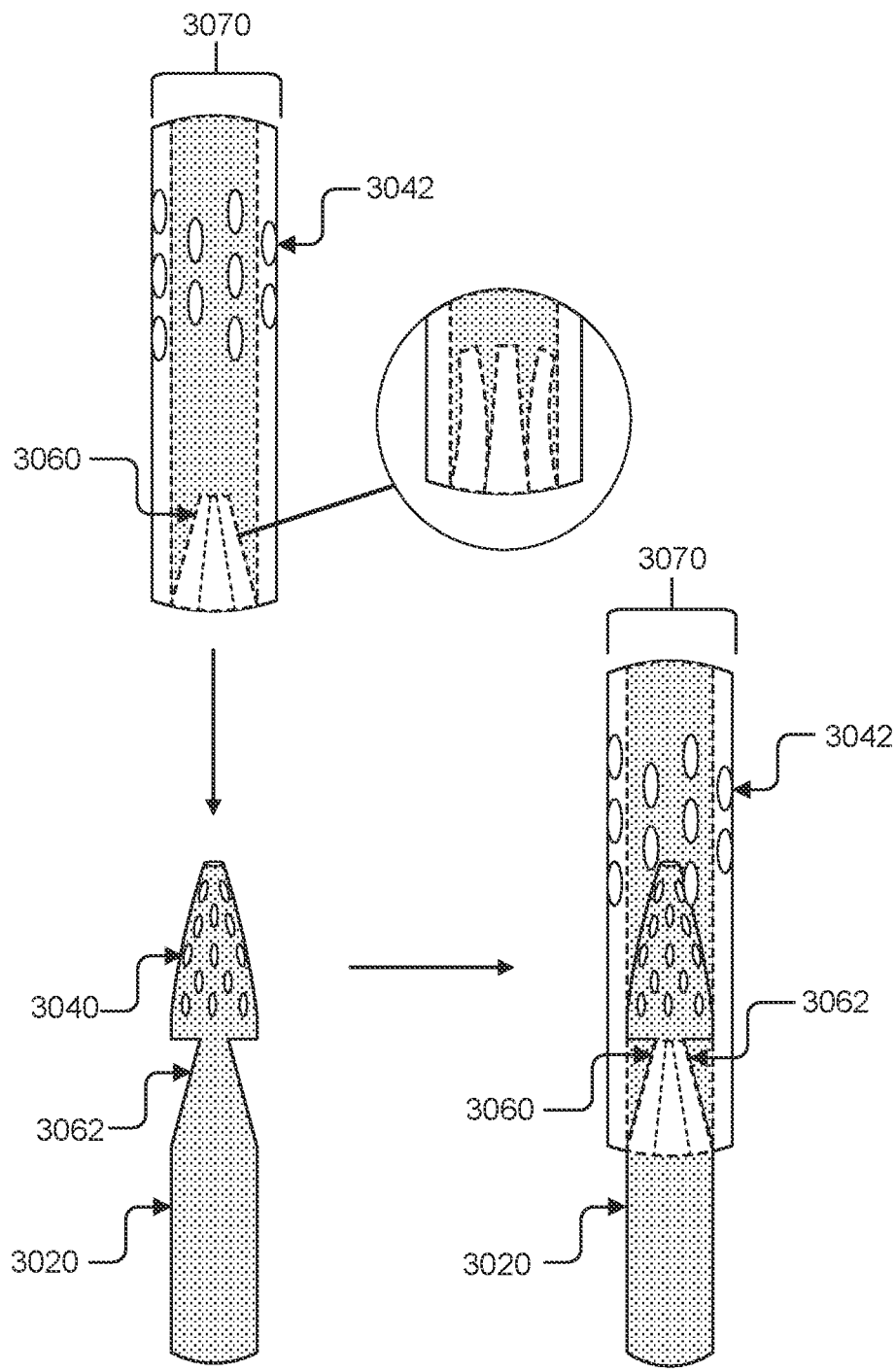
FIG. 30A illustrates an exemplary cannula system with connector mechanism, according to some embodiments of the present disclosure.
FIG. 30B illustrates an exemplary cannula system with connector mechanism, according to some embodiments of the present disclosure.

Referring now to FIGS. 30A-30B, exemplary cannulas 3020, 3070 with connector mechanisms 3060, 3062 are illustrated. In some embodiments, a number of connector mechanisms 3060, 3062 may interface to join a number of cannulas 3020, 3070. In some implementations, a cannula flow mechanism 3040 may extend from the distal end of the cannula 3020. In some aspects, the cannula 3020 may be inserted into a dual cannula 3070. In some embodiments, the cannula 3020 may be inserted into the end of a dual cannula without obstructing fluid flow.

For example, oxygenated blood may flow into the blood vessel through a cannula flow mechanism 3042 in the dual cannula 3070. The dual cannula 3070 may connect to a cannula 3020 via an inner cannula within the dual cannula 3070 that extracts blood via a cannula flow mechanism 3040 that is inserted into the inner cannula of the dual cannula 3070. The mated connection between the connector mechanisms 3060, 3062 may prevent occlusion.

Referring now to FIGS. 31A-31B, an exemplary cannula system 3100 with balloon cuff 3130 is illustrated. In some embodiments, the balloon cuff may comprise a balloon cuff tube 3131. In some implementations, the balloon cuff tube 3131 may comprise an internal diameter sufficient to allow the insertion of one or more cannula 3172, 3174. In some aspects, the balloon cuff 3130 may comprise a positioning arm 3132.

In some embodiments, the balloon cuff may comprise a plurality of balloon cuff 3134, 3136. In some implementations, the balloon cuff 3134, 3136 may assist in securing the balloon in place. In some aspects, the balloon cuffs 3134, 3136 may assist securing the cannula 3172, 3174. In some embodiments, the balloon cuffs 3134, 3136 may maintain openings for the insertion of cannula 3172, 3174. In some implementations, the balloon cuffs 3134, 3136 may allow for some flexibility with fit to ensure that the cannula openings 3140 are not blocked once inserted.

Figure 32A:
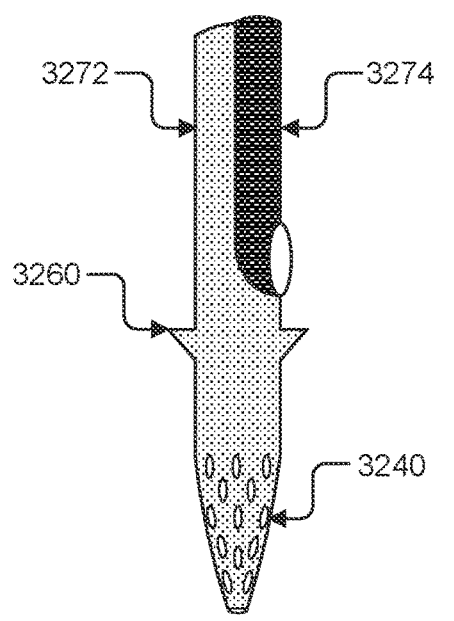
FIG. 32A illustrates an exemplary cannula system with connector mechanism, according to some embodiments of the present disclosure.
Figure 32B:
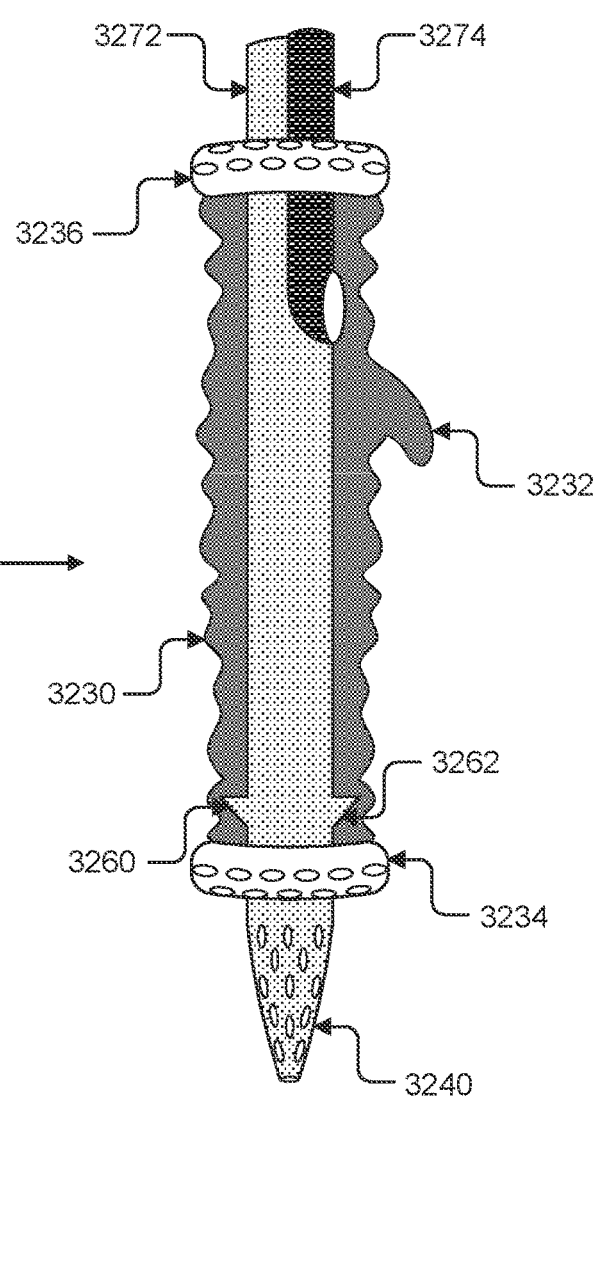
FIG. 32B illustrates an exemplary cannula system with connector mechanism, according to some embodiments of the present disclosure.

Referring now to FIGS. 32A-32B, an exemplary cannula system 3200 with balloon cuff 3230 is illustrated. In some embodiments, the balloon cuff may comprise a balloon cuff tube 3231. In some implementations, the balloon cuff tube 3231 may comprise an internal diameter sufficient to allow the insertion of one or more cannula 3272, 3274. In some embodiments, the inserted cannula 3272, 3274 may comprise a cannula connection mechanism 3260 that may interface with a cannula connection mechanism 3262 within the wall of the balloon cuff tube 3231. This may allow the cannula placement to be precise with intentional positioning.

In some aspects, the balloon cuff 3230 may comprise a positioning arm 3232. In some embodiments, the balloon cuff 3230 may comprise a plurality of balloon cuff 3234, 3236. In some implementations, the balloon cuff 3234, 3236 may assist in securing the balloon in place. In some aspects, the balloon cuffs 3234, 3236 may assist securing the cannula 3272, 3274. In some embodiments, the balloon cuffs 3234, 3236 may maintain openings for the insertion of cannula 3272, 3274. In some implementations, the balloon cuffs 3234, 3236 may allow for some flexibility with fit to ensure that the cannula openings 3240 are not blocked once inserted.

CONCLUSION

A number of embodiments of the present disclosure have been described. While this specification contains many specific implementation details, these should not be construed as limitations on the scope of any disclosures or of what may be claimed, but rather as descriptions of features specific to particular embodiments of the present disclosure.

Certain features that are described in this specification in the context of separate embodiments can also be implemented in combination or in a single embodiment. Conversely, various features that are described in the context of a single embodiment can also be implemented in combination in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous.

Moreover, the separation of various system components in the embodiments described above should not be understood as requiring such separation in all embodiments.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order show, or sequential order, to achieve desirable results. In certain implementations, multitasking and parallel processing may be advantageous. Nevertheless, it will be understood that various modifications may be made without departing from the spirit and scope of the claimed disclosure.

What is claimed is:

1. A cannula system comprising:
   a reinfusion cannula comprising a first tubing with an external end and an internal end insertable into a vessel of a patient configured to flow oxygenating fluid through the vessel; a drainage cannula comprising a second tubing with an external end and an internal end insertable into the vessel of a patient configured to flow deoxygenated fluid from the vessel; and
   a first balloon insertable into the vessel, wherein one or both the reinfusion cannula and the drainage cannula is configured to be inserted through at least one portion of the first balloon, wherein the first balloon is configured to surround one or both the reinfusion cannula and the drainage cannula after insertion, wherein the ballon is elongated and extends on both side of an opening of the reinfusion cannula and when inserted into the vessel and inflated, the first balloon is configured to secure one or both the reinfusion cannula and the drainage cannula within the vessel.

2. The system of claim 1, wherein the internal end of the reinfusion cannula is configured to extend further than the internal end of the drainage cannula.

3. The system of claim 1, wherein the first tubing of the reinfusion cannula and the second tubing of the drainage cannula are configured to be coupled together by one or more connection mechanisms.

4. The system of claim 1, wherein the first balloon is insertable into a vena cava of the patient.

5. The system of claim 4, wherein the first balloon comprises a positioning arm configured to position the first balloon within the vena cava.

6. The system of claim 4, wherein the reinfusion cannula is configured to extend into a heart of the patient.

7. The system of claim 6, wherein the first balloon is configured to limit flow of deoxygenated fluid into the heart.

8. The system of claim 1, wherein the reinfusion cannula is configured to insert into one or more of a pulmonary artery, a left atrium, a left ventricle, wherein insertion into the pulmonary artery, the left atrium, or the left ventricle supports a right ventricle.

9. The system of claim 1, wherein the reinfusion cannula is configured to insert into an ascending aorta, wherein insertion into the ascending aorta supports one or more of a left ventricle and a right ventricle.

* * * * *